(12) United States Patent
Kono et al.

(10) Patent No.: US 6,319,390 B1
(45) Date of Patent: Nov. 20, 2001

(54) METHOD OF AND SYSTEM FOR CLEANSING A TOILET OR URINAL

(75) Inventors: Shuhei Kono; Nobuhiro Shono; Kenji Tabata; Masakatsu Kiyohara; Makoto Hayakawa; Mitsuyoshi Kanno; Nobuhiko Kanekuni, all of Kitakyushu (JP)

(73) Assignee: Toto Ltd., Fukuoka-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/793,630

(22) PCT Filed: Aug. 21, 1995

(86) PCT No.: PCT/JP95/01650

§ 371 Date: Feb. 19, 1997

§ 102(e) Date: Feb. 19, 1997

(87) PCT Pub. No.: WO96/06237

PCT Pub. Date: Feb. 29, 1996

(30) Foreign Application Priority Data

Aug. 19, 1994 (JP) .................................................. 6-216695
Nov. 18, 1994 (JP) .................................................. 6-324096

(51) Int. Cl.[7] .................................................. C02F 1/461
(52) U.S. Cl. .......................... 205/701; 205/742; 205/743; 205/744; 204/228.2; 204/229.4; 204/275.1
(58) Field of Search .................................. 205/701, 742, 205/743, 744; 204/229, 275, 275.1, 228.2, 229.4

(56) References Cited

U.S. PATENT DOCUMENTS

| | | | |
|---|---|---|---|
| 3,774,246 | * 11/1973 | Beer | 204/149 |
| 3,939,499 | * 2/1976 | Roberts | 4/1 |
| 3,975,256 | * 8/1976 | Johnson | 204/149 |
| 3,978,208 | 8/1976 | Okada . | |
| 4,416,854 | * 11/1983 | Nielsen | 422/29 |
| 4,492,618 | * 1/1985 | Eder | 205/701 |
| 4,755,354 | 7/1988 | Trinh et al. . | |
| 5,062,940 | * 11/1991 | Davies | 204/229 |
| 5,324,434 | * 6/1994 | Oikawa et al. | 204/229 |
| 5,692,250 | 12/1997 | Oldfelt et al. . | |

FOREIGN PATENT DOCUMENTS 57-119997    7/1982    (JP) .

(List continued on next page.)

Primary Examiner—Arun S. Phasge
(74) Attorney, Agent, or Firm—Jones, Day, Reavis & Pogue

(57) ABSTRACT

A method of and system for cleansing a toilet or urinal are proposed which require less maintenance work and are safer to users than conventional methods using acid substances, and which can prevent the formation of stain on the toilet or urinal effectively and suppress the generation of ammonia sufficiently, thus accomplishing a sufficient countermeasure to the stench. A urinal (A1) is provided with a continuous electrolytic cell (1) having at least a pair of electrodes, a passage formed between the electrodes, and an inlet and an outlet that lead to the passage. Tap water is electrolyzed by the continuous electrolytic cell (1), whereby free chlorine is produced. Then the water containing free chlorine produced is supplied to the urinal (A1), and the water containing free chlorine sterilizes the inside of the urinal, thus preventing urease, an enzyme carried by bacteria, from acting to decompose urea. By this method, the deposition of uric stone and the generation of the stain and stench are suppressed on the surface of the urinal and in the trap of the urinal.

66 Claims, 25 Drawing Sheets

(8 of 25 Drawing Sheet(s) Filed in Color)

FOREIGN PATENT DOCUMENTS

| | | |
|---|---|---|
| S58-26135 | 2/1983 | (JP) . |
| S60-79100 | 5/1985 | (JP) . |
| H61-246281 | 1/1986 | (JP) . |
| S61-95099 | 5/1986 | (JP) . |
| S63-6097 | 1/1988 | (JP) . |
| S63-2-23231 | 9/1988 | (JP) . |
| S63-223231 | 9/1988 | (JP) . |
| H011-27736 | 5/1989 | (JP) . |
| 02027030 | 1/1990 | (JP) . |
| 02111708 | 4/1990 | (JP) . |
| 02147697 | 6/1990 | (JP) . |
| H3-33332 | 2/1991 | (JP) . |
| 04045200 | 2/1992 | (JP) . |
| H05-27182 | 4/1993 | (JP) . |
| H5-27182 | 4/1993 | (JP) . |
| H5-161695 | 6/1993 | (JP) . |
| H5-170613 | 7/1993 | (JP) . |
| H6-218392 | 8/1994 | (JP) . |
| H6-62996 | 8/1994 | (JP) . |
| H07-535 | 1/1995 | (JP) . |
| 07136660 | 5/1995 | (JP) . |
| WO/82/01319 | 4/1982 | (WO) . |
| WO9532922 | 12/1995 | (WO) . |

\* cited by examiner

Fig.19(a)  Fig.19(b)
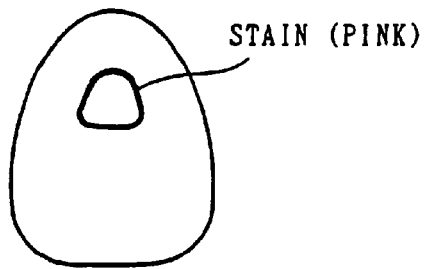
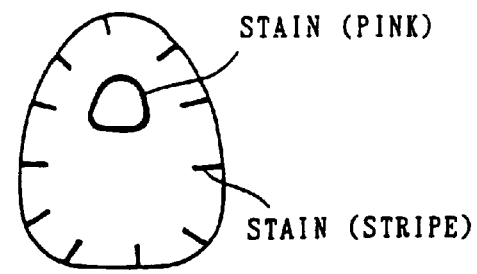
Fig.20
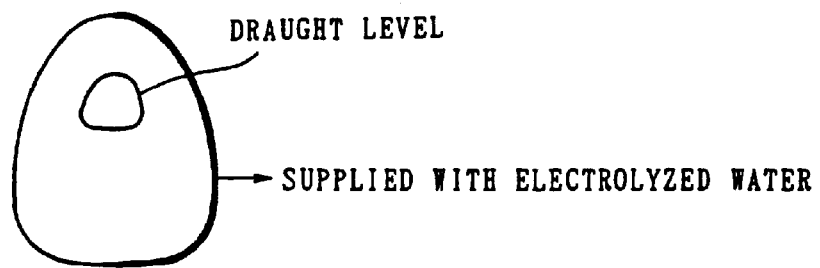
Fig.21
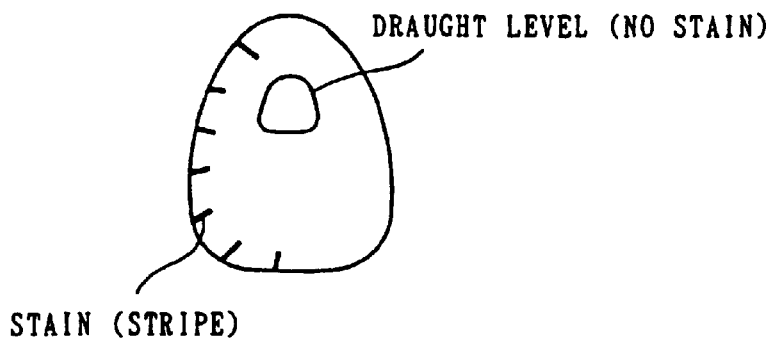

METHOD OF AND SYSTEM FOR CLEANSING A TOILET OR URINAL

This application is a 371 of PCT/JP95/01650 filed Aug. 21, 1995.

TECHNICAL FIELD

The present invention relates to a method of and a system for cleansing a toilet or urinal. It should be noted that the term "toilet" includes both "toilet" and "urinal" hereinafter, if not specified.

BACKGROUND ART

One of the main causes of the stain of a toilet is the deposition of uric stone. The process by which the uric stone deposits is considered to be as follows: when urea contained in urine is decomposed by urease, an enzyme carried by bacteria, ammonia is generated, whereby the pH of a mixed drain consisting of urea and flush water increases; as the pH increases, the solubility of calcium phosphate which is produced by the reaction of calcium ions and phosphate ions contained in the urine decreases, and calcium phosphate together with organic components precipitates on such a place as the inner surface of the toilet. This is the "uric stone".

Accordingly, some methods are conventionally used wherein the pH of the mixed drain is kept low enough to impede the precipitation of calcium phosphate.

For example, the Japanese Published Examined Patent Application No. H5-57312 discloses a method wherein the pH of the urine, or a mixed drain composed of urine and flush water, is kept between 5 and 7.5 by adding acid substances.

The conventional method using acid substances, however, is not a satisfactory countermeasure to a stench since it cannot suppress the generation of ammonia adequately.

Besides, the method is accompanied by the problem that the downstream pipe of the toilet may corrode.

Furthermore, the maintenance work for supplying an acid substance is necessary and the supplying work may be sometimes dangerous.

The present invention is accomplished in view of the above problems, the main object of which is to provide a method of cleansing a toilet by which the formation of the stain of the toilet is effectively prevented and the generation of ammonia is suppressed adequately so that the stench can be prevented sufficiently.

Further, the present invention provides a system for cleansing a toilet which requires less maintenance work and is safer to users than the conventional method using acid substances.

DISCLOSURE OF THE INVENTION

In order to solve the above problems, the present invention provides, as a first invention, a method of cleansing a toilet comprising a process of killing urease-carrying bacteria and a process of removing urease from the toilet.

In order to solve the above problems, the present invention provides, as a second invention, a method of cleansing a toilet comprising a process of inhibiting the enzymatic activity of urease.

In a preferable form of the second invention, the method comprises a process of inhibiting the enzymatic activity of urease and a process of removing urease from the toilet.

In a preferable form of the present invention, the method comprises a process of killing urease-carrying bacteria and a process of inhibiting the enzymatic activity of urease.

In a preferable form of the present invention, the method comprises a process of killing urease-carrying bacteria together with inhibiting the enzymatic activity of urease.

In another preferable form of the present invention, the method comprises a process of killing urease-carrying bacteria, a process of inhibiting the enzymatic activity of urease and a process of removing urease from the toilet.

In another preferable form of the present invention, the method comprises a process of killing urease-carrying bacteria together with inhibiting the enzymatic activity of urease and a process of removing urease from the toilet.

In a preferable form of the first invention, the process of killing urease-carrying bacteria is a process wherein a sterilizing substance or ions are contacted with the toilet.

In another preferable form of the first invention, the process of killing urease-carrying bacteria is a process wherein a liquid containing a sterilizing substance or ions is contacted with the toilet.

In a preferable form of the first invention, the process of removing urease from the toilet is a process wherein bacteria are removed from the toilet together with flush water.

In another preferable form of the first invention, the process of removing urease from the toilet is a process wherein bacteria are removed from the toilet together with a liquid containing a sterilizing substance or ions.

In another preferable form of the first invention, the liquid containing a sterilizing substance or ions contains a substance that inhibits the enzymatic activity of urease.

In another preferable form of the first invention, the pH of the liquid containing a sterilizing substance or ions is 5.5 or below.

In a preferable form of the present invention, the liquid containing a sterilizing substance or ions is a liquid containing free chlorine.

In another preferable form of the present invention, the liquid containing a sterilizing substance or ions is a liquid containing bound chlorine.

In another preferable form of the present invention, the liquid containing a sterilizing substance or ions is ozone-water.

In another preferable form of the present invention, the liquid containing a sterilizing substance or ions is a liquid containing antibacterial metal ions.

In a more preferable form, the concentration of free chlorine is 0.1 mg/l or above.

In a more preferable form, the concentration of free chlorine is 0.5 mg/l or above.

In another preferable form of the present invention, the free chlorine is obtained by electrolyzing a water containing chlorine ions.

In another preferable form of the present invention, the liquid containing a sterilizing substance or ions is an acid solution containing free chlorine.

In a preferable form of the first invention, the ozone concentration of the ozone-water is 0.01 mg/l or above.

In a more preferable form, the ozone concentration of the ozone-water is 0.05 mg/l or above.

In another preferable form of the first invention, the ozone-water is obtained by dissolving ozone produced by a silent discharge in a water, or by producing ozone in a water by electrolyzing the water.

In another preferable form of the first invention, the liquid containing antibacterial metal ions is a liquid containing silver ions whose concentration is 1 μg/l or above.

In a more preferable form, the liquid containing antibacterial metal ions is a liquid containing silver ions whose concentration is 10 μg/l or above.

In another preferable form of the first invention, the liquid containing antibacterial metal ions is a liquid containing the antibacterial metal ions released from an antibacterial metal ion holder.

In another preferable form of the first invention, the antibacterial metal ion holder is placed in the trap of the toilet where a standing water is retained.

In another preferable form of the first invention, the liquid containing a sterilizing substance or ions is supplied to the toilet at predetermined time intervals.

In another preferable form of the first invention, the liquid containing a sterilizing substance or ions is supplied to the toilet only at night.

In another preferable form of the first invention, the liquid containing a sterilizing substance or ions is supplied to the toilet only at night and at predetermined time intervals.

In another preferable form of the first invention, the liquid containing a sterilizing substance or ions is supplied to the toilet in case that the toilet is not used for a predetermined period of time after the last use thereof.

In another preferable form of the first invention, the liquid containing a sterilizing substance or ions is supplied to the toilet at predetermined time intervals in case that the toilet is not used for a predetermined period of time after the last use thereof.

In another preferable form of the first invention, the liquid containing a sterilizing substance or ions is supplied to the toilet at every flush after use.

In another preferable form of the first invention, the liquid containing a sterilizing substance or ions is supplied to the toilet just before or just after the end of a flush after use.

In another preferable form of the first invention, the liquid containing antibacterial metal ions is retained as the standing water of the toilet only at night.

In another preferable form of the first invention, the liquid containing antibacterial metal ions is retained as the standing water of the toilet in case that the toilet is not used for a predetermined period of time after the last use thereof.

In another form of the present invention, the water containing free chlorine whose free chlorine concentration is 0.2 μg/l or above is supplied to the toilet.

In a more preferable form, the water containing free chlorine whose free chlorine concentration is 0.02 mg/l or above is supplied to the toilet.

In another form of the present invention, the number of bacteria in the standing water of the toilet is maintained under 1×10⁴ CFU/ml.

In another preferable form of the present invention, the number of bacteria in the standing water of the toilet is maintained under 1×10⁴ CFU/ml by supplying a liquid containing a sterilizing substance or ions to the toilet.

In another preferable form of the present invention, said liquid containing a sterilizing substance or ions is supplied to the toilet at all times.

In another preferable form of the present invention, said liquid containing a sterilizing substance or ions is supplied after renewing the standing water of the toilet by a normal flush operation.

In another preferable form of the present invention, said liquid containing a sterilizing substance or ions that is supplied to toilet at all times is a water containing free chlorine whose free chlorine concentration is 0.2 μg/l or above.

In another preferable form of the present invention, a liquid containing a sterilizing substance or ions is supplied in case that the toilet is not used for a predetermined period of time after a flush operation subsequent to the last use thereof, wherein the liquid containing a sterilizing substance or ions that is supplied first to the toilet is a water containing free chlorine whose free chlorine concentration is 0.1 mg/l or above.

In another preferable form of the present invention, a liquid containing a sterilizing substance or ions is supplied to the toilet only at night, wherein the liquid containing a sterilizing substance or ions that is supplied to the toilet first at night is a water containing free chlorine whose free chlorine concentration is 0.1 mg/l or above.

In another preferable form of the present invention, said liquid containing a sterilizing substance or ions that is supplied to the toilet after renewing the standing water of the toilet by a normal flush operation is a water containing free chlorine whose free chlorine concentration is 0.02 mg/l or above.

The present invention provides a system for cleansing a toilet, comprising: a continuous electrolytic cell having at least a pair of electrodes, a passage formed between the electrodes, and an inlet and an outlet that lead to the passage; a first branch connecting a flush water supply line at an upstream of a water supply valve and the inlet of the continuous electrolytic cell; a second branch connecting the flush water supply line at a downstream of the water supply valve and the outlet of the continuous electrolytic cell; an on/off valve provided in the first branch; and a controller having means for opening the on/off valve and applying voltage between the electrodes.

The above controller may open the on/off valve at predetermined time intervals, wherein, further, the controller may renew the standing water of the toilet by a flush before opening the on/off valve.

The above controller may open the on/off valve only at night, wherein, further, the controller may renew the standing water of the toilet by a flush before opening the on/off valve.

The above controller may open the on/off valve in case that the toilet is not used for a predetermined period of time after the last use thereof, wherein, further, the controller may renew the standing water of the toilet by a flush before opening the on/off valve.

The above controller may open the on/off valve at every flush after use, wherein, further, the controller may renew the standing water of the toilet by a flush before opening the on/off valve.

The above controller may open the on/off valve just before or just after the toilet is flushed after it is used.

The present invention provides a system for cleansing a toilet, comprising: a continuous electrolytic cell having at least a pair of electrodes, a passage formed between the electrodes, and an inlet and an outlet that lead to the passage; a first branch connecting a flush water supply line at an upstream of a water supply valve and the inlet of the continuous electrolytic cell; a second branch connecting the flush water supply line at a downstream of the water supply valve and the outlet of the continuous electrolytic cell; a flow control valve provided in the first branch; and a controller having means for opening the flow control valve and applying voltage between the electrodes.

The above controller may open the flow control valve at predetermined time intervals, wherein, further, the controller may renew the standing water of the toilet by a flush before opening the flow control valve.

The above controller may open the flow control valve only at night, wherein, further, the controller may renew the standing water of the toilet by a flush before opening the flow control valve.

The above controller may open the flow control valve in case that the toilet is not used for a predetermined period of time after the last use thereof, wherein, further, the controller may renew the standing water of the toilet by a flush before opening the flow control valve.

The above controller may open the flow control valve at every flush after use, wherein, further, the controller may renew the standing water of the toilet by a flush before opening the flow control valve.

The above controller may open the flow control valve just before or just after the end of a flush after use.

The present invention provides a system for cleansing a toilet, comprising: a continuous electrolytic cell having at least a pair of electrodes, a passage formed between the electrodes, and an inlet and an outlet that lead to the passage; a first branch connecting a flush water supply line at an upstream of a water supply valve and the inlet of the continuous electrolytic cell; a second branch connecting the trap of the toilet and the outlet of the continuous electrolytic cell; an on/off valve provided in the first branch; and a controller having means for opening the on/off valve and applying voltage between the electrodes.

The above controller may open the on/off valve at predetermined time intervals, wherein, further, the controller may renew the standing water of the toilet by a flush before opening the on/off valve.

The above controller may open the on/off valve only at night, wherein, further, the controller may renew the standing water of the toilet by a flush before opening the on/off valve.

The above controller may open the on/off valve in case that the toilet is not used for a predetermined period of time after the last use thereof, wherein, further, the controller may renew the standing water of the toilet by a flush before opening the on/off valve.

The above controller may open the on/off valve at every flush after use, wherein, further, the controller may renew the standing water of the toilet by a flush before opening the on/off valve.

The above controller may open the on/off valve just before or just after the end of a flush after use.

The present invention provides a system for cleansing a toilet, comprising: a continuous electrolytic cell having at least a pair of electrodes, a passage formed between the electrodes, and an inlet and an outlet that lead to the passage; a first branch connecting a flush water supply line at an upstream of a water supply valve and the inlet of the continuous electrolytic cell; a second branch connecting the trap of the toilet and the outlet of the continuous electrolytic cell; a flow control valve provided in the first branch; and a controller having means for opening the flow control valve and applying voltage between the electrodes.

The above controller may open the flow control valve at predetermined time intervals, wherein, further, the controller may renew the standing water of the toilet by a flush before opening the flow control valve.

The above controller may open the flow control valve only at night, wherein, further, the controller may renew the standing water of the toilet by a flush before opening the flow control valve.

The above controller may open the flow control valve in case that the toilet is not used for a predetermined period of time after the last use thereof, wherein, further, the controller may renew the standing water of the toilet by a flush before opening the flow control valve.

The above controller may open the flow control valve at every flush after use, wherein, further, the controller may renew the standing water of the toilet by a flush before opening the flow control valve.

The above controller may open the flow control valve just before or just after the end of a flush after use.

The present invention provides a system for cleansing a toilet, comprising: a continuous electrolytic cell provided in a flush water supply line at a downstream of a water supply valve and having at least a pair of electrodes, a passage formed between the electrodes, and an inlet and an outlet that lead to the passage; and a controller having means for applying voltage between the electrodes when the water supply valve is opened.

The present invention provides a system for cleansing a toilet, comprising: a continuous electrolytic cell provided in a flush water supply line at a downstream of a water supply valve and having at least a pair of electrodes, a passage formed between the electrodes, and an inlet and an outlet that lead to the passage; and a controller having means for applying voltage between the electrodes with a delay after the water supply valve is opened.

In the above system, it is preferable that the sterilizing liquid is supplied to the toilet after the standing water of the toilet is renewed by a flush, wherein the sterilizing water may be supplied to the toilet when the surface of the toilet is still wet with the flush water.

In a preferable form of the present invention, the continuous electrolytic cell is a diaphragm less type.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the flush water supply line at a downstream of the water supply valve and the tank-type electrolytic cell; an on/off valve provided in the first branch; another on/off valve provided in the second branch; and a controller having means for applying voltage between the electrodes only when the electrodes are submerged under water and means for opening the on/off valve in the second branch at the moment when the water in the tank-type electrolytic cell reaches a predetermined level.

The above controller may open the on/off valve in the first branch at predetermined time intervals, wherein, further, the controller may renew the standing water of the toilet by a flush before opening the on/off valve in the second branch.

The above controller may open the on/off valve in the first branch only at night, wherein, further, the controller may renew the standing water of the toilet by a flush before opening the on/off valve in the second branch.

The above controller may open the on/off valve in the first branch in case that the toilet is not used for a predetermined period of time after the last use thereof, wherein, further, the controller may renew the standing water of the toilet by a flush before opening the on/off valve in the second branch.

The above controller may open the on/off valve in the first branch at every flush after use, wherein, further, the controller may renew the standing water of the toilet by a flush before opening the on/off valve in the second branch.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the flush water supply line at a downstream of the water supply valve and the tank-type electrolytic cell; a flow control valve provided in the first branch; an on/off valve provided in the second branch; and a controller having means for applying voltage between the electrodes only when the electrodes are submerged under water and means for opening the on/off valve at the moment when the water in the tank-type electrolytic cell reaches a predetermined level.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the flush water supply line at a downstream of the water supply valve and the tank-type electrolytic cell; an on/off valve provided in the first branch; another on/off valve provided in the second branch; and a controller having means for closing the on/off valve in the first branch at the moment when the water in the tank-type electrolytic cell reaches a predetermined level, means for applying voltage between the electrodes only when the electrodes are submerged under water and means for opening the on/off valve in the second branch when the water in the tank-type electrolytic cell is at a predetermined level.

The above controller may open the on/off valve in the second branch at predetermined time intervals when the water in the tank-type electrolytic cell is at a predetermined level, wherein, further, the controller may renew the standing water of the toilet by a flush before opening the on/off valve in the second branch.

The above controller may open the on/off valve in the second branch only at night when the water in the tank-type electrolytic cell is at a predetermined level, wherein, further, the controller may renew the standing water of the toilet by a flush before opening the on/off valve in the second branch.

The above controller may open the on/off valve in the second branch in case that the toilet is not used for a predetermined period of time after the last use thereof when the water in the tank-type electrolytic cell is at a predetermined level, wherein, further, the controller may renew the standing water of the toilet by a flush before opening the on/off valve in the second branch.

The above controller may open the on/off valve in the second branch at every flush after use when the water in the tank-type electrolytic cell is at a predetermined level, wherein, further, the controller may renew the standing water of the toilet by a flush before opening the on/off valve in the second branch.

The above controller may open the on/off valve in the second branch just before or just after the end of a flush after use when the water in the tank-type electrolytic cell is at a predetermined level.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the flush water supply line at a downstream of the water supply valve and the tank-type electrolytic cell; an on/off valve provided in the first branch; another on/off valve provided in the second branch; and a controller having means for closing the on/off valve in the first branch at the moment when the water in the tank-type electrolytic cell reaches a predetermined level, means for applying voltage between the electrodes when the water in the tank-type electrolytic cell is at the predetermined level during a predetermined period of time and means for opening the on/off valve in the second branch after a predetermined period of time since the voltage is applied between the electrodes.

The above controller may open the on/off valve in the second branch at predetermined time intervals, wherein, further, the controller may renew the standing water of the toilet by a flush before opening the on/off valve in the second branch.

The above controller may open the on/off valve in the second branch only at night, wherein, further, the controller may renew the standing water of the toilet by a flush before opening the on/off valve in the second branch.

The above controller may open the on/off valve in the second branch in case that the toilet is not used for a predetermined period of time after the last use thereof, wherein, further, the controller may renew the standing water of the toilet by a flush before opening the on/off valve in the second branch.

The above controller may open the on/off valve in the second branch at every flush after use, wherein, further, the controller may renew the standing water of the toilet by a flush before opening the on/off valve in the second branch.

The above controller may open the on/off valve in the second branch just before or just after the end of a flush after use.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the flush water supply line at a downstream of the water supply valve and the tank-type electrolytic cell; an on/off valve and a flow control valve both provided in the first branch; another on/off valve provided in the second branch; and a controller having means for applying voltage between the electrodes only when the electrodes are submerged under water and means for opening the on/off valve in the second branch at the moment when the water in the tank-type electrolytic cell reaches a predetermined level.

The above controller may open the on/off valve in the first branch at predetermined time intervals, wherein, further, the controller may renew the standing water of the toilet by a flush before opening the on/off valve in the second branch.

The above controller may open the on/off valve in the first branch only at night, wherein, further, the controller may renew the standing water of the toilet by a flush before opening the on/off valve in the second branch.

The above controller may open the on/off valve in the first branch in case that the toilet is not used for a predetermined period of time after the last use thereof, wherein, further, the controller may renew the standing water of the toilet by a flush before opening the on/off valve in the second branch.

The above controller may open the on/off valve in the first branch at every flush after use, wherein, further, the controller may renew the standing water of the toilet by a flush before opening the on/off valve in the second branch.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the trap of the toilet and the tank-type electrolytic cell; a flow control valve provided in the first branch; an on/off valve provided in the second branch; a controller having means for applying voltage between the electrodes only when the electrodes are submerged under water and means for opening the on/off valve at the moment when the water in the tank-type electrolytic cell reaches a predetermined level.

The present invention provides a system for cleansing a toilet, comprising: a tank-type electrolytic cell having at least a pair of electrodes; a first branch connecting a flush water supply line at an upstream of a water supply valve and the tank-type electrolytic cell, a second branch connecting the trap of the toilet and the tank-type electrolytic cell; an on/off valve provided in the first branch; another on/off valve provided in the second branch; and a controller having means for closing the on/off valve in the first branch at the moment when the water in the tank-type electrolytic cell reaches a predetermined level, means for applying voltage between the electrodes only when the electrodes are submerged under water and means for opening the on/off valve in the second branch when the water in the tank-type electrolytic cell is at a predetermined level.

The above controller may open the on/off valve in the second branch at predetermined time intervals when the water in the tank-type electrolytic cell is at a predetermined level, wherein, further, the controller may renew the standing water of the toilet by a flush before opening the on/off valve in the second branch.

The above controller may open the on/off valve in the second branch only at night when the water in the tank-type electrolytic cell is at a predetermined level, wherein, further, the controller may renew the standing water of the toilet by a flush before opening the on/off valve in the second branch.

The above controller may open the on/off valve in the second branch in case that the toilet is not used for a predetermined period of time after the last use thereof when the water in the tank-type electrolytic cell is at a predetermined level, wherein, further, the controller may renew the standing water of the toilet by a flush before opening the on/off valve in the second branch.

The above controller may open the on/off valve in the second branch at every flush after use when the water in the tank-type electrolytic cell is at a predetermined level, wherein, further, the controller may renew the standing water of the toilet by a flush before opening the on/off valve in the second branch.

The above controller may open the on/off valve in the second branch just before or just after the end of a flush after use when the water in the tank-type electrolytic cell is at a predetermined level.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the trap of the toilet and the tank-type electrolytic cell; an on/off valve provided in the first branch; another on/off valve provided in the second branch; and a controller having means for applying voltage between the electrodes only when the electrodes are submerged under water, means for closing the on/off valve in the first branch at the moment when the water in the tank-type electrolyzing reaches a predetermined level, means for applying voltage between the electrodes when the water in the tank-type electrolytic cell is at the predetermined level during a predetermined period of time and means for opening the on/off valve in the second branch after a predetermined period of time since the voltage is applied between the electrodes.

The above controller may open the on/off valve in the second branch at predetermined time intervals, wherein, further, the controller may renew the standing water of the toilet by a flush before opening the on/off valve in the second branch.

The above controller may open the on/off valve in the second branch only at night, wherein, further, the controller may renew the standing water of the toilet by a flush before opening the on/off valve in the second branch.

The above controller may open the on/off valve in the second branch in case that the toilet is not used for a predetermined period of time after the last use thereof, wherein, further, the controller may renew the standing water of the toilet by a flush before opening the on/off valve in the second branch.

The above controller may open the on/off valve in the second branch at every flush after use, wherein, further, the controller may renew the standing water of the toilet by a flush before opening the on/off valve in the second branch.

The above controller may open the on/off valve in the second branch just before or just after the end of a flush after use.

The present invention provides a system for cleansing a toilet, comprising: a tank-type electrolytic cell having at least a pair of electrodes; a first branch connecting a flush water supply line at an upstream of a water supply valve and the tank-type electrolytic cell; a second branch connecting the trap of the toilet and the tank-type electrolytic cell; an on/off valve and a flow control valve both provided in the first branch; another on/off valve provided in the second branch; a controller having means for applying voltage between the electrodes only when the electrodes are submerged under water and means for opening the on/off valve in the second branch at the moment when the water in the tank-type electrolytic cell reaches a predetermined level.

The above controller may open the on/off valve in the first branch at predetermined time intervals, wherein, further, the controller may renew the standing water of the toilet by a flush before opening the on/off valve in the second branch.

The above controller may open the on/off valve in the first branch only at night, wherein, further, the controller may renew the standing water of the toilet by a flush before opening the on/off valve in the second branch.

The above controller may open the on/off valve in the first branch in case that the toilet is not used for a predetermined period of time after the last use thereof, wherein, further, the controller may renew the standing water of the toilet by a flush before opening the on/off valve in the second branch.

The above controller may open the on/off valve in the first branch at every flush after use, wherein, further, the controller may renew the standing water of the toilet by a flush before opening the on/off valve in the second branch.

In a preferable form of the present invention: the means for applying voltage between the electrodes only when the electrodes are submerged under water are means for applying voltage between the electrodes at the moment when a first predetermined period of time elapses since the on/off valve or flow control valve in the first branch is opened; and the means for opening the on/off valve in the second branch at the moment when the water in the tank type-electrolytic cell reaches the predetermined level are means for opening the on/off valve in the second branch at the moment when a second predetermined period of time, which is set longer than the first predetermined period of time, elapses since the on/off valve in the first branch or the on/off valve in the second branch is opened.

The present invention provides a system for cleansing a toilet comprising at least a pair of electrodes provided in a cistern tank and a controller having means for applying voltage between the electrodes only when the electrodes are submerged under water.

In a preferable form of the present invention, the means for applying voltage between the electrodes only when the electrodes are submerged under water are means for applying voltage between the electrodes at the moment when a predetermined period of time elapses since a drain valve of the cistern tank is opened.

The present invention provides a system for cleansing a toilet, comprising: a continuous electrolytic cell having at least a pair of electrodes, a passage formed between the electrodes, and an inlet and an outlet that lead to the passage; a reservoir for storing a liquid produced by the electrolysis and flowing from the outlet; a first branch connecting a flush water supply line at an upstream of a water supply valve and the inlet of the continuous electrolytic cell; a second branch connecting the flush water supply line at a downstream of the water supply valve and the reservoir; an on/off valve provided in the first branch; another on/off valve provided in the second branch; and a controller having means for properly opening the on/off valve in the second branch and applying voltage between the electrodes.

The above controller may open the on/off valve in the second branch at predetermined time intervals when the liquid in the reservoir is at a predetermined level, wherein, further, the controller may renew the standing water of the toilet by a flush before opening the on/off valve in the second branch.

The above controller may open the on/off valve in the second branch only at night when the liquid in the reservoir is at a predetermined level, wherein, further, the controller may renew the standing water of the toilet by a flush before opening the on/off valve in the second branch.

The above controller may open the on/off valve in the second branch in case that the toilet is not used for a predetermined period of time after the last use thereof when the liquid in the reservoir is at a predetermined level, wherein, further, the controller may renew the standing water of the toilet by a flush before opening the on/off valve in the second branch.

The above controller may open the on/off valve in the second branch at every flush after use when the liquid in the reservoir is at a predetermined level, wherein, further, the controller may renew the standing water of the toilet by a flush before opening the on/off valve in the second branch.

The above controller may open the on/off valve in the second branch just before or just after the end of a flush after use when the liquid in the reservoir is at a predetermined level.

The present invention provides a system for cleansing a toilet, comprising: a continuous electrolytic cell having at least a pair of electrodes, a passage formed between the electrodes, and an inlet and an outlet that lead to the passage; a reservoir for storing liquid produced by the electrolysis and flowing from the outlet; a first branch connecting a flush water supply line at an upstream of a water supply valve and the inlet of the continuous electrolytic cell; a second branch connecting the flush water supply line at a downstream of the water supply valve and the reservoir; a flow control valve provided in the first branch; an on/off valve provided in the second branch; and a controller having means for properly opening the on/off valve and applying voltage between the electrodes.

The above controller may open the on/off valve in the second branch at predetermined time intervals when the liquid in the reservoir is at a predetermined level, wherein, further, the controller may renew the standing water of the toilet by a flush before opening the on/off valve in the second branch.

The above controller may open the on/off valve in the second branch only at night when the liquid in the reservoir is at a predetermined level, wherein, further, the controller may renew the standing water of the toilet by a flush before opening the on/off valve in the second branch.

The above controller may open the on/off valve in the second branch in case that the toilet is not used for a predetermined period of time after the last use thereof when the liquid in the reservoir is at a predetermined level, wherein, further, the controller may renew the standing water of the toilet by a flush before opening the on/off valve in the second branch.

The above controller may open the on/off valve in the second branch at every flush after use when the liquid in the reservoir is at a predetermined level, wherein, further, the controller may renew the standing water of the toilet by a flush before opening the on/off valve in the second branch.

The above controller may open the on/off valve in the second branch just before or just after the end of a flush after use when the liquid in the reservoir is at a predetermined level.

In a preferable form of any of the above inventions, chlorine-forming electrodes are used as the electrodes.

The present invention provides a system for cleansing a toilet, comprising: a first branch connecting a flush water supply line at an upstream of a water supply valve and an ozone-water generator; a second branch connecting the flush water supply line at a downstream of the water supply valve and the ozone-water generator; an on/off valve provided in the first branch; and a controller for opening the on/off valve.

The above controller may open the on/off valve in the first branch at predetermined time intervals, wherein, further, the controller may renew the standing water of the toilet by a flush before opening the on/off valve.

The above controller may open the on/off valve in the first branch only at night, wherein, further, the controller may renew the standing water of the toilet by a flush before opening the on/off valve.

The above controller may open the on/off valve in the first branch in case that the toilet is not used for a predetermined period of time after the last use thereof, wherein, further, the controller may renew the standing water of the toilet by a flush before opening the on/off valve.

The above controller may open the on/off valve in the first branch at every flush after use, wherein, further, the controller may renew the standing water of the toilet by a flush before opening the on/off valve.

The controller may open the on/off valve in the first branch just before or just after the end of a flush after use.

The present invention provides a system for cleansing a toilet, comprising: a first branch connecting a flush water supply line at an upstream of a water supply valve and an ozone-water generator; a second branch connecting the trap of the toilet and the ozone-water generator; an on/off valve provided in the first branch; and a controller for opening the on/off valve.

The above controller may open the on/off valve in the first branch at predetermined time intervals, wherein, further, the controller may renew the standing water of the toilet by a flush before opening the on/off valve.

The above controller may open the on/off valve in the first branch only at night, wherein, further, the controller may renew the standing water of the toilet by a flush before opening the on/off valve.

The above controller may open the on/off valve in the first branch in case that the toilet is not used for a predetermined period of time after the last use thereof, wherein, further, the controller may renew the standing water of the toilet by a flush before opening the on/off valve.

The above controller may open the on/off valve in the first branch at every flush after use, wherein, further, the controller may renew the standing water of the toilet by a flush before opening the on/off valve.

The controller may open the on/off valve in the first branch just before or just after the end of a flush after use.

The present invention provides a system for cleansing a toilet, comprising: an ozone-water generator provided in a flush water supply line at a downstream of a water supply valve and a controller having means for instructing the ozone-water generator to start producing ozone-water at the moment when the water supply valve is opened.

The present invention provides a system for cleansing a toilet, comprising: an ozone-water generator provided in a flush water supply line at a downstream of a water supply valve; and a controller having means for instructing the ozone-water generator to start generating ozone-water at the moment when the water supply valve is opened and means for instructing the ozone-water generator to start generating ozone-water with a delay after the water supply valve is opened.

In the above system, the sterilizing liquid is preferably supplied to the toilet after the standing water of the toilet is renewed by a flush, wherein the sterilizing water may be supplied to the toilet when the surface of the toilet is still wet with flush water.

The present invention provides a system for cleansing a toilet, comprising: a first branch connecting a flush water supply line at an upstream of a water supply valve and an ozone-water generator; a second branch connecting the flush water supply line at a downstream of the toilet water supply valve and the ozone-water generator; a flow control valve provided in the first branch; an on/off valve provided in the second branch; and a controller having means for opening the flow control valve, means for closing the flow control valve at the moment when the water in the ozone-water generator reaches a predetermined level, means for instructing the ozone-water generator to start generating ozone-water after closing the flow control valve and means for opening the on/off valve after generating ozone-water.

The above controller may open the flow control valve in the first branch at predetermined time intervals, wherein, further, the controller may renew the standing water of the toilet by a flush before opening the on/off valve.

The above controller may open the flow control valve in the first branch only at night, wherein, further, the controller may renew the standing water of the toilet by a flush before opening the on/off valve.

The above controller may open the flow control valve in the first branch in case that the toilet is not used for a predetermined period of time after the last use thereof, wherein, further, the controller may renew the standing water of the toilet by a flush before opening the on/off valve.

The above controller may open the flow control valve in the first branch at every flush after use, wherein, further, the controller may renew the standing water of the toilet by a flush before opening the on/off valve.

The present invention provides a system for cleansing a toilet, comprising: a first branch connecting a flush water supply line at an upstream of a water supply valve and an ozone-water generator; a second branch connecting the flush water supply line at a downstream of the water supply valve and the ozone-water generator; an on/off valve provided in the first branch; another on/off valve provided in the second branch; a controller having means for opening the on/off valve in the first branch when the water in the ozone-water generator is lower than a predetermined level and for closing the on/off valve in the first branch at the moment when the water in the ozone-water generator reaches the predetermined level, means for instructing the ozone-water generator to start generating ozone-water after closing the on/off valve in the first branch and means for opening the on/off valve in the second branch after generating ozone-water.

The above means of the controller for instructing the ozone-water generator to start operation may instruct the ozone-water generator to start generating ozone-water at predetermined time intervals after closing the on/off valve in the first branch, wherein, further, the controller may renew the standing water of the toilet by a flush before opening the on/off valve in the second branch.

The above means of the controller for instructing the ozone-water generator to start operation may instruct the ozone-water generator to start generating ozone-water only at night after closing the on/off valve in the first branch, wherein, further, the controller may renew the standing water of the toilet by a flush before opening the on/off valve in the second branch.

The above means of the controller for instructing the ozone-water generator to start operation may instruct the ozone-water generator to start generating ozone-water in case that the toilet is not used for a predetermined period of time after the last use thereof after closing the on/off valve in the first branch, wherein, further, the controller may renew the standing water of the toilet by a flush before opening the on/off valve in the second branch.

The above means of the controller for instructing the ozone-water generator to start operation may instruct the ozone-water generator to start generating ozone-water at every flush after use after closing the on/off valve in the first branch, wherein, further, the controller may renew the standing water of the toilet by a flush before opening the on/off valve in the second branch.

The present invention provides a system for cleansing a toilet, comprising: a first branch connecting a flush water supply line at an upstream of a water supply valve and an ozone-water generator; a second branch connecting the trap of the toilet and the ozone-water generator; a flow control valve provided in the first branch; an on/off valve provided in the second branch; and a controller having means for opening the flow control valve, means for closing the flow control valve at the moment when the water in the ozone-water generator reaches a predetermined level, means for instructing the ozone-water generator to start generating ozone-water after closing the flow control valve and means for opening the on/off valve after generating ozone-water.

The above means for opening the flow control valve may open the flow control valve in the first branch at predetermined time intervals, wherein, further, the controller may renew the standing water of the toilet by a flush before opening the on/off valve.

The above means for opening the flow control valve may open the flow control valve in the first branch only at night, wherein, further, the controller may renew the standing water of the toilet by a flush before opening the on/off valve.

The above means for opening the flow control valve may open the flow control valve in the first branch in case that the toilet is not used for a predetermined period of time after the last use thereof, wherein, further, the controller may renew the standing water of the toilet by a flush before opening the on/off valve.

The above means for opening the flow control valve may open the flow control valve in the first branch at every flush after use, wherein, further, the controller may renew the standing water of the toilet by a flush before opening the on/off valve.

The present invention provides a system for cleansing a toilet, comprising: a first branch connecting a flush water supply line at an upstream of a water supply valve and an ozone-water generator; a second branch connecting the trap of the toilet and the ozone-water generator; an on/off valve provided in the first branch; another on/off valve provided in the second branch; a controller having means for opening the on/off valve in the first branch when the water in the ozone-water generator is lower than a predetermined level and for closing the on/off valve in the first branch at the moment when the water in the ozone-water generator reaches the predetermined level, means for instructing the ozone-water generator to start generating ozone-water after closing the on/off valve in the first branch and means for opening the on/off valve in the second branch after generating the ozone-water.

The above means of the controller for instructing the ozone-water generator to start operation may instruct the ozone-water generator to start generating ozone-water at predetermined time intervals after closing the on/off valve in the first branch, wherein, further, the controller may renew the standing water of the toilet by a flush before opening the on/off valve in the second branch.

The above means of the controller for instructing the ozone-water generator to start operation may instruct the ozone-water generator to start generating ozone-water only at night after closing the on/off valve in the first branch wherein, further, the controller may renew the standing water of the toilet by a flush before opening the on/off valve in the second branch.

The above means of the controller for instructing the ozone-water generator to start operation may instruct the ozone-water generator to start generating ozone-water in case that the toilet is not used for a predetermined period of time from the last use of the toilet after closing the on/off valve in the first branch, wherein, further, the controller may renew the standing water of the toilet by a flush before opening the on/off valve in the second branch.

The above means of the controller for instructing the ozone-water generator to start operation may instruct the ozone-water generator to start generating ozone-water at every flush after use after closing the on/off valve in the first branch, wherein, further, the controller may renew the standing water of the toilet by a flush before opening the on/off valve in the second branch.

The present invention provides a system for cleansing a toilet, comprising: a continuous electrolytic cell having at least a pair of electrodes, a passage formed between the electrodes, and an inlet and an outlet that lead to the passage; a reservoir for storing a liquid produced by the electrolysis and flowing from the outlet; a first branch connecting a flush water supply line at an upstream of a water supply valve and the inlet of the continuous electrolytic cell; a second branch connecting the flush water supply line at a downstream of the water supply valve and the reservoir; a flow control valve provided in the first branch; an on/off valve provided in the second branch; and a controller having means for properly opening and closing the on/off valve and applying voltage between the electrodes.

The present invention provides a system for cleansing a toilet, comprising: a continuous electrolytic cell having at least a pair of electrodes, a passage formed between the electrodes, and an inlet and an outlet that lead to the passage; a reservoir for storing a liquid produced by the electrolysis and flowing from the outlet; a first branch connecting a flush water supply line at an upstream of a water supply valve and the inlet of the continuous electrolytic cell; a second branch connecting the flush water supply line at a downstream of the water supply valve and the reservoir; an on/off valve provided in the first branch; another on/off valve provided in the second branch; and second branches and applying voltage between the electrodes.

The present invention provides a system for cleansing a toilet, comprising: a continuous electrolytic cell having at least a pair of electrodes, a passage formed between the electrodes, and an inlet and an outlet that lead to the passage; a reservoir for storing a liquid produced by the electrolysis and flowing from the outlet; a first branch connecting a flush water supply line at an upstream of a water supply valve and the inlet of the continuous electrolytic cell; a second branch connecting the flush water supply line at a downstream of the water supply valve and the reservoir; an on/off valve and a flow control valve both provided in the first branch; another on/off valve provided in the second branch; and a controller having means for properly opening and closing the on/off valves provided in the first and second branches and applying voltage between the electrodes.

When a user urinates to a toilet, the urine attaches to the surface of the toilet or remains in the standing water of the toilet. Generally, bacteria such as bacillus exist in the toilet. When such bacteria exist on the surface of the toilet or in the standing water of the toilet, the urea, large quantity of which is contained in the urine, is decomposed into ammonia and carbon dioxide due to the activity of urease, an enzyme carried by bacteria. When large quantity of ammonia is generated there, a stench arises. Furthermore, the ammonia generated there dissolves in a liquid on the surface of the toilet or in the standing water of the toilet and the pH of the liquid increases. As the pH increases, the calcium ions, contained in the liquid on the surface of the toilet or in the standing water of the toilet, precipitates in the form of carbonate or phosphate, adheres to the toilet in the form of a uric stone and causes a stain.

In the conventional method using acid substance, the deposition of uric stone is prevented by suppressing the increase in pH. The method, however, is not a satisfactory countermeasure to a stench since it cannot suppress the generation of ammonia itself sufficiently.

By the present invention, on the other hand, the generation of ammonia itself is suppressed by removing urease enzyme from the toilet effectively or by inhibiting the enzymatic activity of urease enzyme, whereby the increase in pH due to the solution of ammonia is suppressed, so that the deposition of uric stone is prevented and one of the causes of the stench is also prevented.

With the process of killing urease-carrying bacteria and the process of removing urease from the toilet, the urease enzyme can be effectively removed from the toilet. The reason is explained as follows.

Though some of urease enzyme exist in the urine of human beings, it is in bacteria, such as bacillus, that most of urease enzyme exists. Therefore, as the number of bacteria increases on the surface of the toilet or in the standing water of the toilet, the amount of urease enzyme also increases, and as the bacteria adhere to the toilet firmly, the urease enzyme is also fixed firmly thereto.

Hence, if urease-carrying bacteria are killed and the number of living bacteria is decreased, then not only the increase in the amount of urease can be suppressed, but also the amount of urease that is firmly adhered to the surface of the toilet together with the living bacteria by adhesive organic substance resulting from the life activity of bacteria can be decreased.

After the number of living bacteria, the amount of adhesive organic substance and the amount of urease enzyme are decreased, even a simple flush can remove urease enzyme from the toilet, whereby the generation of ammonia and the increase in pH due to the solution of ammonia are suppressed, so that the deposition of uric stone is prevented and one of the causes of the stench is also prevented.

Instead of the process of killing urease-carrying bacteria, the process of inhibiting the enzymatic activity of urease can be also employed, whereby the generation of ammonia and the increase in pH due to the solution of ammonia are suppressed, so that the deposition of uric stone is prevented and one of the causes of the stench is also prevented.

The process of inhibiting the enzymatic activity of urease may be preferably a process wherein a substance for inhibiting the enzymatic activity of urease is contacted with the toilet, said substance including: salts of heavy metals, halogens, boric acid, quinone, hydrogen peroxide, etc.

With the process of inhibiting the enzymatic activity of urease and the process of removing urease from the toilet, the generation of ammonia can be suppressed by two independent ways, i.e., by inhibiting the enzymatic activity of urease and by removing urease, whereby the generation of ammonia and the increase in pH due to the solution of ammonia are suppressed more effectively, so that the deposition of uric stone is prevented and one of the causes of the stench is also prevented.

With the process of killing urease-carrying bacteria and the process of inhibiting the enzymatic activity of urease, not only the increase and adhesion of urease caused by living bacteria is suppressed, but also the enzymatic activity of urease carried by the remaining bacteria is inhibited, whereby the generation of ammonia is suppressed more effectively. Thus the increase in pH due to the solution of ammonia is suppressed, so that the deposition of uric stone is prevented and one of the causes of the stench is also prevented.

By using the process of killing urease-carrying bacteria together with inhibiting the enzymatic activity of urease, not only the increase and adhesion of urease caused by living bacteria is suppressed, but also the enzymatic activity of urease carried by the remaining bacteria is inhibited, whereby the generation of ammonia is suppressed more effectively. Thus the increase in pH due to the solution of ammonia is suppressed, so that the deposition of uric stone is prevented and one of the causes of the stench is also prevented.

With the process of killing urease-carrying bacteria, the process of inhibiting the enzymatic activity of urease and the process of removing urease from the toilet, the increase and adhesion of urease caused by living bacteria is suppressed, and furthermore, the generation of ammonia can be suppressed by two independent ways, i.e., by inhibiting the enzymatic activity of urease and by removing urease, whereby the generation of ammonia and the increase in pH due to the solution of ammonia are suppressed more effectively, so that the deposition of uric stone is prevented and one of the causes of the stench is also prevented.

With the process of killing urease-carrying bacteria together with inhibiting the enzymatic activity of urease and the process of removing urease from the toilet, the increase and adhesion of urease caused by living bacteria and the generation of ammonia due to the enzymatic activity of urease can be suppressed simultaneously, and further the urease suppressed from adhesion is removed, whereby the generation of ammonia and the increase in pH due to the solution of ammonia are suppressed more effectively, so that the deposition of uric stone is prevented and one of the causes of the stench is also prevented.

The process of killing urease-carrying bacteria is preferably a process in which a sterilizing substance or ions are contacted with the toilet, since it is safer than a method using ultraviolet or the like and is more comfortable in use than a method using heat or the like which changes the temperature of the ambient air.

In the process wherein a sterilizing substance or ions are contacted with the toilet, the following methods can be preferably used: to supply a liquid containing a sterilizing substance or ions to the toilet; to fix a sterilizing substance or ions, or a substance containing the same, on the surface of the toilet (e.g. in the glaze); etc.

The process of killing urease-carrying bacteria is preferably a process in which a liquid containing a sterilizing substance or ions is contacted with the toilet, since, by the process, the deposition of uric stone or the stench can be suppressed, for example, by simply providing means for producing a liquid containing a sterilizing substance or ions, a tank for storing the liquid, etc., in the upstream pipe without replacing the existing toilet with a new one.

The process of removing urease from the toilet is preferably a process in which bacteria are removed from the toilet with flush water, since the process can be accomplished by using an existing toilet flush equipment.

The process of removing urease from the toilet is preferably a process in which a liquid containing a sterilizing substance or ions is used for removing bacteria from the toilet, since, by the process, both the process of killing urease-carrying bacteria and the process of removing urease from the toilet can be conveniently accomplished simultaneously by simply supplying the liquid containing a sterilizing substance or ions in an upstream pipe and discharging the same through a downstream pipe.

The liquid containing a sterilizing substance or ions may contain a substance that inhibits the enzymatic activity of urease, or a substance that kills bacteria and further inhibits the enzymatic activity of urease, whereby the increase and adhesion of urease caused by living bacteria is suppressed and furthermore the generation of ammonia is suppressed by two independent methods of inhibiting the enzymatic activity of urease and of removing urease. Thus the generation of ammonia and the increase in pH due to the solution of ammonia are suppressed more effectively, so that the deposition of uric stone is prevented and one of the causes of the stench is also prevented. The present method is also preferable in that the deposition of uric stone or the stench can be suppressed by, for example, simply providing such as a tank for holding a liquid containing a sterilizing substance or ions in the upstream pipe without replacing the existing toilet with a new one, since liquid is used to contact the substance or ions with the toilet.

When the pH of the liquid containing a sterilizing substance is 5.5 or below, the deposition of uric stone and the generation of ammonia hardly occurs owing to the following two effects in addition to the above effects:

(1) While the solubility of calcium phosphate is very low when the pH is 8 or above, the solubility of calcium phosphate increases and the deposition of uric stone hardly occurs when the pH is kept at 5.5 or below;

(2) the optimal activation pH for urease enzyme is said to be about 7. When, therefore, the pH is kept at 5.5 or below, the activity of urease enzyme deteriorates greatly, and the generation of ammonia hardly occurs.

However, the pH should be preferably 3 or above lest a strong acid should corrode the pipe.

The liquid containing a sterilizing substance or ions may be a liquid containing free chlorine, whereby the generation of ammonia and the increase in pH due to the solution of ammonia are suppressed more effectively, so that the deposition of uric stone is prevented and one of the causes of the stench is also prevented, since free chlorine has high sterilizing power as well as an effect of inhibiting the enzymatic activity of urease even in small quantity. The present method is also preferable in that the deposition of uric stone or the stench can be suppressed by, for example, simply providing such as a tank for holding a liquid containing a sterilizing substance or ions in the upstream pipe without replacing the existing toilet with a new one, since liquid is used to contact the substance or ions with the toilet.

The liquid containing free chlorine can be produced by simply electrolyzing water containing chlorine, such as tap water. This process can be accomplished by simply providing an electrolyzing device in the upstream pipe. Since the device need not be provided with a tank or the like, it occupies little space. Further, the present method is safer to users than the method using acid substances, since the present method requires less maintenance work such as exchanging the liquid in the tank.

The liquid containing a sterilizing substance or ions may be a liquid containing bound chlorine, whereby the generation of ammonia and the increase in pH due to the solution of ammonia are suppressed more effectively, so that the deposition of uric stone is prevented and one of the causes of the stench is also prevented, since bound chlorine has sterilizing power as well as an effect of inhibiting the enzymatic activity of urease. The present method is also preferable in that the deposition of uric stone or the stench can be suppressed by, for example, simply providing such as a tank for storing a liquid containing a sterilizing substance or ions in the upstream pipe without replacing the existing toilet with a new one, since liquid is used to contact the substance or ions with the toilet.

The liquid containing bound chlorine can be produced by simply electrolyzing water containing chlorine and organic nitrogen, such as recycled water or well water. This process can be accomplished by simply providing an electrolyzing device in the upstream pipe. Since the device need not be provided with a tank or the like, it occupies little space and requires less maintenance work such as exchanging a liquid in the tank. Since recycled water can be used as a material, the present method can be suitably applied to such as high-rise buildings or factories with water-recycling facilities. In addition, the bound chlorine is advantageous in that it resides long, since its self-decomposition rate is lower than that of free chlorine, and in that its sterilizing power is so strong that it can kill bacteria entirely in the acting period (residing period) of about five minutes. This characteristic will be discussed in detail later in embodiment 11.

The liquid containing a sterilizing substance or ions may be ozone-water, whereby the generation of ammonia caused by urease and the increase in pH due to the solution of ammonia are suppressed, so that the deposition of uric stone is prevented and one of the causes of the stench is also prevented, since the ozone-water can kill bacteria and oxidize ammonia. The present method is also preferable in that the deposition of uric stone or the stench can be suppressed by, for example, simply providing such as a tank for storing a liquid containing a sterilizing substance or ions in an upstream pipe without replacing the existing toilet with a new one, since liquid is used to contact the substance or ions with the toilet.

The ozone-water can be produced either by simply dissolving ozone produced by a silent discharge in a water, or by generating ozone in a water by electrolysis of the water. This process can be accomplished by simply providing in an upstream pipe an ozonizer unit for inducing the above reactions. Since the unit need not be provided with a tank or the like, it occupies little space and requires less maintenance work such as exchanging a liquid in the tank.

The liquid containing a sterilizing substance or ions may be a liquid containing antibacterial metal ions, whereby the generation of ammonia caused by urease and the increase in pH due to the solution of ammonia are suppressed, so that the deposition of uric stone is prevented and one of the causes of the stench is also prevented, since the antibacterial metal ions have sterilizing power. The present method is also preferable in that the deposition of uric stone or the stench can be suppressed by, for example, simply providing such as a tank for holding a liquid containing a sterilizing substance or ions in an upstream pipe without replacing the existing toilet with a new one, since liquid is used to contact the substance or ions with the toilet.

When the free chlorine concentration is 0.1 mg/l or above, preferably 0.5 mg/l or above, the standing water and the surface of a toilet can be sufficiently sterilized. Consequently, the increase and adhesion of urease due to the action of living bacteria can be effectively suppressed and the increase in pH due to the solution of ammonia are suppressed, so that the deposition of uric stone is prevented and one of the causes of the stench is also prevented.

The free chlorine may be a free chlorine produced by electrolysis of water containing chlorine ions. In this case, the water containing free chlorine can be produced by simply electrolyzing a water containing chlorine, such as tap water. This process can be accomplished by simply providing an electrolyzing device in an upstream pipe. Since the device need not be provided with a tank or the like, it occupies little space. Further, the present method is safer to users than the conventional method using acid substance since the present method requires less maintenance work such as exchanging a liquid in the tank.

The liquid containing a sterilizing substance or ions may be an acid solution containing free chlorine, whereby the deposition of uric stone and the stench can be suppressed more effectively owing to the following effects:

(1) Free chlorine has high sterilizing power as well as an effect of inhibiting the enzymatic activity of urease even in small quantity;

(2) the deposition of uric stone made of calcium phosphate and the like hardly occurs, since the pH hardly becomes 8 or more; and (3) free chlorine exists in the form of hypochlorous acid (HClO) in an acid solution. The free chlorine in this form has sterilizing power about ten times as strong as in the form of hypochlorite ion (ClO$^-$) that exists in a basic solution. Consequently, the generation of ammonia and the increase in pH due to the solution of ammonia are suppressed, so that the deposition of uric stone is prevented and one of the causes of the stench is also prevented.

When the concentration of the ozone-water is 0.01 mg/l or above, preferably 0.05 mg/l or above, the standing water of a toilet and the surface of the toilet can be sterilized sufficiently. Consequently, the increase and adhesion of urease due to the action of living bacteria can be effectively suppressed and the increase in pH due to the solution of ammonia can be suppressed, so that the deposition of uric stone is prevented and one of the causes of the stench is also prevented.

The ozone-water may be produced by such methods as dissolving ozone produced by a silent discharge in a water, or generating ozone in a water by electrolysis of the water. By these methods, the ozone-water can be produced by simply providing a silent discharge type ozone generator or an electrolyzing device in an upstream pipe. Since it is not absolutely necessary to provide a tank or the like, the ozonizer or the device occupies little space. Further, the present methods require less maintenance work, such as exchanging a liquid in the tank, and is safer to users than the conventional method using acid substances.

In case of using silver ions as antibacterial metal ions, when the silver ion concentration is 1 $\mu$g/ or above, preferably 10 $\mu$g/l or above, the standing water of a toilet can be effectively sterilized by mixing a liquid containing the silver ions with the standing water of the toilet and maintaining the ions for an adequate period of time. Consequently, the increase and adhesion of urease due to the action of living bacteria can be effectively suppressed and the increase in pH due to the solution of ammonia is suppressed, so that the deposition of uric stone as well as one of the causes of the stench is prevented.

The instantaneous sterilizing power of the antibacterial metal ions is poorer than that of free chlorine or ozone, but the life span of the antibacterial effect is so long that the advantageous effect can be obtained as the action time gets longer. Therefore, when the ions are used in such a manner as being retained in the standing water of the toilet for an adequate period of time, living bacteria can be decreased and the deposition or the like of uric stone can be prevented even by a small quantity.

The liquid containing antibacterial metal ions may be a liquid containing the antibacterial metal ions released from an antibacterial metal ion holder. This method is preferable in respect of safety, since the maintenance work can be done by simply exchanging the antibacterial metal ion holder.

The antibacterial metal ion holder may be placed in the trap of a toilet where a standing water is retained. By this method, the standing water can be sterilized by the antibacterial metal ions released therein, whereby the increase and adhesion of urease due to the action of living bacteria can be effectively suppressed and the increase in pH due to the solution of ammonia is suppressed, so that the deposition of uric stone as well as one of the causes of the stench is prevented.

The instantaneous sterilizing power of the antibacterial metal ions is poorer than that of free chlorine or ozone. The ions, however, are still preferable in that living bacteria can be decreased and the deposition or the like of uric stone can be prevented by employing just a small quantity of the ions in such a manner as holding them in the standing water of the toilet for an adequate period of time, since the life span of their antibacterial effect is so long that the effect appears more obviously as the action time gets longer.

The liquid containing a sterilizing substance or ions may be supplied to a toilet at predetermined time intervals, whereby living bacteria are killed and removed at intervals, so that the increase and adhesion of living bacteria coming from the ambient air or from other sources and attaching to the toilet can be effectively prevented. Consequently, the increase and adhesion of urease due to the action of living bacteria can be effectively suppressed and the increase in pH due to the solution of ammonia is suppressed, so that the deposition of uric stone as well as one of the causes of the stench is prevented.

The liquid containing a sterilizing substance or ions may be supplied to a toilet only at night. When this method is applied to a toilet that is used only in the day-time and rarely used at night, such as in the office building, in the department store, at the station, at the exhibition site, in the tourist facilities, or in the vehicle running only in the day-time, such a situation can be prevented that bacteria increase in the standing water of the toilet and urease increases and sticks to the surface of the toilet at night or when the toilet is not used, so that the deposition of uric stone can be prevented and one of the causes of the stench can be prevented. In the day-time, neither bacteria nor urease increases in the standing water, since the standing water of the toilet is renewed by the normal flush operation at predetermined time intervals or on every use of the toilet.

In case of supplying the liquid containing a sterilizing substance or ions only at night, it is preferable to renew the standing water of the toilet by supplying a flush water to the toilet before the liquid containing a sterilizing substance or ions is supplied to the toilet. Usually, 99% of the standing water is designed to be renewed by a flush, whereby most of bacteria are removed from the toilet. The remaining bacteria can be completely killed by supplying the liquid containing a sterilizing substance or ions to the toilet subsequently.

In case of supplying the liquid containing a sterilizing substance or ions only at night, it is also preferable that a liquid of high concentration or in large quantity is supplied first at night, whereas liquids of lower concentration or in smaller quantity than the first are supplied secondly and subsequently at night. The number of bacteria in the standing water gradually increases in the day time and is maximized at the beginning of the night. Therefore, it is necessary to make a sufficient sterilization at first by the liquid containing a sterilizing substance or ions of high concentration or in large quantity. On the other hand, the number of bacteria increases so slowly at night that they can be completely killed by simply supplying a liquid containing a sterilizing substance or ions of low concentration or in small quantity once a sufficient sterilization is accomplished first.

The liquid containing a sterilizing substance or ions may be supplied to a toilet at predetermined time intervals only at night. When this method is applied to a toilet that is used only in the day-time and rarely used at night, such as in the office building, in the department store, at the station, at the exhibition site, in the tourist facilities, or in the vehicle running only in the day-time, such a situation can be prevented that bacteria increase in the standing water of the toilet and urease increases and sticks to the surface of the toilet at night or when the toilet is not used, so that the deposition of uric stone can be prevented and one of the causes of the stench can be prevented. Furthermore, the liquid containing a sterilizing substance or ions or the like can be saved since the liquid is supplied at intervals.

In the above case, it is preferable to renew the standing water of the toilet by supplying a flush water to the toilet before the liquid containing a sterilizing substance or ions is supplied to the toilet, as described above. It is also possible that the liquid containing a sterilizing substance or ions of high concentration is supplied only first at night while the same liquid of lower concentration is supplied secondly and subsequently.

The liquid containing a sterilizing substance or ions may be supplied to a toilet in case that the toilet is not used for a predetermined period of time after the last use thereof, whereby such a situation can be prevented that bacteria increase in the standing water of the toilet and urease increases and sticks to the surface of the toilet when the toilet is not used, so that the deposition of uric stone is prevented and one of the causes of the stench is also prevented. When the toilet is used relatively frequently, the standing water of the toilet is renewed by a flush every time the toilet is used, or at predetermined time intervals, so that neither bacteria nor urease increases in the standing water of the toilet.

The liquid containing a sterilizing substance or ions may be supplied to a toilet at predetermined time intervals in case that the toilet is not used for a predetermined period of time after the last use thereof, whereby such a situation can be prevented that bacteria increase in the standing water of the toilet and urease increases and sticks to the surface of the toilet when the toilet is not used, so that the deposition of uric stone is prevented and one of the causes of the stench is also prevented. Furthermore, the liquid containing a sterilizing substance or ions or the like can be saved since the liquid is supplied at intervals.

The liquid containing a sterilizing substance or ions may be supplied to a toilet every time the toilet is used, whereby the generation of ammonia can be effectively suppressed, so that the is deposition of uric stone is prevented and one of the causes of the stench can be also prevented, since urine is prevented from remaining in the standing water of the toilet or on the surface of the toilet and, furthermore, neither bacteria nor urease increases there.

The liquid containing a sterilizing substance or ions may be supplied to a toilet just before or just after the end of a flush after use, whereby the sterilizing substance or ions can spread widely over the surface of the toilet that is wet due to the flush operation subsequent to the use of the toilet. Consequently, the surface of the toilet is sterilized effectively and the increase of urease is prevented. Thus the generation of ammonia is effectively suppressed, so that the deposition of uric stone is prevented and one of the causes of the stench is also prevented.

The liquid containing a sterilizing substance or ions may be supplied just after renewing the standing water of a toilet with a flush water. By this method, the liquid containing a sterilizing substance or ions is made to act after the bacteria in the standing water are decreased. Therefore, the surface of the toilet can be sterilized effectively by just a small amount of sterilizing substance and the increase of urease is prevented. Thus the generation of ammonia is effectively suppressed, so that the deposition of uric stone is prevented and one of the causes of the stench is also prevented.

The liquid containing antibacterial metal ions may be retained as a standing water of a toilet only at night. The instantaneous sterilizing power of the antibacterial metal ions is poorer than that of free chlorine or ozone, but the life span of the antibacterial effect is so long that the advantageous effect can be obtained as the action time gets longer. Therefore, when the ions are used in such a manner as being retained in the standing water of the toilet for an adequate period of time, living bacteria can be decreased even by a small quantity of the ions, and the increase of urease is prevented. Thus the Generation of ammonia is effectively suppressed, so that the deposition of uric stone is prevented and one of the causes of the stench is also prevented.

The liquid containing antibacterial metal ions may be retained as a standing water of a toilet in case that the toilet is not used for a predetermined period of time after the last use thereof The instantaneous sterilizing power of the antibacterial metal ions is poorer than that of free chlorine or ozone, but the life span of the antibacterial effect is so long that the advantageous effect can be obtained as the action time gets longer. Therefore, when the ions are used in such a manner as being retained in the standing water of the toilet for an adequate period of time, living bacteria can be decreased even by a small quantity of the ions, and the increase of urease is prevented. Thus the generation of ammonia is effectively suppressed, so that the deposition of uric stone is prevented and one of the causes of the stench is also prevented.

It is preferable to set the concentration of the water containing a free chlorine that is supplied to a toilet at 0.2 $\mu$g/l or above, preferably at 0.02 mg/l or above, whereby the standing water of the toilet and the surface of the toilet can be sufficiently sterilized. Consequently, the increase and adhesion of urease due to the action of living bacteria can be effectively suppressed and the increase in pH due to the solution of ammonia can be suppressed, so that the deposition of uric stone is prevented and one of the causes of the stench is also prevented.

The deposition of uric stone occurs by the above-described process as the number of bacteria increases in the standing water of a toilet. The uric stone is porous, and the water tends to stand in the pores, where bacteria can increase rapidly. Herein appears a vicious circle that an environment convenient for the increase of bacteria is caused by the increase of bacteria. This vicious circle, however, can be stopped and a toilet can be maintained in the state without uric stone depositing thereon when the number of bacteria in the standing water of the toilet is maintained under $1 \times 10^4$ CFU/ml. Therefore, in case of supplying a liquid containing a sterilizing substance or ions to a toilet, it is desirable to maintain the number of bacteria in the standing water of the toilet under $1 \times 10^4$ CFU/ml. For achieving this objective number, the liquid containing a sterilizing substance or ions may be supplied to the toilet either constantly or after renewing the standing water of the toilet by the normal flush operation. In case of supplying the liquid containing a sterilizing substance or ions constantly, the above objective number of bacteria can be achieved by setting the free chlorine concentration at 0.2 $\mu$g/l or above. In case of supplying the liquid containing a sterilizing substance or ions to the toilet after renewing the standing water of the toilet by the normal flush operation, the above objective number of bacteria can be achieved by setting the free chlorine concentration 0.02 mg/l or above. In addition, the surface of the toilet can be also cleansed sufficiently under the above-described condition, since it is in the standing water of a toilet that the number of bacteria is largest, and if a liquid containing a sterilizing substance or ions is supplied to the toilet so that the number of bacteria in the standing water can be maintained under the objective number, then it naturally results that the object is also achieved on the surface of the toilet where the number of bacteria is smaller than that in the standing water of the toilet.

The above objective number of bacteria can be also achieved when a liquid containing a sterilizing substance or ions is supplied in case that a toilet is not used for a predetermined period of time after the flush operation subsequent to the last use thereof and the liquid containing a sterilizing substance or ions that is supplied first after the above period is a water containing 0.1 mg/l or more of free chlorine.

The above objective number of bacteria can be also achieved when a liquid containing a sterilizing substance or ions is supplied only at night and the liquid containing a sterilizing substance or ions that is supplied first at night is a water containing 0.1 mg/l or more of free chlorine.

By the conventional flush operation subsequent to a use of a toilet, more than 99% of the standing water in the trap of the toilet is renewed. But the conventional flush operation does not perform sterilization. Therefore, the bacteria existing on the surface of the toilet or in the standing water of the toilet gradually increase. For example, in a toilet in the office building, when the number of bacteria is lowered to zero by supplying a water containing free chlorine at 3 a.m. on the previous day, whereafter only normal flush operations are carried out until 10 p.m. while the toilet is ordinarily used; then the number of bacteria in the standing water increases to the maximum value of about $1 \times 10^3$ CFU/ml as the time passes. This shows that the number of bacteria increases while the toilet is used relatively frequently, so that the number is maximized at the time of the first flushing after the toilet is used last. Then, therefore, the water containing free chlorine having somewhat high concentration of 0.1 mg/l or above is supplied to sterilize the toilet sufficiently. After that, since the increasing speed of bacteria is slow while the toilet is not used, the concentration of the water containing free chlorine can be lowered. The above-described method can reduce the electric power consumed for the electrolysis and also make the life span of the electrode longer.

BRIEF EXPLANATION OF THE DRAWING

The patent or application file contains at least one drawing executed in color. Copies of this patent of patent applecation publecation with color drawings(s) will be provided by the Office upon requext and payment of the necessary fee.

FIG. 19 illustrates the appearances of the stain on toilet bowls which were normally used; wherein (a) is the appearance after two weeks, and (b) is the appearance after four weeks.

FIG. 20 shows a constitution of an experiment wherein a toilet bowl being used normally was cleansed by the water containing free chlorine twice a day.

FIG. 21 shows an appearance of the stain on the toilet bowl observed in the experiment of FIG. 20 after four weeks.

Figure 1:
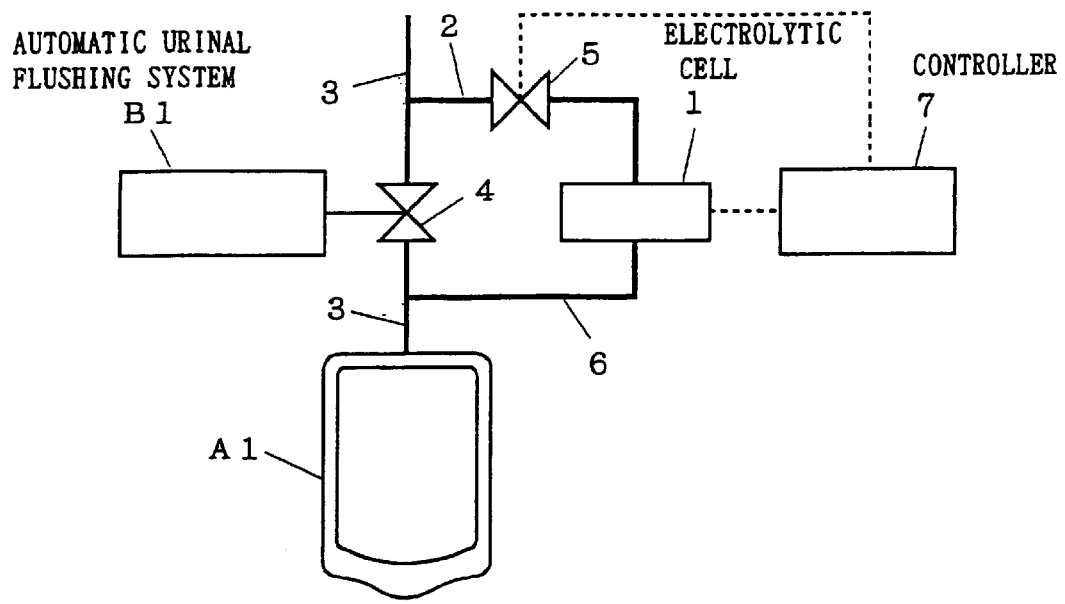
FIG. 1 shows a machinery structure of a system for cleansing a urinal comprising an electrolytic cell provided parallel to an existing flush water supply line.

Table 1 sets forth testing conditions for six urinals tested for bacteria levels as described in the section below entitled "Embodiment 1."

Table 2 sets forth the bacteria levels at specified times for each of the six urinals tested in the section below entitled "Embodiment 1."

Table 3 sets forth the testing conditions for four urinals tested for bacteria levels as described in the section below entitled "Embodiment 2."

Table 4 sets forth the bacteria levels found in each of the four urinals in the section below entitled "Embodiment 2."

Table 5 sets forth the testing conditions for six urinals tested for bacteria levels as described in the section below entitled "Embodiment 4."

Table 6 sets forth the bacteria levels at specified times for each of the six urinals tested in the section below entitled "Embodiment 4."

Table 7 sets forth the bacteria levels, over time, according to free chlorine concentration in the sterilizing water, as described in the section below entitled "Embodiment 8."

BEST MODE FOR CARRYING OUT THE INVENTION

The detailed constitution of the present invention is described in the following.

The urease-carrying bacteria include any bacterium that holds urease inside its body. Basically, all the normal bacteria are included therein, among which it is bacillus that is most outstandingly found in the toilet.

When the surface of a toilet is to be sterilized, for example, the following methods are available as a process of sterilization: to heat the surface of the toilet; to provide a device for irradiating ultraviolet on the surface of the toilet and sterilize the same by ultraviolet; to use a chemical process; and to reform the material composing the surface of the toilet.

When the strainer or the trap of a toilet which contacts the standing water of the toilet is to be sterilized, the following methods are available: to heat; to provide a device for irradiating ultraviolet on the surface of the trap and sterilize the same by ultraviolet; to use a chemical process; and to reform the material composing the surface of the trap or the like.

In the method of sterilizing the surface of a toilet by heat, basically a heater is provided on the surface of the toilet to heat the same. It is preferable that a transparent electrode is disposed on the surface of the glaze layer not to damage the design of the toilet that the glaze presents. For example, tin oxide electrode can be suitably used as a transparent electrode.

In the above case, the transparent electrode can be obtained, for example, by spreading tin oxide on the glaze layer, then heating and fixing it at the temperature where the glaze softens, or by plastering a transparent sheet electrode on the glaze layer.

The strainer or the trap can be also sterilized by the same method.

In the method of sterilizing the surface of a toilet by ultraviolet, basically a device for irradiating ultraviolet is provided on the surface of the toilet to irradiate ultraviolet. A sterilizing lamp for providing rays having a wavelength of about 250 nm can be preferably used as a device for irradiating ultraviolet, since it has a sterilizing effect even at relatively weak illuminance. The device for irradiating ultraviolet may be preferably a panel-shaped device, since it occupies little space, does not damage the external design, and can be easily fixed by plaster or adhesive, etc. In view of safety, it is preferable to provide a controller that checks the sterilizing operation when the toilet is being used. When provided on the urinal, the device for irradiating ultraviolet may be provided on the rim or the flushing portion, whereby the degree of safety is enhanced, since the ultraviolet irradiated by the erroneous operation of the device is prevented from coming directly into the eyes of the users.

The strainer or the trap can be also sterilized by the same method.

In the method of sterilizing the surface of a toilet by ultraviolet, it is furthermore preferable to fix a photocatalyst on the surface of the toilet, since even a weak ultraviolet of sun light, fluorescent light and interior illumination, etc., can cause sterilization thereby. For fixing the photocatalyst on the surface of the toilet, the following methods are available: to spread the photocatalyst on the glaze layer, then fix it at the temperature where the glaze softens; to mix the photocatalyst with light resistant material, such as inorganic binder, and fix them together; and to form a photocatalyst sheet and plaster it. In any of these methods, the photocatalyst fixation layer may be preferably transparent not to damage the design that the glaze presents. This condition can be met by defining the size of the particles and the gas cavities in the photocatalyst fixation layer, or the thickness of the fixation layer, less than a half of the wavelength of visible light, i.e., 0.2 $\mu$m or below. It is preferable to add, as a photocatalyst, not only photoserniconductive substance but also a metal that captures the electron when the electron and the positive hole are generated in the photosemiconductive substance by the photon, whereby the annihilation of positive holes resulting from their recombination with electrons can be suppressed and more sterilizing power can be obtained, since the sterilization is mainly caused by the active oxygen resulting from the reaction of positive hole and hydroxide ion. Platinum, gold, silver and copper are examples of the metals that can capture the electron, among which silver and copper are more preferable, since they have their own independent sterilizing power due to the oligomer effect and can keep the antibacterial effect even in the dark.

In case of sterilizing a urinal, when the device for irradiating ultraviolet is provided at the rim or the flushing portion and the photocatalyst fixation layer is provided in opposition thereto, the ultraviolet having more illuminance than interior light can be irradiated on the surface of the urinal, so that the sterilizing power can be enhanced. Furthermore, the degree of safety is enhanced thereby, since the ultraviolet irradiated by erroneous operation of the device is prevented from coming directly into the eyes of users.

The strainer or the trap can be also sterilized by the same method using a device for irradiating ultraviolet.

The method of sterilizing the surface of a toilet by a chemical process is basically a method wherein a sterilizing substance is contacted with the surface of the toilet. The followings are examples of such methods: to provide means for supplying a sterilizing liquid in the upstream pipe of a toilet and supply the liquid to the toilet properly; to spray a sterilizing liquid onto the surface of a toilet; and to let a sterilizing gas blow onto the surface of a toilet.

The method wherein means for supplying a sterilizing liquid is provided in the upstream pipe of a toilet and the liquid is supplied to the toilet properly is, in detail, a method in which a tank for holding a sterilizing liquid, or a device for producing a sterilizing liquid, such as an electrolytic cell, is provided in the upstream of the toilet, and the liquid is supplied properly to the toilet to prevent the increase of living bacteria.

The followings are examples of the sterilizing substances: free chlorine, antibacterial metal or its ions, ozone, ozone-water, bound chlorine, antiseptic solution of organochlorine, antiseptic solution of organophosphoric acid, peroxocarbon ions or their salts, antiseptic solution of alcohol.

Among these substances, free chlorine, bound chlorine, ozone and ozone-water are more preferable than antiseptic solution of organochlorine or antiseptic solution of organophospheric acid, etc., since the life span of the former substances in water is at most several weeks, which is short enough not to cause a water pollution or the like.

Free chlorine, bound chlorine and ozone-water can be produced by simply electrolyzing such a water as supplied by a tap water line, therefore less maintenance work is required.

The antibacterial metal or its ions lose their antibacterial effect once it is enclosed by organic substances or relatively large negative ions, since the size of an atom or ion of the metal is small. However, the advantage still exists in that they hold the action for a longer time than free chlorine, bound chlorine, ozone or ozone-water, etc. Accordingly, in case of sterilizing a standing water, high sterilizing effect can be preferably maintained for a considerably long time without the additional supply of sterilizing ingredient by simply disposing a substance containing the antibacterial metal or its ions in a trap.

The method of sterilization by reforming the material composing the surface of a toilet is basically such a method in which a sterilizing substance is spread on or mixed in the surface of the toilet.

For facilitating the production of a toilet, it is preferable that the sterilizing substance to be spread on or mixed in the surface of a toilet is a heat resistant substance. The substance containing antibacterial metal or its ions can be suitably used here.

The substance containing antibacterial metal or its ions are such things as the antibacterial metal or its ions themselves, a compound containing antibacterial metal or its ions, or a substance holding antibacterial metal or its ions.

Silver, copper and zinc are examples of the antibacterial metal. The following substances are available for holding antibacterial metal or its ions: glaze, glass, dissolved glass, layer silicate, layer aluminosilicate, apatite, calcium phosphate, aluminum phosphate, zeolite, zinc oxide, iron oxide, titan oxide, etc.

Among these substances, glaze, glass, apatite, calcium phosphate, aluminum phosphate, zinc oxide, iron oxide and titan oxide are especially preferable, since they have heat resistance even at the firing temperature of the sanitary wares.

The process of removing urease from a toilet is a process whereby urease and urease-carrying bacteria on the surface of the toilet or in the standing water of the toilet are removed from the toilet. In detail, the following methods are available: to wash urease out of the toilet with such as a water, a flush water, a sterilizing liquid, etc.; to decompose urease by chemical or thermal process, etc. The method wherein urease is washed out of the toilet with such as a water, a flush water or a sterilizing liquid, is the more preferable, since urease is a considerably stable substance as an enzyme.

The process of inhibiting the enzymatic activity of urease is a process of inhibiting or weakening the action of urease as an enzyme. In detail, a substance that inhibits the enzymatic activity of urease is contacted with urease or urease-carrying bacteria that exist on the surface of the toilet or in the standing water of the toilet.

The followings are available as the substance for inhibiting the enzymatic activity of urease: a substance containing heavy metal, halogen, boric acid, quinone, hydrogen peroxide, etc.

In order to contact the substance for inhibiting the enzymatic activity of urease with the urease or the urease-carrying bacteria that exist on the surface of the toilet or in the standing water of the toilet, a liquid containing heavy metal salts, halogen, boric acid, quinone, hydrogen peroxide, etc., may be supplied to the toilet; or, heavy metal salts, halogenide, borate, etc., may be fixed on the surface of the toilet or on the surface of the trap or the like so that the substance can contact with urease existing with the adhering bacteria.

A solid matter to which heavy metal salts, halogenide, borate, etc., is fixed may be placed in the trap of the toilet so that the substance can contact with urease existing with bacteria in the standing water.

The process of killing bacteria together with inhibiting the enzymatic activity of urease is a process whereby bacteria are killed and the enzymatic activity of urease is inhibited or weakened, simultaneously. In detail, a substance that not only kills bacteria but also inhibits or weakens the enzymatic activity of urease, is contacted with the urease-carrying bacteria that exist on the surface of the toilet or in the standing water of the toilet.

A substance containing silver, copper, zinc or their ions, free chlorine, bound chlorine, etc., are available as a substance that not only kills bacteria but also inhibits or weakens the enzymatic activity of urease.

In order to contact the substance that not only kills bacteria but also inhibits or weakens the enzymatic activity of urease with the urease or the urease-canying bacteria that exist on the surface of the toilet or in the standing water of the toilet, a liquid that contains the substance containing silver, copper, zinc or their ions, free chlorine, bound chlorine, etc., may be supplied to the toilet, or the substance containing silver, copper, zinc or their ions may be fixed on the surface of the toilet or on the surface of the trap or the like so that the substance can contact with urease accompanying the adhering bacteria.

In case of sterilizing a trap or the like, a solid matter to which a substance containing silver, copper, zinc or their ions are fixed, may be placed therein so that the substance can contact with urease existing with bacteria in the standing water.

The free chlorine includes hypochlorous acid and its ions. The bound chlorine includes such compounds as monochloramine, dichloramine and trichloramine. It is known that monochloramine and dichloramine have sterilizing power.

In case of using a liquid containing free chlorine, it is preferable to electrolyze and supply a water containing chlorine, such as tap water, recycled water, well-water and industrial water. It is not good to store the liquid containing free chlorine, since the quantity of free chlorine gradually decreases while the liquid is left unused.

The electrolyzing device may comprise a diaphragm between anode and cathode to extract alkaline water and acid water, respectively, whereby only the acid water is supplied to the toilet. The device may otherwise comprise no diaphragm, whereby all the liquid produced by the electrolysis is supplied to the toilet.

The method using diaphragm-less device to electrolyze all the liquid and supply it to the toilet can be preferably applied to such a place where plenty of flush water is required at a time, for example, to the toilet unit comprising a series of toilets.

The method of extracting alkaline water and acid water separately by the device having a diaphragm between anode and cathode, on the contrary, can be used for plurality of purposes in such a way that the device is provided in the upstream pipe of the tap water line at a general residence, and the alkaline water is used for drinking while the acid water containing free chlorine is supplied to the toilet.

The free chlorine takes a form of a hypochlorous acid (HClO), which has more sterilizing power, in the acid solution.

In the method of electrolyzing the water containing chlorine ions, at least the anode of the electrolyzing device should be a chlorine-forming electrode in order to make the chlorine formation activated more than the oxygen formation and improving the efficiency of producing free chlorine.

The chlorine-forming electrode is an electrode that can induce the chlorine formation, said electrode basically composed of either a conductive base material holding a catalyst for chlorine formation or a conductive material made of a catalyst for chlorine formation.

The electrodes can be classified into some groups according to the choice of the catalyst for chlorine formation: iron group such as ferrite, palladium group, ruthenium group, iridium group, platinum group, ruthenium-tin group, palladium-platinum group, iridium-platinum group, ruthenium-platinum group, iridium-platinum-tantalum group, etc.

The electrode consisting of a conductive base material holding a catalyst for chlorine formation is advantageous in respect of production cost, since cheap materials such as titan or stainless steel are available to build a base structure.

When tap water, which ordinarily contains 3 to 40 ppm of chlorine ions at most, is used, it is especially important to improve the efficiency of producing free chlorine in order to kill urease-carrying bacteria sufficiently. In this respect, electrodes of iridium group, iridium-platinum group and iridium-platinum-tantalum group, etc., are preferable.

When the electrode consisting of a conductive base material holding a catalyst for chlorine formation is used, it is preferable that platinum is contained in the catalyst to make the life span of the electrode longer, since the catalyst that contains platinum can be fixed to the base material so securely that the peeling hardly occurs.

The voltage applied between the electrodes in the electrolytic cell may be either of DC and AC voltages. When AC voltage is applied between the electrodes, it is preferable to use chlorine-forming electrodes at both anode and cathode sides.

In any case other than above, basically any conductive material can be used as cathode electrode. For example, it is advantageous in respect of production cost to use such cheap materials as iron or stainless steel.

Various systems for cleansing a toilet according to the present invention are described in the following. The description mainly relates to the systems for cleansing a urinal, and of course yellowish stain of a toilet bowl can be prevented by the same cleansing methods and systems.

FIG. 1 shows an embodiment of the system for cleansing a urinal according to the present invention. The system comprises a continuous electrolytic cell 1 having at least a pair of electrodes, a passage formed between the electrodes and an inlet and an outlet both leading to the passage. The continuous electrolytic cell 1 is connected by a first branch 2 with a flush water supply line 3 at an upstream of a water supply valve 4 consisting of a flush valve or the like. An on/off valve 5 consisting of a solenoid valve or the like is provided in the first branch 2. The continuous electrolytic cell 1 is connected by a second branch 6 with the flush water supply line 3 at a downstream of the water supply valve 4. The flush water supply line 3 to which the second branch 6 is connected leads to a urinal A1. The electrolytic cell 1 and the on/off valve 5 are connected with a controller 7 having a timer, respectively. The water supply valve 4 is connected with a known automatic flushing system B1.

In the present system for cleansing a urinal, the controller 7 opens the on/off valve 5 properly as instructed by the timer, whereafter tap water flows from the flush water supply line 3 at an upstream of the water supply valve 4, via the first branch 2, into the passage formed between the electrodes of the continuous electrolytic cell 1. On opening the on/off valve 5, or with a delay after that, the controller 7 applies voltage between the electrodes, whereby the tap water flowing through the passage formed between the electrodes of the continuous electrolytic cell 1 is electrolyzed and the water containing free chlorine is produced. The water containing free chlorine produced flows through the second branch 6 into the flush water supply line 3 at the downstream of the water supply valve 4, and is supplied to the urinal A1, whereby the urinal A1 is properly sterilized and urease carried by bacteria is removed from the urinal A1 together with the bacteria. Thus the precipitation of uric stone and the formation of the stain on the urinal A1 are prevented.

Apart from the operation of the present system for cleansing a urinal, tap water is supplied to the urinal A1 by the operation of the automatic flushing system B1, or by manual operation, every time of use, whereby the surface of the urinal A1 is flushed and the standing water in the trap of the urinal is renewed.

In the present system for cleansing a urinal, the water containing free chlorine that is used for cleansing a urinal is produced by electrolyzing tap water, therefore it requires less maintenance work and is safer to users than the conventional flushing system using chemicals mixed with the flush water.

In the present system for cleansing a urinal, the controller 7 may open the on/off valve 5 at predetermined time intervals as instructed by the timer and apply voltage between the electrodes on opening the on/off valve 5, or with a delay after that, so that the tap water flowing through the passage formed between the electrodes of the continuous electrolytic cell 1 is electrolyzed and the water containing free chlorine is produced there. By this method, the bacteria are killed and removed at intervals, therefore the increase and adhesion of living bacteria coming from the ambient air or from other sources can be effectively prevented. Consequently, the increase and adhesion of urease due to the action of living bacteria are effectively suppressed and the increase in pH due to the solution of ammonia is suppressed, so that the deposition of uric stone is prevented and one of the causes of the stench is also prevented. Since the electrolysis occurs only at intervals, the life span of the electrodes of the electrolytic cell can be longer and the necessity for maintenance work can be reduced. Furthermore, the present system can save resource and energy, since it consumes less water and electricity than a system wherein water is supplied at all times.

Figure 26:
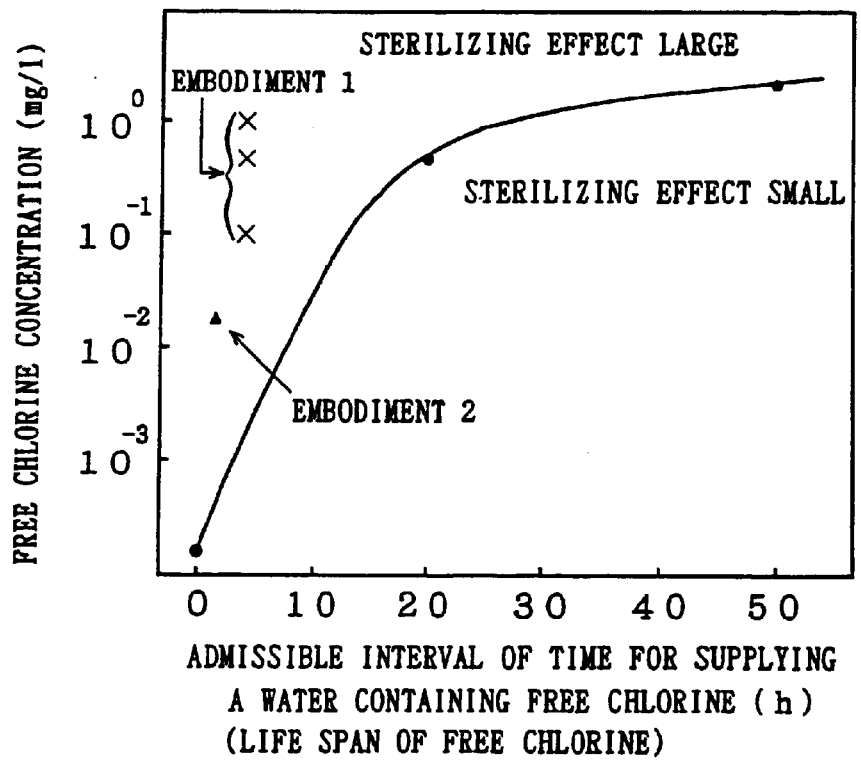
FIG. 26 shows a relationship between an interval of time for applying the water containing free chlorine and the free chlorine concentration required to obtain a sufficient sterilizing effect at the interval of time.

When the water containing free chlorine is supplied to the urinal at predetermined time intervals, the interval of time may be preferably shorter than the time in which free chlorine of a predetermined concentration is exhausted, since bacteria coming from the outside cannot be killed after the free chlorine is exhausted, which leads to the increase of bacteria and further to the increase of urease. The full line in FIG. 26 shows the relationship between a time interval at which the water containing free chlorine is supplied and the concentration of free chlorine. The interval of time at which the water containing free chlorine of a predetermined concentration is supplied to the urinal may be preferably on the left side of the full line in the figure, i.e., at shorter time intervals.

In the present system for cleansing a urinal, the controller 7 may open the on/off valve 5 only at night as instructed by the timer and apply voltage between the electrodes on opening the on/off valve 5, or with a delay after that, so that the tap water flowing through the passage formed between the electrodes of the continuous electrolytic cell 1 is electrolyzed and the water containing free chlorine is produced there. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal at predetermined time intervals, or every time of use, by the operation of the automatic flushing system B1, or by manual operation, apart from the operation of the present system for cleansing a urinal, whereby the surface of the urinal A1 is flushed and the standing water in the trap of the urinal is renewed.

In the above case, the controller 7 may open the on/off valve 5 only at night and at predetermined time intervals as instructed by the timer and apply voltage between the electrodes on opening the on/off valve 5, or with a delay after that, so that the tap water flowing through the passage formed between the electrodes of the continuous electrolytic cell 1 is electrolyzed and the water containing free chlorine is produced there. This method is preferable in that the life span of the electrode of the electrolytic cell can be longer and the necessity for maintenance work can be reduced. Furthermore, this method is preferable in respect of saving resource and energy, since it consumes less water and electricity than a method whereby water is supplied at all times.

The present system for cleansing a urinal may also take a constitution as follows: the controller 7 is connected with the automatic flushing system B1 so that the controller 7 sends the operation signal to the automatic flushing system B1 to start a normal flush operation; in case of supplying the water containing free chlorine only at night, as shown above, the controller 7 first sends the signal to the automatic flushing system B1 to supply the flush water to the urinal, whereby the standing water of the urinal is renewed (almost 99% of the standing water is freshly renewed thereby) and most of the bacteria are removed from the urinal; after that, the controller 7 opens the on/off valve 5, as described above, and at the same time, or with a delay after that, applies voltage between the electrodes, so that the tap water flowing through the passage formed between the electrodes of the continuous electrolytic cell 1 is electrolyzed and the water containing free chlorine is produced there and supplied to the urinal A1; whereby the remaining bacteria are killed fully.

In the present system for cleansing a urinal, the same effect as described above can be also obtained by the following method wherein: the controller 7 is connected with the automatic flushing system B1 so that an operation signal of the system B1 is inputted to the controller 7; the timer of the controller 7 starts clocking on receiving the operation signal of the automatic urinal flushing system B1; in case that the urinal A1 is not used for a predetermined period of time after the last use thereof, i.e., that no operation signal of the automatic flushing system B1 is outputted for the predetermined period of time after the system B1 outputs the operation signal on the last use of the urinal A1, the controller 7 opens the on/off valve 5 as instructed by the timer and applies voltage between the electrodes on opening the on/off valve 5, or with a delay after that, whereby the tap water flowing through the passage formed between the electrodes of the continuous electrolytic cell 1 is electrolyzed and the water containing free chlorine is produced. This method provides the largest effect of saving resource and energy.

In the present system for cleansing a urinal, the controller 7 may be connected with the automatic flushing system B1 so that an operation signal of the system B1 is inputted to the controller 7 and the controller 7, in response to the operation signal of the automatic flushing system B1, opens the on/off valve 5 and applies voltage between the electrodes on opening the on/off valve 5, or with a delay as instructed by the timer, at every flush after use, i.e., every time the urinal A1 is used and the operation signal of the automatic flushing system B1 is outputted, whereby the tap water flowing through the passage formed between the electrodes of the continuous electrolytic cell 1 is electrolyzed and the water containing free chlorine is produced. By this method, the sterilization and the inhibition of the enzymatic activity of urease are accomplished immediately after a user urinates, the generation of ammonia is effectively suppressed, so that the deposition of uric stone is prevented and one of the causes of the stench is also prevented.

Compared with a system whereby water is supplied at all times, the above system is preferable in that the life span of the electrodes of the electrolytic cell can be longer, the necessity for maintenance work can be reduced and resource and energy can be saved since it consumes less water and electricity.

In the present system for cleansing a urinal, the controller 7 may be connected with the automatic flushing system B1 so that an operation signal of the system B1 is inputted to the controller 7; the timer in the controller 7 starts clocking on receiving the operation signal of the automatic flushing system B1; the controller 7 opens the on/off valve 5, as instructed by the timer, just before or just after the end of a flush after use, i.e., with a delay after the output of the operation signal of the automatic flushing system B1 subsequent to the use of the urinal A1; on every opening of the on/off valve 5 the controller 7 applies voltage between the electrodes, whereby the tap water flowing through the passage formed between the electrodes of the continuous electrolytic cell 1 is electrolyzed and the water containing free chlorine is produced. By this method, the water containing free chlorine is supplied to the urinal just before or just after the end of a flush after use, so that the water containing free chlorine can spread widely over the surface of the urinal that is wet due to the flush operation by the automatic flushing system B1. As a result, the surface of the urinal can be sterilized effectively, the increase of urease can be prevented. Thus the generation of ammonia is effectively suppressed, so that the deposition of uric stone is prevented and one of the causes of the stench is also prevented.

In the present system for cleansing a urinal, a flow control valve may be provided in the first branch 2 in place of the on/off valve 5. The controller 7 opens the flow control valve at a predetermined time and adjusts it at a predetermined opening. When the opening of the flow control valve is larger, the concentration of the free chlorine produced by the electrolysis becomes lower since the flow rate of the tap water flowing into the continuous electrolytic cell 1 becomes larger, whereas, when the opening is smaller, the concentration of free chlorine becomes higher since the flow rate of the water becomes smaller. Thus the free chlorine concentration can be controlled by means of flow control by using a flow control valve in place of the on/off valve 5.

Figure 2:
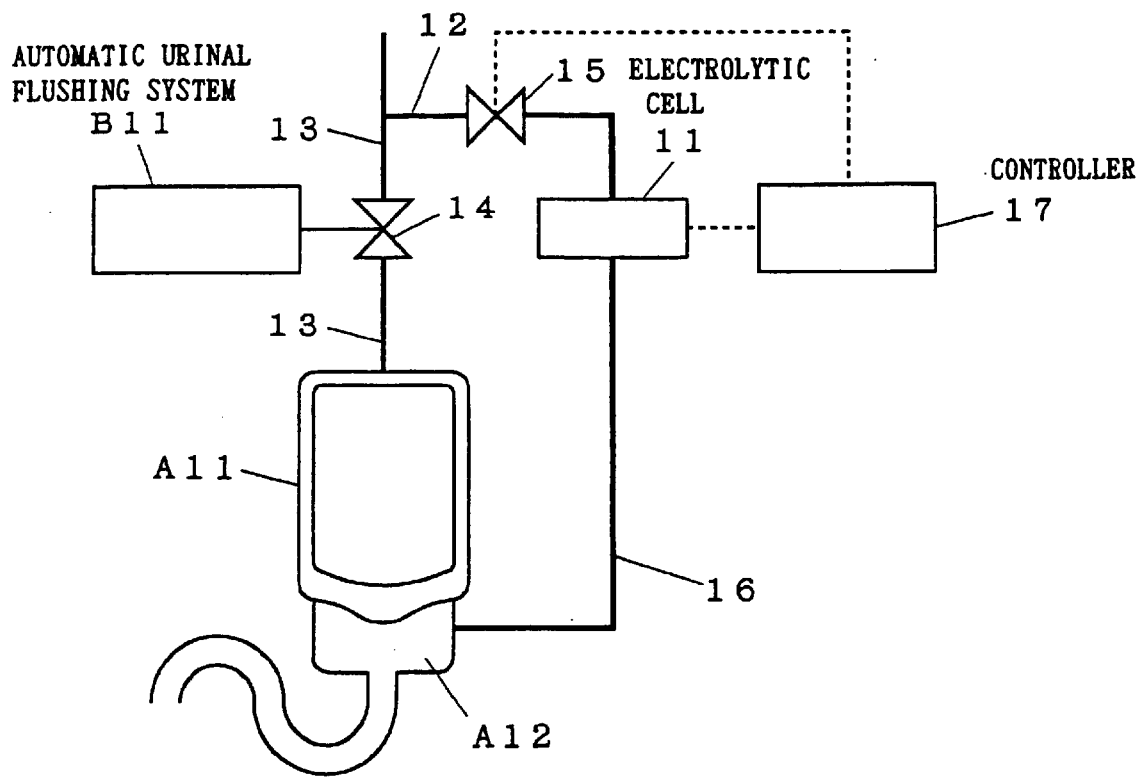
FIG. 2 shows a machinery structure of a system for cleansing a urinal comprising an electrolytic cell provided parallel to an existing flush water supply line, and having a constitution that the water containing free chlorine is supplied to the trap of the urinal.

FIG. 2 shows another embodiment of the system for cleansing a urinal according to the present invention. The present system comprises a continuous electrolytic cell 11 having at least a pair of electrodes, a passage formed between the electrodes and an inlet and an outlet both leading to the passage. The continuous electrolytic cell 11 is connected by a first branch 12 with the flush water supply line 13 at an upstream of a water supply valve 14 consisting of a flush valve or the like. An on/off valve 15 consisting of a solenoid valve or the like is provided in the first branch 12. The continuous electrolytic cell 11 is connected by a second branch 16 with the trap A12 of a urinal. The flush water supply line 13 is connected to the urinal A11. The continuous electrolytic cell 11 and the on/off valve 15 are connected with a controller 17 having a timer, respectively. The water supply valve 14 is connected with a known automatic flushing system B11.

In the present system for cleansing a urinal, the controller 17 opens the on/off valve 15 properly as instructed by the timer, whereafter tap water flows from the flush water supply line 13 at the upstream of the water supply valve 14, via the first branch 12, into the passage formed between the electrodes of the continuous electrolytic cell 11. On opening the on/off valve 15, or with a delay after that, the controller 17 applies voltage between the electrodes, whereby the tap water flowing through the passage formed between the electrodes of the continuous electrolytic cell 11 is electrolyzed and the water containing free chlorine is produced. The water containing free chlorine produced is supplied via the second branch 16 to the trap A12, whereby the standing water of the urinal A11 is properly sterilized and urease carried by bacteria is removed from the urinal A11 together with the bacteria. Thus the precipitation of uric stone and the formation of yellowish stain are prevented at the trap A12 where yellowish stain sticks most outstandingly.

Apart from the operation of the present system for cleansing a urinal, tap water is also supplied to the urinal A11 by the operation of the automatic flushing system B11, or by manual operation, every time of use, whereby the surface of the urinal A11 is flushed and the standing water in the trap A12 is renewed.

In the present system for cleansing a urinal, the water containing free chlorine that is used for cleansing a urinal is produced by electrolyzing tap water, therefore it requires less maintenance work and is safer to users than the conventional flushing system using chemicals mixed with the flush water.

In the present system for cleansing a urinal, the controller 17 may open the on/off valve 15 at predetermined time intervals as instructed by the timer and apply voltage between the electrodes on opening the on/off valve 15, or with a delay after that, so that the tap water flowing through the passage formed between the electrodes of the continuous electrolytic cell 11 is electrolyzed and the water containing free chlorine is produced. By this method, the living bacteria are killed and removed at intervals, therefore the increase and adhesion of living bacteria coming from the ambient air or from other sources into the standing water in the trap A12 can be effectively prevented. Consequently, the increase and adhesion of urease due to the action of living bacteria can be effectively suppressed and the increase in pH due to the solution of ammonia is suppressed, so that the deposition of uric stone is prevented and one of the causes of the stench is also prevented. Since the electrolysis occurs only at intervals, the life span of the electrodes of the electrolytic cell can be longer and the necessity for maintenance work can be reduced. Furthermore, the present system can save resource and energy, since it consumes less water and electricity than a system whereby water is supplied at all times.

In the present system for cleansing a urinal, the controller 17 may open the on/off valve 15 only at night as instructed by the timer and apply voltage between the electrodes on opening the on/off valve 15, or with a delay after that, so that the tap water flowing through the passage formed between the electrodes of the continuous electrolytic cell 11 is electrolyzed and the water containing free chlorine is produced. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal at predetermined time intervals, or every time of use, by the operation of the automatic flushing system B11, or by manual operation, apart from the operation of the present system for cleansing a urinal, whereby the surface of the urinal A11 is flushed and the standing water in the trap A12 is renewed.

In the above case, the controller 17 may open the on/off valve 15 only at night and at predetermined time intervals as instructed by the timer and apply voltage between the electrodes on opening the on/off valve 15, or with a delay after that, so that the tap water flowing through the passage formed between the electrodes of the continuous electrolytic cell 11 is electrolyzed and the water containing free chlorine is produced. By this system the life span of the electrodes of the electrolytic cell can be longer and the necessity for maintenance work can be reduced. Furthermore, this system is preferable in respect of saving resource and energy, since it consumes less water and electricity than a system whereby water is supplied at all times.

The present system for cleansing a urinal may also take a constitution as follows: the controller 17 is connected with the automatic flushing system B11 so that the controller 17 may send the operation signal to the automatic flushing system B11 to start a normal flush operation; in case of supplying the water containing free chlorine only at night, as shown above, the controller 17 first sends the signal to the automatic flushing system B11 to supply the flush water to the urinal, whereby the standing water of the urinal is renewed (almost 99% of the standing water is freshly renewed thereby) and most of the bacteria are removed from the urinal; after that, the controller 17 opens the on/off valve 15, as described above, and at the same time, or with a delay after that, applies voltage between the electrodes, so that the tap water flowing through the passage formed between the electrodes of the continuous electrolytic cell 11 is electrolyzed and the water containing free chlorine is produced there and supplied to the trap A122; whereby the remaining bacteria are killed fully.

In the present system for cleansing a urinal, the same effect as described above can be also obtained by the following method wherein: the controller 17 is connected with the automatic flushing system B11 so that an operation signal of the system B11 is inputted to the controller 17; the timer of the controller 17 starts clocking on receiving the operation signal of the automatic flushing system B11; in case that the urinal A11 is not used for a predetermined period of time after the last use thereof, i.e., that no operation signal of the automatic flushing system B11 is outputted for the predetermined period of time after the system B11 outputs the operation signal on the last use of the urinal A11, the controller 17 opens the on/off valve 15 as instructed by the timer and applies voltage between the electrodes on opening the on/off valve 15, or with a delay after that, whereby the tap water flowing through the passage formed between the electrodes of the continuous electrolytic cell 11 is electrolyzed and the water containing free chlorine is produced. This method provides the largest effect of saving resource and energy.

In the present system for cleansing a urinal, the controller 17 may be connected with the automatic flushing system B11 so that an operation signal of the system B11 is inputted to the controller 17 and the controller 17, in response to the operation signal of the automatic flushing system B11, opens the on/off valve 15 and applies voltage between the electrodes on opening the on/off valve 15, or with a delay as instructed by the timer, at every flush after use, i.e., every time the urinal A11 is used and the operation signal of the automatic flushing system B11 is outputted, whereby the tap water flowing through the passage formed between the electrodes of the continuous electrolytic cell 11 is electrolyzed and the water containing free chlorine is produced. By this method, the sterilization and the inhibition of the enzymatic activity of urease are accomplished immediately after a user urinates, the generation of ammonia is effectively suppressed, so that the deposition of uric stone is prevented and one of the causes of the stench is also prevented.

Compared with a system whereby water is supplied at all times, the above system is preferable in that the life span of the electrodes of the electrolytic cell can be longer, the necessity for maintenance work can be reduced and the resource and energy can be saved since it consumes less water and electricity.

In the present system for cleansing a urinal, a flow control valve may be provided in the first branch 12 in place of the on/off valve 15. The controller 17 may open the flow control valve at a predetermined time and adjust it at a predetermined opening. When the opening of the flow control valve is larger, the concentration of the free chlorine produced by the electrolysis becomes lower since the flow rate of the tap water flowing into the continuous electrolytic cell 11 becomes larger, whereas, when the opening is smaller, the concentration of free chlorine becomes higher since the flow rate of the water becomes smaller. Thus the free chlorine concentration can be regulated by means of flow control by using a flow control valve in place of the on/off valve 15.

Figure 3:
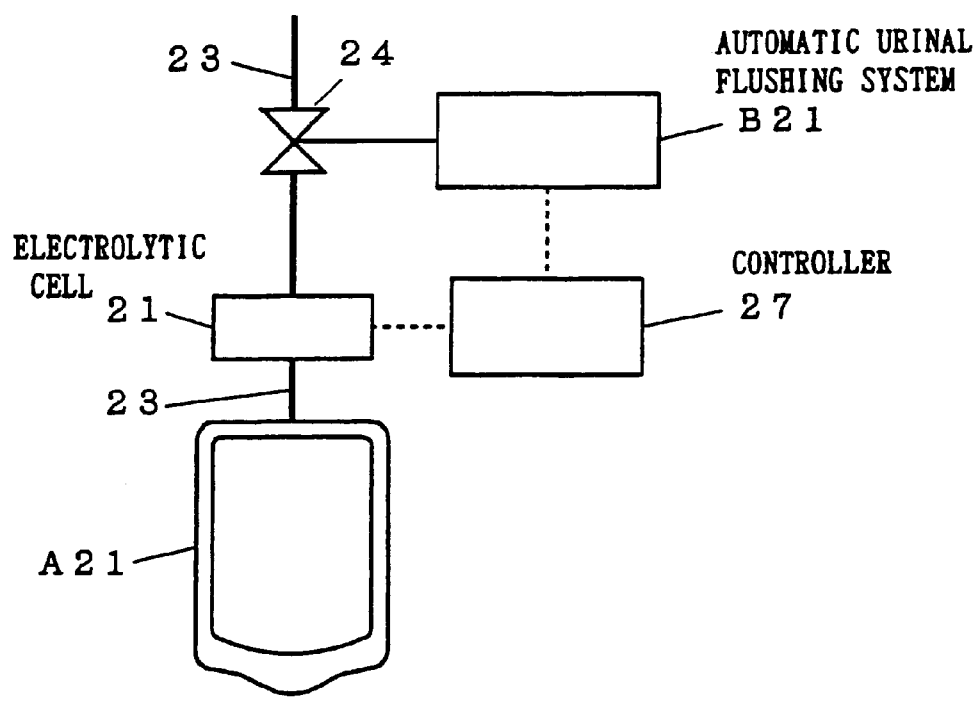
FIG. 3 shows a machinery structure of a system for cleansing a urinal comprising an electrolytic cell provided in an existing flush water supply line.

FIG. 3 shows another embodiment of the system for cleansing a urinal according to the present invention. The present system comprises a continuous electrolytic cell 21 having at least a pair of electrodes, a passage formed between the electrodes and an inlet and an outlet both leading to the passage. The continuous electrolytic cell 21 is provided in a flush water supply line 23 at a downstream of a water supply valve 24 consisting of a flush valve or the like. A controller 27 is connected with the continuous electrolytic cell 21. The water supply valve 24 is connected with a known automatic flushing system B21. The flush water supply line 23 is connected to a urinal A21.

In the present system for cleansing a urinal, the water supply valve 24 is opened by the operation of the automatic flushing system B21, whereby tap water flows via the flush water supply line 23 into the passage formed between the electrodes of the continuous electrolytic cell 21. The control signal sent to the water supply valve 24 is also sent to the controller 27 by the automatic flushing system B21. The controller 27, on receiving the signal, applies voltage between the electrodes, whereby the tap water flowing through the passage formed between the electrodes of the continuous electrolytic cell 21 is electrolyzed. The water containing free chlorine produced by the electrolysis is supplied via the flush water supply line 23 to the urinal A21.

By the above method, the water containing free chlorine is supplied to the urinal every time the urinal A21 is used, whereby the sterilization and the inhibition of the enzymatic activity of urease can be accomplished immediately after a user urinates and the generation of ammonia can be effectively suppressed, so that the deposition of uric stone is prevented and one of the causes of the stench is also prevented.

The present system for cleansing a urinal also requires less maintenance work and is safer to users than the conventional flushing system using chemicals mixed with the flush water.

In the present system for cleansing a urinal, furthermore, a timer may be provided to the controller 27 and the controller 27, after receiving a control signal sent to the water supply valve 24 by the automatic flushing system B21, may apply voltage between the electrodes just before the end of the period when the water supply valve 24 is open, whereby the tap water flowing through the passage formed between the electrodes of the continuous electrolytic cell 21 is electrolyzed.

By the above system, the water containing free chlorine is supplied to the urinal just before or just after the end of a flush after use, so that the water containing free chlorine can spread widely over the surface of the urinal that is still wet due to the flush operation by the automatic flushing system B21. As a result, the surface of the urinal can be sterilized effectively and the increase of urease is prevented, so that the generation of ammonia is suppressed effectively, the deposition of uric stone is prevented and one of the causes of the stench is also prevented.

All the systems for cleansing a urinal shown in the above embodiments of FIGS. 1 to 3 comprise continuous electrolytic cells. The continuous electrolytic cell may take any structure, but it is required that the unit can electrolyze a water containing chlorine ions in the flowing state, not in the standing state, efficiently. It is further preferable, in view of saving energy, to use a diaphragm-less electrolytic cell having no diaphragm between the electrodes. By the diaphragm-less electrolytic cell, the electric power required for electrolysis can be reduced by setting the distance between the electrodes smaller. Furthermore, the diaphragm-less electrolytic cell can be manufactured in small, compact size easily, since the distance between the electrodes can be set smaller.

As an electrolytic cell having characteristics described above, for example, an electrolytic cell employing the electrolyzing method disclosed in the international patent application No. PCT/JP95/01036 can be preferably used. In the method, a water passage is formed between at least a pair of plate electrodes with a distance of 0.2 mm or above and direct current of 300 to 1100 A/m$^2$ is discharged between the plate electrodes, preferably the distance between the electrodes is 0.4 mm or more and the direct current is set at 400 to 600 A/m$^2$.

Figure 4:
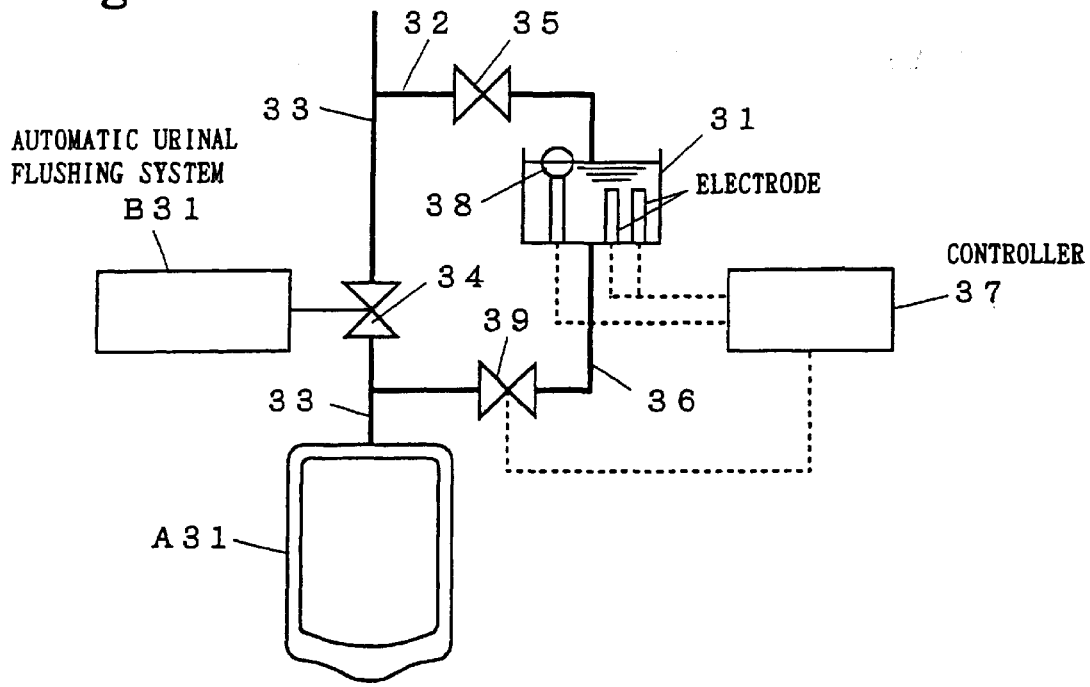
FIG. 4 shows a machinery structure of a system for cleansing a urinal comprising a tank-type electrolytic cell provided parallel to an existing flush water supply line, and having a constitution that an on/off valve for passing and stopping the water containing free chlorine flowing from the tank-type electrolytic cell is opened and closed as instructed by a controller.

FIG. 4 shows another embodiment of the system for cleansing a urinal according to the present invention. The present system comprises a tank-type electrolytic cell 31 having at least a pair of electrodes and a float sensor 38. The tank-type electrolytic cell 31 is connected by a first branch 32 with a flush water supply line 33 at an upstream of a water supply valve 34 consisting of a flush valve or the like. A flow control valve 35 is provided in the first branch 32. The tank-type electrolytic cell 31 is connected by a second branch 36 with the flush water supply line 33 at a downstream of the water supply valve 34. An on/off valve 39 is provided in the second branch 36. The flush water supply line 33 to which the second branch 36 is connected leads to the urinal A31. The electrodes and the float sensor 38 of the tank-type electrolytic cell 31 and the on/off valve 39 are connected with a controller 37.

In the present system for cleansing a urinal, tap water constantly flows at a small flow rate from the flush water supply line 33 at the upstream of the water supply valve 34, via the first branch 32 and the flow control valve 35, into the tank-type electrolytic cell 31. The water level in the tank-type electrolytic cell 31 is detected by the float sensor 38. When the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed. When the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31.

The time when the electrodes get submerged, and the time when the water in the tank-type electrolytic cell reaches the predetermined level, may be detected either by measuring the water level directly with the float sensor, as shown above, or by measuring the elapsing time from a time when the on/off valve is opened.

Apart from the operation of the present system for cleansing a urinal, tap water is also supplied to the urinal A31 by the operation of the automatic flushing system B31, or by manual operation, every time of use, whereby the surface of the urinal A31 is flushed and the standing water in the trap of the urinal is renewed.

The present system for cleansing a urinal, similar to the systems shown in FIGS. 1–3, requires less maintenance work and is safer to users than the conventional flushing system using chemicals mixed with the flush water.

By the above system, the water containing free chlorine can be supplied to the urinal A31 at predetermined time intervals by setting the flow rate of the flow control valve 35 properly. Consequently, the increase and adhesion of urease due to the action of living bacteria can be effectively suppressed and the increase in pH due to the solution of ammonia is suppressed, so that the deposition of uric stone is prevented and one of the causes of the stench is also prevented. Since the electrolysis is conducted only at intervals, the life span of the electrodes of the electrolytic cell can be longer and the necessity for maintenance work can be reduced. Furthermore, the present system can save resource and energy since it consumes less water and electricity than a system whereby water is supplied at all times.

The system for cleansing a urinal shown in FIG. 4 may also take a constitution as follows: the flow control valve 35 is connected with the controller 37; a timer is provided in the controller 37; the controller 37 opens the flow control valve 35 properly and adjusts it at a predetermined flow rate, whereafter tap water constantly flows at a small flow rate from the flush water supply line 33 at the upstream of the water supply valve 34, via the first branch 32 and the flow control valve 35, into the tank-type electrolytic cell 31; when the controller 37 opens the on/off valve 39, the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the flow control valve 35 is closed.

In the above case, tap water constantly flows at a small flow rate from the flush water supply line 33, via the first branch 32 and the flow control valve 35, into the tank-type electrolytic cell 31, whereafter the on/off valve 39 is opened. While the water containing free chlorine produced by the electrolysis flows through the on/off valve 39 and the second branch 36 into the flush water supply line 33 at the downstream of the water supply valve 34, and is supplied to the urinal A31, the operation is the same as described above, that is: the water level in the tank-type electrolytic cell 31 is detected by the float sensor 38, and when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed. When the water in the tank-type electrolytic cell 31 reaches a predetermined level higher than the top of the electrode, the controller 37, on receiving a detection signal from the float sensor 38, opens the on/off valve 39.

By the above method, the flow control valve 35 can be opened to supply the water containing free chlorine to the urinal A31 only at a required time as instructed by the timer, so that the life span of the electrodes of the electrolytic cell can be longer and the necessity for maintenance work can be reduced. Furthermore, the present system is preferable in that it can save resource and energy, since it consumes less water and electricity than a system whereby water is supplied at all times.

The system for cleansing a urinal shown in FIG. 4 may also take a constitution as follows: the flow control valve 35 is connected with the controller 37; a timer is provided in the controller 37; the controller 37 opens the flow control valve 35 only at night and adjusts it at a predetermined flow rate; tap water constantly flows at a small flow rate from the flush water supply line 33 at the upstream of the water supply valve 34, via the first branch 32 and the flow control valve 35, into the tank-type electrolytic cell 31; the water level in the tank-type electrolytic cell 31 is detected by the float sensor 38, and when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the flow control valve 35 is closed.

In the above method, the water containing free chlorine is supplied to the urinal A31 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A31 at predetermined time intervals, or every time of use, by the operation of the automatic flushing system B31, or by manual operation, apart from the operation of the present system for cleansing a urinal, whereby the surface of the urinal A31 is flushed and the standing water in the trap of the urinal is renewed.

The present system for cleansing a urinal may also take a constitution as follows: the controller 37 is connected with the automatic flushing system B31 so that the controller 37 may send a signal to the automatic flushing system B31 to start a normal flush operation; in case of supplying the water containing free chlorine only at night, as shown above, the controller 37 first sends the signal to the automatic flushing system B31 to supply a flush water to the urinal, whereby the standing water of the urinal is renewed (almost 99% of the standing water is freshly renewed thereby) and most of the bacteria are removed from the urinal; after that, the controller 37 opens the flow control valve 35, as described above. Thus the water containing free chlorine is produced as described above and supplied to the urinal A31, whereby the remaining bacteria are killed fully.

In case of supplying the water containing free chlorine only at night, as shown above, it is preferable that the water of high concentration or in large quantity is supplied first at night, whereas the water of lower concentration or in smaller quantity is supplied for the second and subsequent times at night. The concentration of the water containing free chlorine can be raised by either making the opening of the flow control valve 35 smaller or increasing the electric current flowing between the electrodes. On the contrary, the concentration can be lowered by either making the opening of the flow control valve 35 larger or decreasing the electric current flowing between the electrodes. The quantity of the water containing free chlorine supplied to the urinal can be larger by defining said "predetermined level higher than the top of the electrode" higher, whereas the quantity can be smaller by defining said predetermined level lower.

The system for cleansing a urinal shown in FIG. 4 may also take a constitution as follows: the flow control valve 35 is connected with the controller 37; a timer is provided in the controller 37; the controller 37 is connected with the automatic flushing system B31 so that an operation signal of the system B31 is inputted to the controller 37; the timer of the controller 37 starts clocking on receiving the operation signal of the automatic flushing system B331; in case that the urinal is not used for a predetermined period of time after the last use thereof, i.e., that no operation signal of the automatic flushing system B31 is outputted for the predetermined period of time after the system B31 outputs the operation signal on the last use of the urinal A31, the controller 37 opens the flow control valve 35 and adjusts it at a predetermined flow rate; tap water constantly flows at a small flow rate from the flush water supply line 33 at the upstream of the water supply valve 34, via the first branch 32 and the flow control valve 35, into the tank-type electrolytic cell 31; the water level in the tank-type electrolytic cell 31 is detected by the float sensor 38; when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the flow control valve 35 is closed.

By the above method, the water containing free chlorine is supplied to the urinal A3 only in case that the urinal is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented.

The system for cleansing a urinal shown in FIG. 4 may also take a constitution as follows: the flow control valve 35 is connected with the controller 37; a timer is provided in the controller 37; the controller 37 is connected with the automatic flushing system B31 so that an operation signal of the system B31 is inputted to the controller 37; in response to the operation signal of the automatic flushing system B31, the controller 37 opens the flow control valve 35 and adjusts it at predetermined flow rate at every flush after use, i.e., every time the urinal A31 is used and the operation signal of the automatic flushing system B31 is outputted; tap water constantly flows at a small flow rate from the flush water supply line 33 at the upstream of the water supply valve 34, via the first branch 32 and the flow control valve 35, into the tank-type electrolytic cell 31; the water level in the tank-type electrolytic cell 31 is detected by the float sensor 38; when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the flow control valve 35 is closed.

By the above method, the water containing free chlorine can be supplied to the urinal while the surface of the urinal is wet after the flush operation by the automatic flushing system B31 subsequent to a use of the urinal, so that the water containing free chlorine can spread widely over the surface of the urinal that is wet due to the flush operation. As a result, the surface of the urinal can be sterilized effectively and the increase of urease can be prevented. Thus the generation of ammonia is effectively suppressed, so that the deposition of uric stone is prevented and one of the causes of the stench is also prevented.

The system for cleansing a urinal shown in FIG. 4 may also take a constitution as follows: an on/off valve C is provided in the first branch 32 at an upstream of the flow control valve 35; the on/off valve C is connected with the controller 37; a timer is provided in the controller 37; the flow control valve 35 is preset at a predetermined flow rate and the on/off valve C is properly opened to let tap water constantly flow at a small flow rate from the flush water supply line 33 at the upstream of the water supply valve 34, via the first branch 32, the on/off valve C and the flow control valve 35, into the tank-type electrolytic cell 31; when the on/off valve 39 is opened, the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the on/off valve C is closed.

In the above case, tap water constantly flows at a small flow rate from the flush water supply line 33, via the first branch 32, the on/off valve C and the flow control valve 35, into the tank-type electrolytic cell 31, whereafter the on/off valve 39 is opened and the water containing free chlorine produced by the electrolysis flows through the on/off valve 39 and the second branch 36 into the flush water supply line 33 at the downstream of the water supply valve 34, and is supplied to the urinal A31; wherein the operation is the same as described above, i.e., the water level in the tank-type electrolytic cell 31 is detected by the float sensor 38, and when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed. When the water in the tank-type electrolytic cell 31 reaches a predetermined level higher than the top of the electrode, the controller 37, on receiving a detection signal from the float sensor 38, opens the on/off valve 39.

By the above method, the on/off valve C is opened to supply the water containing free chlorine to the urinal A31 only at a required time as instructed by the timer, so that the life span of the electrodes of the electrolytic cell can be longer and the necessity for maintenance work can be reduced. Furthermore, the present system is preferable in that it can save resource and energy, since it consumes less water and electricity than a system whereby water is supplied at all times.

Furthermore, since the on/off valve C is provided, there is no need to control the flow rate every time of opening and closing, and accordingly no need to provide the controller with a flow control mechanism.

The system for cleansing a urinal shown in FIG. 4 may also take a constitution as follows: an on/off valve C is provided in the first branch 32 at an upstream of the flow control valve 35; the on/off valve C is connected with the controller 37; a timer is provided in the controller 37; the flow control valve 35 is preset at a predetermined flow rate; the on/off valve C is opened only at night; tap water constantly flows at a small flow rate from the flush water supply line 33 at the upstream of the water supply valve 34, via the first branch 32, the on/off valve C and the flow control valve 35, into the tank-type electrolytic cell 31; the water level in the tank-type electrolytic cell 31 is detected by the float sensor 38; when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the on/off valve C is closed.

By the above method, the water containing free chlorine is supplied to the urinal A31 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increase in the standing water, since tap water is supplied to the urinal A31 at predetermined time intervals, or every time of use, by the operation of the automatic flushing system B31, or by manual operation, apart from the operation of the present system for cleansing a urinal, whereby the surface of the urinal A31 is flushed and the standing water in the trap of the urinal is renewed. Furthermore, since the on/off valve C is provided, there is no need to control the flow rate every time of opening and closing, and accordingly no need to provide the controller with a flow control mechanism.

The system for cleansing a urinal shown in FIG. 4 may also take a constitution as follows: an on/off valve C is provided in the first branch 32 at an upstream of the flow control valve 35; the on/off valve C is connected with the controller 37; the flow control valve 35 is preset at a predetermined flow rate; a timer is provided in the controller 37; the controller 37 is connected with the automatic flushing system B31 so that an operation signal of the system B31 is inputted to the controller 37; the timer of the controller 37 starts clocking on receiving the operation signal of the automatic flushing system B31; in case that the urinal A31 is not used for a predetermined period of time after the last use thereof, i.e., that no operation signal of the automatic flushing system B31 is outputted for the predetermined period of time after the system B31 outputs the operation signal on the last use of the urinal A31, the controller 37 opens the on/off valve C as instructed by the timer; tap water constantly flows at a small flow rate from the flush water supply line 33 at the upstream of the water supply valve 34, via the first branch 32, the on/off valve C and the flow control valve 35, into the tank-type electrolytic cell 31; the water level in the tank-type electrolytic cell 31 is detected by the float sensor 38; when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the on/off valve C is closed.

By the above method, the water containing free chlorine is supplied to the urinal A31 only in case that the urinal is not used for the predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented. Furthermore, since the on/off valve C is provided, there is no need to control the flow rate every time of opening and closing, and accordingly no need to provide the controller with a flow control mechanism.

The system for cleansing a urinal shown in FIG. 4 may also take a constitution as follows: an on/off valve C is provided in the first branch 32 at an upstream of the flow control valve 35; the on/off valve C is connected with the controller 37; the flow control valve 35 is preset at a predetermined flow rate; a timer is provided in the controller 37; the controller 37 is connected with the automatic flushing system B31 so that an operation signal of the system B31 is inputted to the controller 37; in response to the operation signal of the automatic flushing system B31, the controller 37 opens the on/off valve C at every flush after use, i.e., every time the urinal A31 is used and the operation signal of the automatic flushing system B31 is outputted; tap water constantly flows at a small flow rate from the flush water supply line 33 at the upstream of the water supply valve 34, via the first branch 32, the on/off valve C and the flow control valve 35, into the tank-type electrolytic cell 31; the water level in the tank-type electrolytic cell 31 is detected by the float sensor 38; when the water level in the tank-type electrolytic cell 31 reaches the top of the electrode, the controller 37, on receiving a detection signal from the float sensor 38, applies voltage between the electrodes, whereby the water stored in the tank-type electrolytic cell 31 is electrolyzed; when the water in the tank-type electrolytic cell 31 reaches a predetermined level higher than the top of the electrode, the controller 37, on receiving a detection signal from the float sensor 38, opens the on/off valve 39, whereby the water containing free chlorine produced by the electrolysis flows through the on/off valve 39 and the second branch 36 into the flush water supply line 33 at the downstream of the water supply valve 34, and is supplied to the urinal A31; when the water in the tank-type electrolytic cell 31 reaches a predetermined level lower than the top of the electrode, the on/off valve 39 is closed and at the same time, or with a delay, the on/off valve C is closed.

By the above method, the water containing free chlorine is supplied to the urinal while the surface of the urinal is wet after the flush operation by the automatic flushing system B31 subsequent to a use of the urinal, so that the water containing free chlorine can spread widely over the surface of the urinal that is wet due to the flush operation. As a result, the surface of the urinal can be sterilized effectively, the increase of urease can be prevented. Thus the generation of ammonia is effectively suppressed, so that the deposition of uric stone is prevented and one of the causes of the stench is also prevented.

Figure 5:
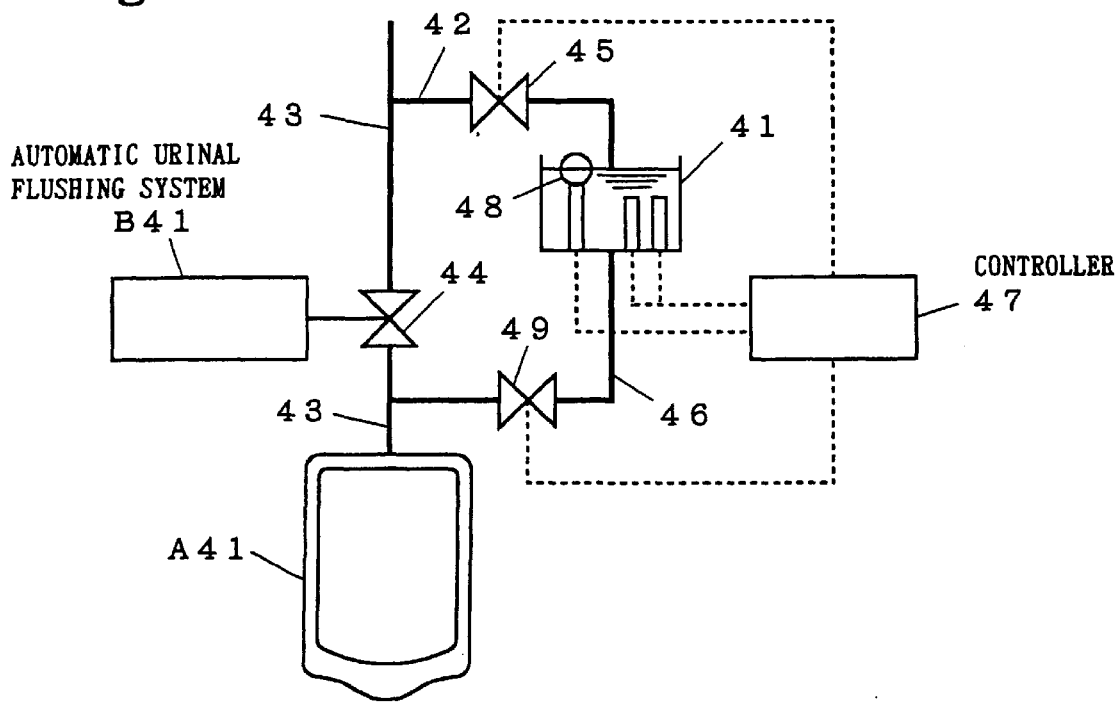
FIG. 5 shows a machinery structure of a system for cleansing a urinal comprising a tank-type electrolytic cell provided parallel to an existing flush water supply line, and having a constitution that an on/off valve for passing and stopping the tap water flowing into the tank-type electrolytic cell and an on/off valve for passing and stopping the water containing free chlorine flowing from the tank-type electrolytic cell are opened and closed as instructed by a controller.

FIG. 5 shows another embodiment of the system for cleansing a urinal according to the present invention. The present system comprises a tank-type electrolytic cell 41 having at least a pair of electrodes and a float sensor 48. The tank-type electrolytic cell 41 is connected by a first branch 42 with a flush water supply line 43 at an upstream of a water supply valve 44 consisting of a flush valve or the like. An on/off valve 45 is provided in the first branch 42. The tank-type electrolytic cell 41 is connected by a second branch 46 with the flush water supply line 43 at a downstream of the water supply valve 44. An on/off valve 49 is provided in the second branch 46. The flush water supply line 43 to which the second branch 46 is connected leads to a urinal A41. The electrodes and the float sensor 48 of the tank-type electrolytic cell 41 and the on/off valves 45 and 49 are connected with a controller 47.

In the present system for cleansing a urinal, tap water flows from the flush water supply line 43 at the upstream of the water supply valve 44, via the first branch 42 and the on/off valve 45, into the tank-type electrolytic cell 41. The water level in the tank-type electrolytic cell 41 is detected by the float sensor 48. When the water in the tank-type electrolytic cell 41 reaches a predetermined level higher than the top of the electrode, the controller 47, on receiving a detection signal from the float sensor 48, closes the on/off valve 45. The controller 47, being provided with a timer, applies voltage between the electrodes only when the water in the tank-type electrolytic cell 41 is at the predetermined level higher than the top of the electrode during a predetermined period of time, whereby the water stored in the tank-type electrolytic cell 41 is electrolyzed. The on/off valve 49 is immediately opened by the controller 47 after the electrolysis of the water stored in the tank-type electrolytic cell 41, whereby the water containing free chlorine produced by the electrolysis flows through the on/off valve 49 and the second branch 46 into the flush water supply line 43 at the downstream of the water supply valve 44, and is supplied to the urinal A41.

Apart from the operation of the present system for cleansing a urinal, tap water is also supplied to the urinal A41 by the automatic flushing system B41, or by manual operation, every time of use, whereby the surface of the urinal A41 is flushed and the standing water in the trap of the urinal is renewed.

The present system for cleansing a urinal, similar to the systems shown in FIGS. 1–4, requires less maintenance work and is safer to users than the conventional flushing system using chemicals mixed with the flush water.

In the above system, the voltage is applied between the electrodes of the tank-type electrolytic cell 41 properly as instructed by the timer, and the water containing free chlorine is supplied to the urinal A41. Consequently, the increase and adhesion of urease due to the action of living bacteria can be effectively suppressed and the increase in pH due to the solution of ammonia is suppressed, so that the deposition of uric stone is prevented and one of the causes of the stench is also prevented.

In the above system for cleansing a urinal, it is possible to determine the period for applying voltage between the electrodes of the tank-type electrolytic cell 41 at predetermined time intervals as instructed by the timer. By this method, the water containing free chlorine is supplied to the urinal A41 at predetermined time intervals and the electrolysis occurs at intervals, therefore the life span of the electrodes of the electrolytic cell can be longer and the necessity for maintenance work can be reduced. Furthermore, the present system can save resource and energy, since it consumes less water and electricity than a system whereby water is supplied at all times.

In the above system for cleansing a urinal, it is possible to determine the period for applying voltage between the electrodes of the tank-type electrolytic cell 41 only at night as instructed by the timer, whereby the water containing free chlorine is supplied to the urinal A41 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A41 at predetermined time intervals, or every time of use, by the operation of the automatic flushing system B41, or by manual operation, apart from the operation of the present system for cleansing a urinal, whereby the surface of the urinal A41 is flushed and the standing water in the trap of the urinal is renewed. Furthermore, the present system can save resource and energy, since it consumes less water and electricity than a system whereby water is supplied at all times.

The present system for cleansing a urinal may also take a constitution as follows: the controller 47 is connected with the automatic flushing system B41 so that the controller 47 sends a signal to the automatic flushing system B41 to start a normal flush operation; in case of supplying the water containing free chlorine only at night, as shown above, the controller 47 first sends the signal to the automatic flushing system B41 to supply a flush water to the urinal, whereby the standing water of the urinal is renewed (almost 99% of the standing water is freshly renewed thereby), so that most of the bacteria are removed from the urinal; whereafter the controller 47 opens the on/off valve 45, as described above. Thus the water containing free chlorine is produced, as described above, and supplied to the urinal A41, whereby the remaining bacteria can be killed fully.

In case of supplying the water containing free chlorine only at night, as shown above, it is preferable that the water of high concentration or in large quantity is supplied first at night, whereas the water of lower concentration or in smaller quantity is supplied for the second and subsequent times at night. The concentration of the water containing free chlorine can be raised by increasing the electric current flowing between the electrodes, whereas the concentration can be lowered by decreasing the electric current flowing between the electrodes. The quantity of the water containing free chlorine supplied to the urinal can be larger by defining said "predetermined level higher than the top of the electrode" higher, whereas the quantity can be smaller by defining said predetermined level lower.

The above system for cleansing a urinal may also take a constitution as follows: the controller 47 is further connected with the automatic flushing system B41 so that an operation signal of the automatic flushing system B41 is inputted to the controller 47; the timer of the controller 47 starts clocking on receiving the operation signal of the automatic flushing system B41; in case that the urinal A41 is not used for a predetermined period of time after the last use thereof, i.e., that no operation signal of the automatic flushing system B41 is outputted for the predetermined period of time after the system B41 outputs the operation signal on the last use of the urinal A41, the controller 47 determines the period for applying voltage between the electrodes of the tank-type electrolytic cell 41 as instructed by the timer. By this method the water containing free chlorine is supplied to the urinal A41 only in case that the urinal A41 is not used for a predetermined period of time after the last use of the urinal, whereby such a situation can be prevented that bacteria increase in the standing water of the urinal and urease increases and adheres to the surface of the urinal when the urinal is not used, so that the deposition of uric stone can be prevented and one of the causes of the stench can be prevented. Furthermore, the present system can save resource and energy, since it consumes less water and electricity than a system whereby water is supplied at all times.

The above system for cleansing a urinal may also take a constitution as follows: the controller 47 is connected with the automatic flushing system B41 so that an operation signal of the automatic flushing system B41 is inputted to the controller 47; in response to the operation signal of the automatic flushing system B41, the controller 47 determines the period for applying voltage between the electrodes of the tank-type electrolytic cell 41 at every flush after use, i.e., every time the urinal A41 is used and the operation signal of the automatic flushing system B41 is outputted. By this method, the water containing free chlorine is supplied to the urinal while the surface of the urinal is wet after the flush operation by the automatic flushing system B41 subsequent to a use of the urinal, so that the water containing free chlorine can spread widely over the surface of the urinal that is wet due to the flush operation. As a result, the surface of the urinal can be sterilized effectively, the increase of urease can be prevented. Thus the generation of ammonia is effectively suppressed, so that the deposition of uric stone is prevented and one of the causes of the stench is also prevented.

Figure 6A:
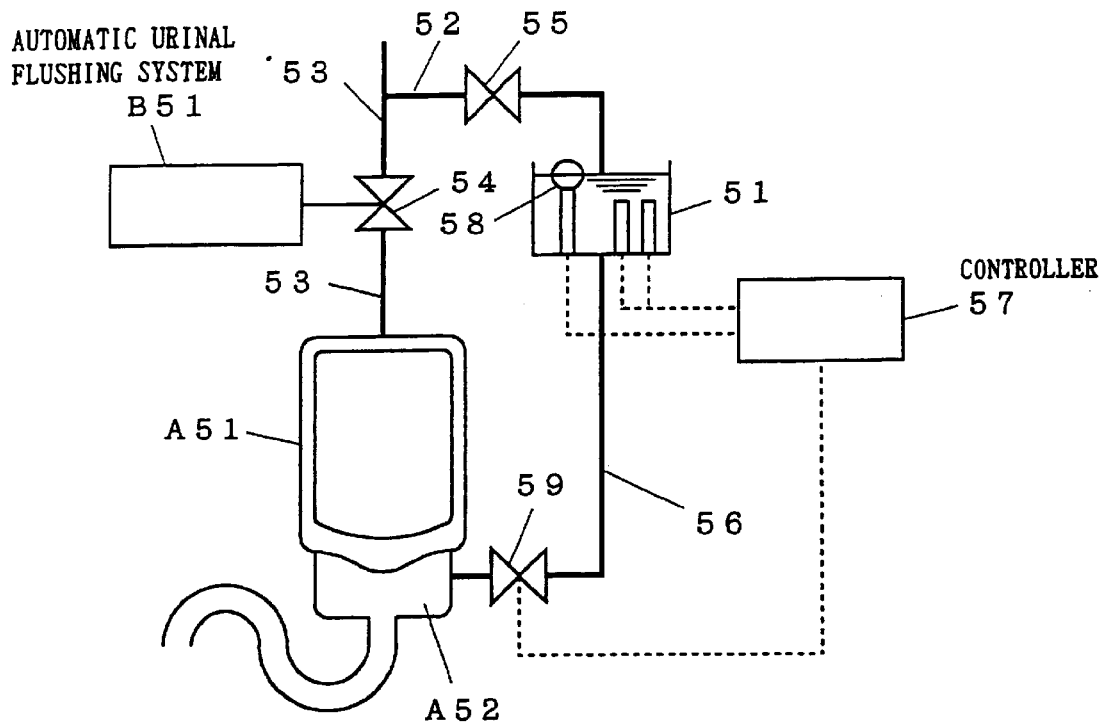
FIG. 6(a) shows a machinery structure of a system for cleansing a urinal comprising a tank-type electrolytic cell provided parallel to an existing flush water supply line, and having a constitution that an on/off valve for passing and stopping the water containing free chlorine flowing from the tank-type electrolytic cell is opened and closed as instructed by a controller, and that the water containing free chlorine is supplied to the trap of the urinal.

FIG. 6(a) shows another embodiment of the system for cleansing a urinal according to the present invention. The present system comprises a tank-type electrolytic cell 51 having at least a pair of electrodes and a float sensor 58. The tank-type electrolytic cell 51 is connected by a first branch 52 with a flush water supply line 53 at an upstream of a water supply valve 54 consisting of a flush valve or the like. A flow control valve 55 is provided in the first branch 52. The tank-type electrolytic cell 51 is connected by a second branch 56 with the trap A52 of the urinal. An on/off valve 59 is provided in the second branch 56. The electrodes and the float sensor 58 of the tank-type electrolytic cell 51 and the on/off valve 59 are connected with a controller 57.

In the present system for cleansing a urinal, tap water constantly flows at a small flow rate from the flush water supply line 53 at the upstream of the water supply valve 54, via the first branch 52 and the flow control valve 55, into the tank-type electrolytic cell 51. The water level in the tank-type electrolytic cell 51 is detected by the float sensor 58. When the water level in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed. When the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 into the trap A52. By this method, the standing water of the urinal A51 can be sterilized properly and urease carried by bacteria is removed from the urinal A51 together with the bacteria, so that the precipitation of uric stone and the formation of yellowish stain are prevented in the trap A52, a portion where yellowish stain sticks most outstandingly.

Apart from the operation of the present system for cleansing a urinal, tap water is also supplied to the urinal A51 by the operation of the automatic flushing system B51, or by manual operation, every time of use, whereby the surface of the urinal A51 is flushed and the standing water in the trap A52 is renewed.

The present system for cleansing a urinal, similar to the systems shown in FIGS. 1–5, requires less maintenance work and is safer to users than the conventional flushing system using chemicals mixed with the flush water, since the liquid for cleansing a urinal, or the water containing free chlorine, is obtained by the electrolysis of tap water.

By the above system, the water containing free chlorine is supplied to the urinal A51 at predetermined time intervals by setting the flow rate of the flow control valve 55 properly. Consequently, the increase and adhesion of urease due to the action of living bacteria can be effectively suppressed and the increase in pH due to the decomposition of ammonia is suppressed, so that the deposition of uric stone is prevented and one of the causes of the stench is also prevented. Since the electrolysis occurs only at intervals, the life span of the electrodes of the electrolytic cell can be longer and the necessity for maintenance work can be reduced. Furthermore, the present system can save resource and energy, since it consumes less water and electricity than a system whereby water is supplied at all times.

The system for cleansing a urinal shown in FIG. 6(*a*) may also take a constitution as follows: the flow control valve 55 is connected with the controller 57; a timer is provided in the controller 57; the flow control valve 55 is opened properly and regulated at a predetermined flow rate; tap water constantly flows at a small flow rate from the flush water supply line 53 at the upstream of the water supply valve 54, via the first branch 52 and the flow control valve 55, into the tank-type electrolytic cell 51; by opening the on/off valve 59, the water containing free chlorine produced by the electrolysis is supplied through the on/off valve 59 and the second branch 56 into the trap A52; when the water in the tank-type electrolytic cell 51 reaches a predetermined level lower than the top of the electrode, the on/off valve 59 is closed and at the same time, or with a delay, the flow control valve 55 is closed.

In this case, the tap water constantly flows at a small flow rate from the flush water supply line 53 at the upstream of the water supply valve 54, via the first branch 52 and the flow control valve 55, into the tank-type electrolytic cell 51, whereafter the on/off valve 59 is opened, and the water containing free chlorine produced by the electrolysis flows through the on/off valve 59 and the second branch 56 into the trap A52. In the above process, the operation is the same as described above, i.e., the water level in the tank-type electrolytic cell 51 is detected by the float sensor 58, and when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed. When the water in the tank-type electrolytic cell 51 reaches a predetermined level higher than the top of the electrode, the controller 57, on receiving a detection signal from the float sensor 58, opens the on/off valve 59.

By the above method, the flow control valve 55 is opened to supply the water containing free chlorine to the trap A52 only at a required time as instructed by the timer, so that the life span of the electrodes of the electrolytic cell can be longer and the necessity for maintenance work can be reduced. Furthermore, the present system can save resource and energy, since it consumes less water and electricity than a system whereby water is supplied at all times.

The system for cleansing a urinal shown in FIG. 6(*a*) may also take a constitution as follows: the flow control valve 55 is connected with the controller 57; a timer is provided in the controller 57; the controller 57 opens the flow control valve 55 only at night and adjusts it at a predetermined flow rate; whereafter tap water constantly flows at a small flow rate from the flush water supply line 53 at the upstream of the water supply valve 54, via the first branch 52 and the flow control valve 55, into the tank-type electrolytic cell 51; the water level in the tank-type electrolytic cell 51 is detected by the float sensor 58, and when the water level in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 to the trap A52; when the water in the tank-type electrolytic cell 51 reaches a predetermined level lower than the top of the electrode, the on/off valve 59 is closed and at the same time, or with a delay, the flow control valve 55 is closed.

By the above method, the water containing free chlorine is supplied to the trap A52 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A51 at predetermined time intervals, or every time of use, by the operation of the automatic flushing system B51, or by manual operation, apart from the operation of the present system for cleansing a urinal, whereby the surface of the urinal A51 is flushed and the standing water in the trap A52 is renewed.

The system for cleansing a urinal shown in FIG. 6(*a*) may also take a constitution as follows:

the flow control valve 55 is connected with the controller 57; a timer is provided in the controller 57; the controller 57 is connected with the automatic flushing system B51 so that an operation signal of the system B51 is inputted to the controller 57; the timer of the controller 57 starts clocking on receiving the operation signal of the automatic flushing system B51; in case that the urinal A51 is not used for a predetermined period of time after the last use thereof, i.e., that no operation signal of the automatic flushing system B51 is outputted for the predetermined period of time after the system B51 outputs the operation signal on the last use of the urinal A51, the controller 57 opens the flow control valve 55 as instructed by the timer and regulates it at a predetermined flow rate; whereafter tap water constantly flows at a small flow rate from the flush water supply line 53 at the upstream of the water supply valve 54, via the first branch 52 and the flow control valve 55, into the tank-type electrolytic cell 51; the water level in the tank-type electrolytic cell 51 is detected by the float sensor 58; when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 and is supplied to the trap A52; when the water in the tank-type electrolytic cell 51 reaches a predetermined level lower than the top of the electrode, the on/off valve 59 is closed and at the same time, or with a delay, the flow control valve 55 is closed.

By this method, the water containing free chlorine is supplied to the trap A52 only in case that the urinal A51 is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented.

The system for cleansing a urinal shown in FIG. 6(a) may also take a constitution as follows: the flow control valve 55 is connected with the controller 57; a timer is provided in the controller 57; the controller 57 is connected with the automatic flushing system B51 so that an operation signal of the system B51 is inputted to the controller 57; in response to the operation signal of the automatic flushing system B51, the controller 57 opens the flow control valve 55 and regulates it at predetermined flow rate at every flush after use, i.e., every time the urinal A51 is used and the operation signal of the automatic flushing system B51 is outputted, whereby tap water constantly flows at a small flow rate from the flush water supply line 53 at the upstream of the water supply valve 54, via the first branch 52 and the flow control valve 55, into the tank-type electrolytic cell 51; the water level in the tank-type electrolytic cell 51 is detected by the float sensor 58; when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 and is supplied to the trap A52; when the water in the tank-type electrolytic cell 51 reaches a predetermined level lower than the top of the electrode, the on/off valve 59 is closed and at the same time, or with a delay, the flow control valve 55 is closed.

The system for cleansing a urinal shown in FIG. 6(a) may also take a constitution as follows: an on/off valve D is provided in the first branch 52 at an upstream of the flow control valve 55; the on/off valve D is connected with the controller 57; a timer is provided in the controller 57; the flow control valve 55 is preset at a predetermined flow rate and the on/off valve D is properly opened to let tap water constantly flow at a small flow rate from the flush water supply line 53 at the upstream of the water supply valve 54, via the first branch 52, the on/off valve D and the flow control valve 55, into the tank-type electrolytic cell 51; when the on/off valve 59 is opened, the water containing free chlorine produced by the electrolysis flows through the on/off valve 59 and the second branch 56 and is supplied to the trap A52; when the water in the tank-type electrolytic cell 51 reaches a predetermined level lower than the top of the electrode, the on/off valve 59 is closed and at the same time, or with a delay, the on/off valve D is closed.

In this case, tap water constantly flows at a small flow rate from the flush water supply line 53 at the upstream of the water supply valve 54, via the first branch 52, the on/off valve D and the flow control valve 55, into the tank-type electrolytic cell 51, whereafter the on/off valve 59 is opened and the water containing free chlorine produced by the electrolysis flows through the on/off valve 59 and the second branch 56 and is supplied to the trap A52; wherein the operation is the same as described above, i.e., the water level in the tank-type electrolytic cell 51 is detected by the float sensor 58, and when the water level in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed. When the water in the tank-type electrolytic cell 51 reaches a predetermined level higher than the top of the electrode, the controller 57, on receiving a detection signal from the float sensor 58, opens the on/off valve 59.

By the above method, the on/off valve D is opened to supply the water containing free chlorine to the trap A52 only at a required time as instructed by the timer, so that the life span of the electrodes of the electrolytic cell can be longer and the necessity for maintenance work can be reduced. Furthermore, the present system is preferable in that it can save resource and energy, since it consumes less water and electricity than a system whereby water is supplied at all times.

Furthermore, since the on/off valve D is provided, there is no need to control the flow rate every time of opening and closing, and accordingly no need to provide the controller with a flow control mechanism.

The system for cleansing a urinal shown in FIG. 6(a) may also take a constitution as follows: an on/off valve D is provided in the first branch 52 at an upstream of the flow control valve 55; the on/off valve D is connected with the controller 57; a timer is provided in the controller 57; the flow control valve 55 is preset at a predetermined flow rate and the on/off valve D is opened only at night; tap water constantly flows at a small flow rate from the flush water supply line 53 at the upstream of the water supply valve 54, via the first branch 52, the on/off valve D and the flow control valve 55, into the tank-type electrolytic cell 51; the water level in the tank-type electrolytic cell 51 is detected by the float sensor 58; when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 and is supplied to the trap A52; when the water in the tank-type electrolytic cell 51 reaches a predetermined level lower than the top of the electrode, the on/off valve 59 is closed and at the same time, or with a delay, the on/off valve D is closed.

By this method, the water containing free chlorine is supplied to the trap A52 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A51 at predetermined time intervals, or every time of use, by the operation of the automatic flushing system B51, or by manual operation, apart from the operation of the present system for cleansing a urinal, whereby the surface of the urinal A51 is flushed and the standing water in the trap A52 is renewed. Furthermore, since the on/off valve D is provided, there is no need to control the flow rate every time of opening and closing, and accordingly no need to provide the controller with a flow control mechanism.

The system for cleansing a urinal shown in FIG. 6(a) may also take a constitution as follows: an on/off valve D is provided in the first branch 52 at an upstream of the flow control valve 55; the on/off valve D is connected with the controller 57; the flow control valve 55 is preset at a predetermined flow rate; a timer is provided in the controller 57; the controller 57 is connected with the automatic flushing system B51 so that an operation signal of the system B51 is inputted to the controller 57; the timer of the controller 57 starts clocking on receiving the operation signal of the automatic flushing system B51; in case that the urinal A51 is not used for a predetermined period of time after the last use thereof, i.e., that no operation signal of the automatic flushing system B51 is outputted for the predetermined period of time after the system B51 outputs the operation signal on the last use of the urinal A51, the controller 57 opens the on/off valve D as instructed by the timer, whereby tap water constantly flows at a small flow rate from the flush water supply line 53 at the upstream of the water supply valve 54, via the first branch 52, the on/off valve D and the flow control valve 55, into the tank-type electrolytic cell 51; the water level in the tank-type electrolytic cell 51 is detected by the float sensor 58; when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 and is supplied to the trap A52; when the water in the tank-type electrolytic cell 51 reaches a predetermined level lower than the top of the electrode, the on/off valve 59 is closed and at the same time, or with a delay, the on/off valve D is closed.

By this method, the water containing free chlorine is supplied to the trap A52 only in case that the urinal A51 is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented. Furthermore, since the on/off valve D is provided, there is no need to control the flow rate every time of opening and closing, and accordingly no need to provide the controller with a flow control mechanism.

The system for cleansing a urinal shown in FIG. 6(a) may also take a constitution as follows: an on/off valve D is provided in the first branch 52 at an upstream of the flow control valve 55; the on/off valve D is connected with the controller 57; the flow control valve 55 is preset at a predetermined flow rate; a timer is provided in the controller 57; the controller 57 is connected with the automatic flushing system B51 so that an operation signal of the system B51 is inputted to the controller 57; in response to the operation signal of the automatic flushing system B51, the controller 57 opens the on/off valve D at every flush after use, i.e., every time the urinal A51 is used and the operation signal of the automatic flushing system B51 is outputted; whereby tap water constantly flows at a small flow rate from the flush water supply line 53 at the upstream of the water supply valve 54, via the first branch 52, the on/off valve D and the flow control valve 55, into the tank-type electrolytic cell 51; the water level in the tank-type electrolytic cell 51 is detected by the float sensor 58; when the water in the tank-type electrolytic cell 51 reaches the top of the electrode, the controller 57, on receiving a detection signal from the float sensor 58, applies voltage between the electrodes, whereby the water stored in the tank-type electrolytic cell 51 is electrolyzed; when the water in the tank-type electrolytic cell 51 reaches a predetermined level higher than the top of the electrode, the controller 57, on receiving a detection signal from the float sensor 58, opens the on/off valve 59, whereby the water containing free chlorine produced by the electrolysis flows through the on/off valve 59 and the second branch 56 and is supplied to the trap A52 the urinal; when the water in the tank-type electrolytic cell 51 reaches a predetermined level lower than the top of the electrode, the on/off valve 59 is closed and at the same time, or with a delay, the on/off valve D is closed.

Figure 6B:
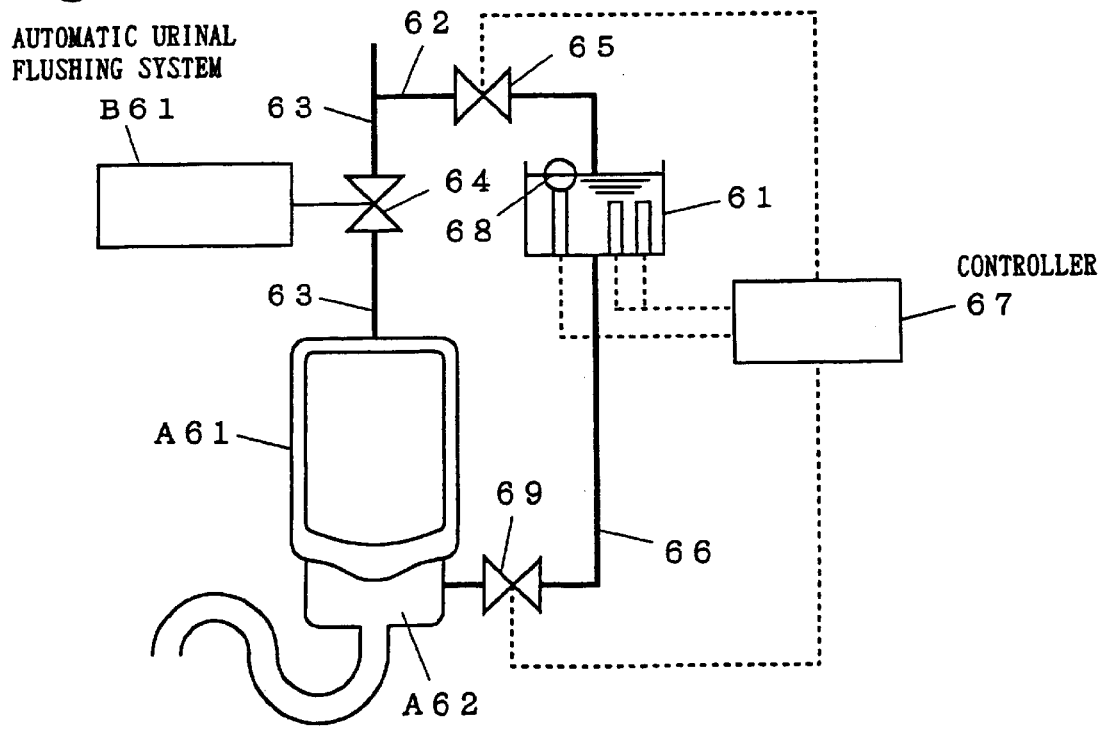
FIG. 6(b) shows a machinery structure of a system for cleansing a urinal comprising a tank-type electrolytic cell provided parallel to an existing flush water supply line, and having a constitution that an on/off valve for passing and stopping tap water flowing into the tank-type electrolytic cell and an on/off valve for passing and stopping the water containing free chlorine flowing from the tank-type electrolytic cell are opened and closed as instructed by a controller, and that the water containing free chlorine is supplied to the trap of the urinal.

FIG. 6(b) shows another embodiment of the system for cleansing a urinal according to the present invention. The present system comprises a tank-type electrolytic cell 61 having at least a pair of electrodes and a float sensor 68. The tank-type electrolytic cell 61 is connected by a first branch 62 with a flush water supply line 63 at an upstream of a water supply valve 64 consisting of a flush valve or the like. An on/off valve 65 is provided in the first branch 62. The tank-type electrolytic cell 61 is connected by a second branch 66 with the trap A62 of the urinal. An on/off valve 69 is provided in the second branch 66. The electrodes and the float sensor 68 of the tank-type electrolytic cell 61 and the on/off valves 65 and 69 are connected with a controller 67.

In the present system for cleansing a urinal, tap water flows from the flush water supply line 63 at the upstream of the water supply valve 64, via the first branch 62 and the on/off valve 65, into the tank-type electrolytic cell 61. The water level in the tank-type electrolytic cell 61 is detected by the float sensor 68. When the water in the tank-type electrolytic cell 61 reaches a predetermined level higher than the top of the electrode, the controller 67, on receiving a detection signal from the float sensor 68, closes the on/off valve 65. The controller 67, being provided with a timer, applies voltage between the electrodes only when the water in the tank-type electrolytic cell 61 is at the predetermined level higher than the top of the electrode during a predetermined period of time, whereby the water stored in the tank-type electrolytic cell 61 is electrolyzed. The on/off valve 69 is immediately opened by the controller 67 after the electrolysis of the water stored in the tank-type electrolytic cell 61, whereby the water containing free chlorine produced by the electrolysis flows through the on/off valve 69 and the second branch 66 and is supplied to the trap A62. By this method, the standing water of the urinal A61 is properly sterilized and urease carried by bacteria is removed from the urinal A61 together with the bacteria. Thus the precipitation of uric stone and the formation of yellowish stain are prevented in the trap A62 where yellowish stain sticks most outstandingly.

Apart from the operation of the present system for cleansing a urinal, tap water is also supplied to the urinal A61 by the automatic flushing system B61, or by manual operation, every time of use, whereby the surface of the urinal A61 is flushed and the standing water in the trap A62 is renewed.

Similar to the systems shown in FIGS. 1–6(a), the present system requires less maintenance work and is safer to users than the conventional flushing system using chemicals mixed with the flush water.

In the above system, the voltage is applied to the electrodes of the tank-type electrolytic cell 61 properly as instructed by the timer, and the water containing free chlorine is supplied to the trap A62. Consequently, the increase and deposition of urease due to the action of living bacteria can be effectively suppressed and the increase in pH due to the solution of ammonia is suppressed, so that the deposition of uric stone is prevented and one of the causes of the stench is also prevented.

In the above system for cleansing a urinal, it is possible to determine the period for applying voltage between the electrodes of the tank-type electrolytic cell 61 at predetermined time intervals as instructed by the timer. By this method, the water containing free chlorine is supplied to the trap A62 at predetermined time intervals. Since the electrolysis occurs at intervals, the life span of the electrodes of the electrolytic cell can be longer and the necessity for less maintenance work can be reduced. Furthermore, the present system can save resource and energy, since it consumes less water and electricity than a system whereby water is supplied at all times.

In the above system for cleansing a urinal, it is possible to determine the period for applying voltage between the electrodes of the tank-type electrolytic cell 61 only at night as instructed by the timer. By this method, the water containing free chlorine is supplied to the trap A62 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A61 at predetermined time intervals, or every time of use, by the operation of the automatic flushing system B61, or by manual operation, apart from the operation of the present system for cleansing a urinal, whereby the surface of the urinal A61 is flushed and the standing water in the trap A62 is renewed. Furthermore, the present system can save resource and energy, since it consumes less water and electricity than a system whereby water is supplied at all times.

The above system for cleansing a urinal may also take a constitution as follows: the controller 67 is further connected with the automatic flushing system B61 so that an operation signal of the automatic flushing system B61 is inputted to the controller 67; the timer of the controller 67 starts clocking on receiving the operation signal of the automatic flushing system B61; in case that the urinal A61 is not used for a predetermined period of time after the last use thereof, i.e., that no operation signal of the automatic flushing system B61 is outputted for the predetermined period of time after the system B61 outputs the operation signal on the last use of the urinal A61, the controller 67 determines the period for applying voltage between the electrodes of the tank-type electrolytic cell 61 as instructed by the timer. By this method, the water containing free chlorine is supplied to the urinal A61 only in case that the urinal A61 is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented. Furthermore, the present system can save resource and energy, since it consumes less water and electricity than a system whereby water is supplied at all times.

The above system for cleansing a urinal may also take a constitution as follows: the controller 67 is connected with the automatic flushing system B61 so that an operation signal of the automatic flushing system B61 is inputted to the controller 67; in response to the operation signal of the automatic flushing system B61, the controller 67 determines the period for applying voltage between the electrodes of the tank-type electrolytic cell 61, as instructed by the timer, at every flush after use, i.e., every time the urinal A61 is used and the operation signal of the automatic flushing system B61 is outputted.

Figure 7:
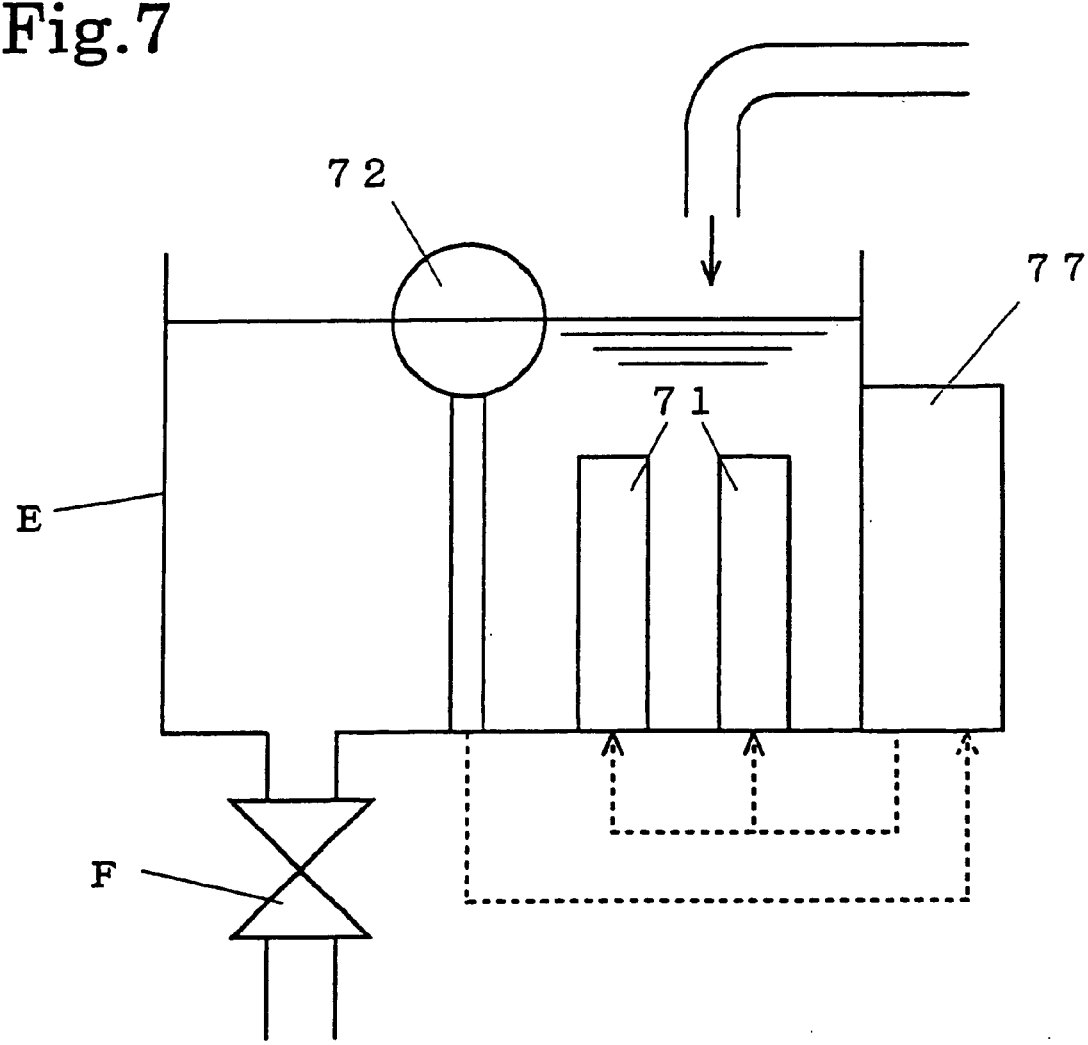
FIG. 7 shows a machinery structure of a system for cleansing a urinal utilizing a urinal water tank as an electrolyte bath.

FIG. 7 shows another embodiment of the system for cleansing a urinal according to the present invention. The present system comprises a cistern tank E wherein at least a pair of electrodes 71 and a float sensor 72 are disposed. A controller 77 is attached to the cistern tank E. The electrodes 71 and the float sensor 72 are connected with the controller 77.

In the present system for cleansing a urinal, the water level in the cistern tank E is detected by the float sensor 72. When the water in the cistern tank E reaches the top of the electrode 71, the controller 77, on receiving a detection signal from the float sensor 72, applies voltage between the electrodes 71, whereby the tap water stored in the cistern tank E is electrolyzed. An on/off valve F provided to the cistern tank E is opened by the operation of the automatic flushing system not shown in the figure, or by manual operation, whereby the water containing free chlorine produced by the electrolysis is supplied from the cistern tank E to the urinal not shown in the figure.

In the present system for cleansing a urinal, the surface of the urinal is sterilized and the increase of urease is prevented every time the urinal is used, whereby the generation of ammonia can be effectively suppressed, so that the deposition of uric stone is prevented and one of the causes of the stench is also prevented. Furthermore, similar to the system of FIGS. 1 through 6(b), the present system requires less maintenance work and is safer to users than the conventional system using chemicals mixed with flush water.

In the present system for cleansing a urinal shown in FIG. 7, it is possible to provide a timer in the controller 77 so that the tap water stored in the cistern tank E is electrolyzed only in case that the water level in the cistern tank E is higher than the top of the electrode during a predetermined period of time. By this method, water and electricity can be saved, thus contributing to saving resource and energy, since the water containing free chlorine produced by the electrolysis is supplied from the cistern tank E to the not shown urinal at predetermined time intervals irrespective of how frequently the urinal is used.

Figure 8:
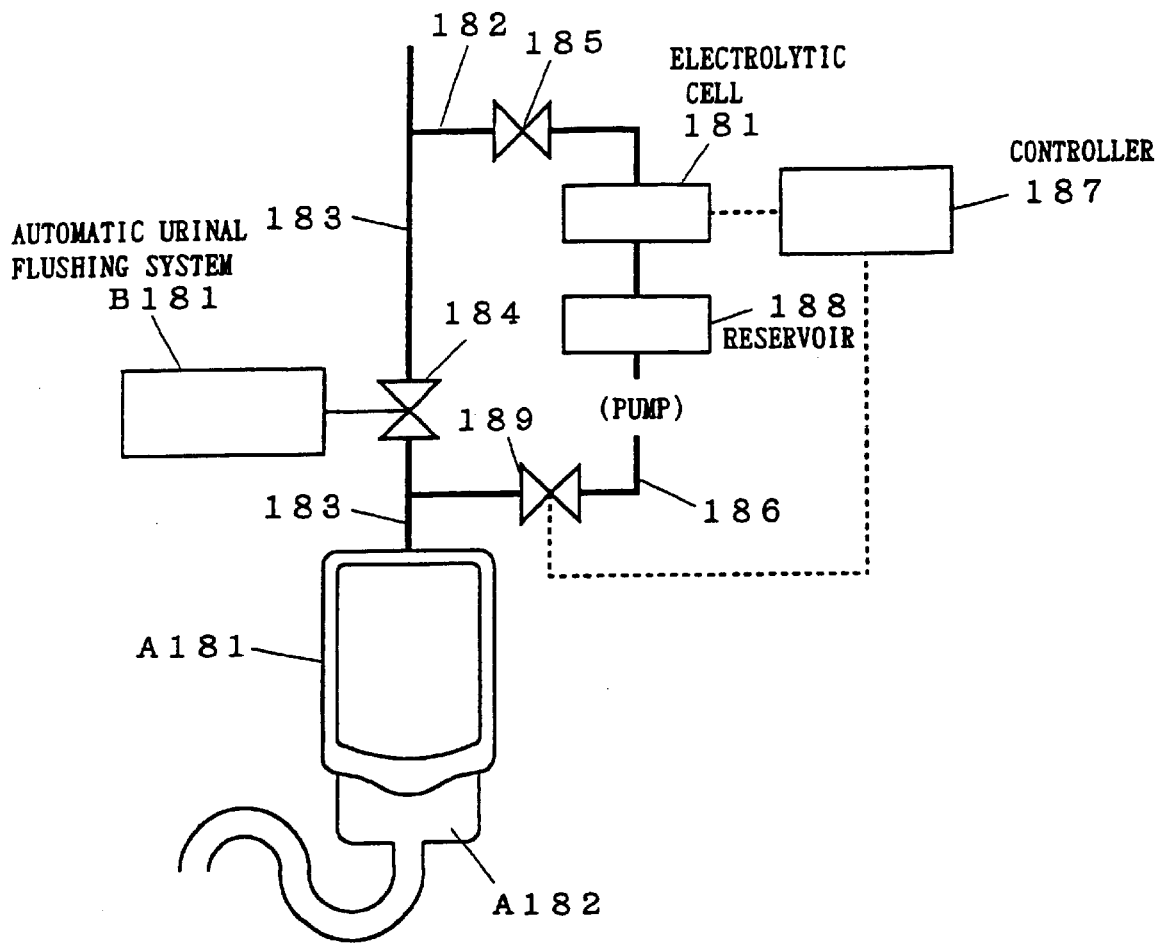
FIG. 8 shows a machinery structure of a system for cleansing a urinal comprising an electrolytic cell and a reservoir, both being provided parallel to an existing flush water supply line, and having a constitution that the water containing free chlorine produced in the electrolytic cell is stored in the reservoir and an on/off valve for passing and stopping the water containing free chlorine flowing from the reservoir is opened and closed as instructed by a controller.

FIG. 8 shows another embodiment of the system for cleansing a urinal according to the present invention. The present system comprises a continuous electrolytic cell 181 having at least a pair of electrodes, a passage formed between the electrodes and an inlet and an outlet both leading to the passage. The continuous electrolytic cell 181 is connected by a first branch 182 with a flush water supply line 183 at an upstream of a water supply valve 184 consisting of a flush valve or the like. An on/off valve 185 consisting of a solenoid valve or the like is provided in the first branch 182. A reservoir 188 for storing the water containing free chlorine produced by the electrolysis by the continuous electrolytic cell 181 is disposed at a downstream of the continuous electrolytic cell 181. The reservoir 188 is connected by a second branch 186 with the flush water supply line 183 at the downstream of the water supply valve 184. The flush water supply line 183 to which the second branch 186 is connected leads to a urinal A181. The electrolytic cell 181 and an on/off valve 189 provided in the second branch 186 are connected with a controller 187 having a timer. The water supply valve 184 is connected with a known automatic flushing system B181.

In the present system for cleansing a urinal, tap water flows from the flush water supply line 183 at the upstream of the water supply valve 184 via the first branch 182 and the on/off valve 185 into the continuous electrolytic cell 181, wherein the tap water is electrolyzed and the water containing free chlorine is produced. The water containing free chlorine is stored in the reservoir 188. The on/off valve 189 is opened properly by the controller 187, whereby the water containing free chlorine produced by the electrolysis flows through the on/off valve 189 and the second branch 186 into the flush water supply line 183 at the downstream of the water supply valve 184 and is supplied to the urinal A181.

Apart from the operation of the present system for cleansing a urinal, tap water is also supplied to the urinal A181 by the operation of the automatic flushing system B81, or by manual operation, every time of use, whereby the surface of the urinal A181 is flushed and the standing water in the trap A182 of the urinal is renewed.

In the above system, the water containing free chlorine can be supplied to the urinal A181 at a predetermined time by controlling the timing of opening and closing the on/off valve 189. Consequently, the increase and adhesion of urease due to the action of living bacteria can be effectively suppressed and the increase in pH due to the solution of ammonia is suppressed, so that the deposition of uric stone is prevented and one of the causes of the stench is also prevented.

Since the present system for cleansing a urinal comprises the reservoir 188, a large amount of water containing free chlorine can be supplied to the urinal at a time, maintaining the free chlorine concentration as predetermined. In this case, it is also preferable to provide a pressurizing pump between the reservoir 188 and the urinal A181 so that the water containing free chlorine stored in the reservoir 188 is supplied to the urinal A181 more powerfully. The free chlorine concentration of the water containing free chlorine produced by the continuous electrolytic cell becomes higher as the flow rate becomes smaller or as the electric currency density that conditions the electrolysis is set larger. Here, when the reservoir 188 is provided as shown above, a large amount of water containing free chlorine having a fixed concentration can be supplied to the urinal at a time without varying the flow rate or raising the electric currency density. Therefore the life span of such as the electrodes of the electrolytic cell is prevented from being shorter and the necessity for maintenance work can be reduced.

In the above system for cleansing a urinal it is possible to provide a flow control valve in the first branch 182 in place of the on/off valve 185. It is also possible to provide a flow control valve together with the on/off valve 185 in series. By disposing the flow control valve, the flow rate of tap water flowing into the continuous electrolytic cell 181 can be stabilized. Furthermore, the water containing free chlorine having a desired concentration can be produced by the electrolysis by controlling the flow rate. It is also possible to connect the second branch 186 to the trap A 82 of the urinal A81 so that the water containing free chlorine stored in the reservoir 188 is supplied to the trap A182. In any of the above-described cases, the controller 187 opens and closes the on/off valve or flow control valve, or controls the opening of the flow control valve, in the same manner, and the operation and effect are the same as described previously referring to FIGS. 4 and 5.

In the above system for cleansing a urinal, the electrolytic cell 181 for producing the water containing free chlorine is employed, and the unit may be replaced by such as a device for producing the water containing bound chlorine or a device for producing ozone-water, which will be described later.

Figure 9:
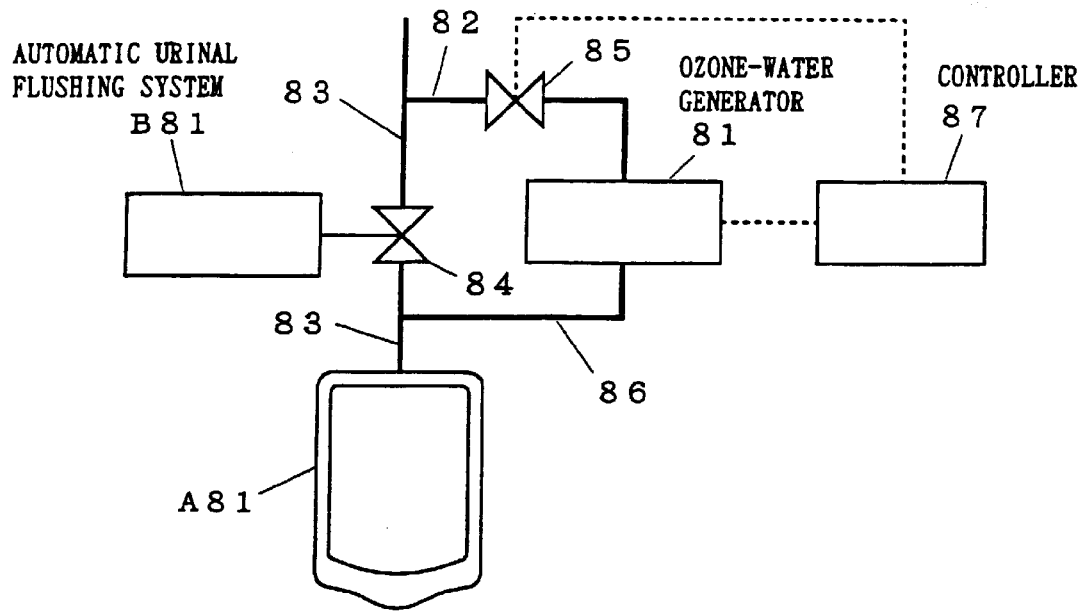
FIG. 9 shows a machinery structure of a system for cleansing a urinal comprising an ozone-water generator provided parallel to an existing flush water supply line.

FIG. 9 shows another embodiment of the system for cleansing a urinal according to the present invention. The present system comprises an ozone-water generator 81 connected by a first branch 82 with a flush water supply line 83 at an upstream of a water supply valve 84 consisting of a flush valve or the like. An on/off valve 85 consisting of a solenoid valve or the like is provided in the first branch 82. The ozone-water generator 81 is connected by a second branch 86 with the flush water supply line 83 at a downstream of the water supply valve 84. The flush water supply line 83 to which the second branch 86 is connected leads to a urinal A81. The ozone-water generator 81 and the on/off valve 85 are connected with a controller 87 having a timer. The water supply valve 84 consisting of a flush valve or the like is connected with a known automatic flushing system B81.

In the present system for cleansing a urinal, the controller 87 opens the on/off valve 85 properly as instructed by the timer, whereafter tap water flows from the flush water supply line 83 at the upstream of the water supply valve 84, via the first branch 82, into the ozone-water generator 81. On opening the on/off valve 85, or with a delay after that, the controller 87 instructs the ozone-water generator 81 to start producing ozone-water. The ozone-water produced flows through the second branch 86 into the flush water supply line 83 at the downstream of the water supply valve 84, and is supplied to the urinal A81, whereby the urinal A81 is properly sterilized and urease carried by bacteria is removed from the urinal A81 together with the bacteria. Thus the precipitation of uric stone and the formation of the stain on the urinal A81 are prevented.

Apart from the operation of the present system for cleansing a urinal, tap water is also supplied to the urinal A81 by the operation of the automatic flushing system B81, or by manual operation, every time of use, whereby the surface of the urinal A81 is flushed and the standing water in the trap of the urinal is renewed. In the present system, the ozone-water that is used for cleansing a urinal is produced by the ozone-water generator using an electrical process such as a silent discharge or an electrolysis of water, therefore it requires less maintenance work and is safer to users than the conventional flushing system using chemicals mixed with flush water.

In the present system for cleansing a urinal, the controller 87 may open the on/off valve 85 at predetermined time intervals as instructed by the timer and instruct the ozone-water generator 81 to start producing ozone-water on opening the on/off valve 85, or with a delay after that. By this method, bacteria are killed and removed at intervals, therefore the increase and adhesion of living bacteria coming from the ambient air or from other sources and attaching to the urinal can be effectively prevented. Consequently, the increase and adhesion of urease due to the action of living bacteria is effectively suppressed and the increase in pH due to the solution of ammonia is suppressed, so that the deposition of uric stone is prevented and one of the causes of the stench is also prevented.

In the present system for cleansing a urinal, the controller 87 may open the on/off valve 85 only at night as instructed by the timer and instruct the ozone-water generator 81 to start producing ozone-water on opening the on/off valve 85, or with a delay after that. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A81 at predetermined time intervals, or every time of use, by the operation of the automatic flushing system B81, or by manual operation, apart from the operation of the present system for cleansing a urinal, whereby the surface of the urinal A81 is flushed and the standing water in the trap of the urinal is renewed.

In the above case, the controller 87 may open the on/off valve 85 only at night and at predetermined time intervals, as instructed by the timer, and instruct the ozone-water generator 81 to start producing ozone-water on opening the on/off valve 85, or with a delay after that. This method is preferable in respect of saving resource and energy, since water and electricity can be saved thereby.

The above system for cleansing a urinal may also take a constitution as follows: the controller 87 is connected with the automatic flushing system B81 so that an operation signal of the system B81 is inputted to the controller 87; the timer of the controller 87 starts clocking on receiving the operation signal of the automatic flushing system B81; in case that the urinal is not used for a predetermined period of time after the last use thereof, i.e., that the urinal is not used for a predetermined period of time after the automatic flushing system B81 outputs the operation signal on the last use of the urinal A81, the controller 87 opens the on/off valve 85 as instructed by the timer and instructs the ozone-water generator 81 to start producing ozone-water on opening the on/off valve 85, or with a delay after that. By this method, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases the standing water, since tap water is supplied to the urinal A81 every time the urinal is used, by the operation of the automatic flushing system B81, or by manual operation, apart from the operation of the present system for cleansing a urinal, whereby the surface of the urinal A81 is flushed and the standing water in the trap of the urinal is renewed.

The present system for cleansing a urinal may also take a constitution as follows: the controller 87 is further connected with the automatic flushing system B81 so that an operation signal of the system B81 is inputted to the controller 87; in response to the operation signal from the automatic flushing system B81, the controller 87 opens the on/off valve 85 at every flush after use, i.e., every time the urinal A81 is used and the operation signal of the automatic flushing system B81 is outputted; on opening the on/off valve 85, or with a delay after that, the controller 87 instructs the ozone-water generator 81 to start producing ozone-water. By this method, the urinal is sterilized by the ozone-water immediately after a user urinates, whereby the generation of ammonia can be effectively suppressed, so that the deposition of uric stone is prevented and one of the causes of the stench is also prevented.

The on/off valve 85 may be opened with a delay, whereby the ozone-water is supplied to the urinal just before or just after the end of a flush after use, so that the ozone-water can spread widely over the surface of the urinal that is wet due to the flush operation by the automatic flushing system B81. As a result, the surface of the urinal can be sterilized effectively, the increase of urease can be prevented. Thus the generation of ammonia is effectively suppressed, so that the deposition of uric stone is prevented and one of the causes of the stench is also prevented.

The present system for cleansing a urinal may also take a constitution as follows: the controller 87 is further connected with the automatic flushing system B81 so that an operation signal of the system B1 is inputted to the controller 87; the timer of the controller 87 starts clocking on receiving the operation signal of the automatic flushing system B81; the on/off valve 85 is opened, as instructed by the timer, just before or just after the end of a flush after use, i.e., with a delay after the output of the operation signal of the automatic flushing system B81 subsequent to the use of the urinal A81; on opening the on/off valve 85, or with a delay after that, the controller 87 instructs the ozone-water generator 81 to start producing ozone-water. By this method, too, the ozone-water can spread widely over the surface of the urinal that is wet due to the flush operation by the automatic flushing system B81. As a result, the surface of the urinal can be sterilized effectively, the increase of urease can be prevented. Thus the generation of ammonia is effectively suppressed, so that the deposition of uric stone is prevented and one of the causes of the stench is also prevented.

Figure 10:
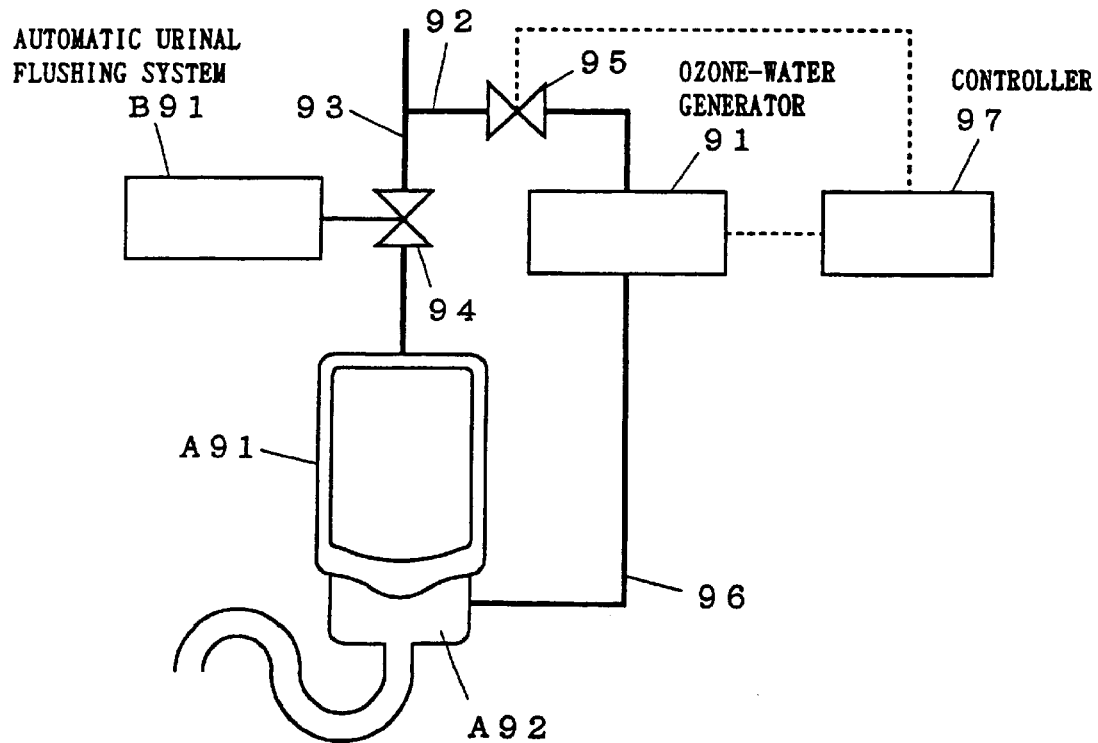
FIG. 10 shows a machinery structure of a system for cleansing a urinal comprising an ozone-water generator provided parallel to an existing flush water supply line, and having a constitution that the ozone-water is supplied to the trap of the urinal.

FIG. 10 shows another embodiment of the system for cleansing a urinal according to the present invention. The present system comprises an ozone-water generator 91 connected by a first branch 92 with a flush water supply line 93 at an upstream of a water supply valve 94 consisting of a flush valve or the like. An on/off valve 95 consisting of a solenoid valve or the like is provided in the first branch 92. The ozone-water generator 91 is connected by a second branch 96 with the trap A92 of the urinal. The ozone-water generator 91 and the on/off valve 95 are connected with a controller 97 having a timer. The water supply valve 94 consisting of a flush valve or the like is connected with a known automatic flushing system B91.

In the present system for cleansing a urinal, the controller 97 opens the on/off valve 95 properly as instructed by the timer, whereafter tap water flows from the flush water supply line 93 at the upstream of the water supply valve 94, via the first branch 92, into the ozone-water generator 91. On opening the on/off valve 95, or with a delay after that, the controller 97 instructs the ozone-water generator 91 to start producing ozone-water. The ozone-water produced flows through the second branch 96 into the trap A92, whereby the standing water of the urinal A91 is properly sterilized and urease carried by bacteria is removed from the urinal A91 together with the bacteria. Thus the precipitation of uric stone and the formation of yellowish stain are prevented in the trap A92 where the yellowish stain sticks most outstandingly.

Apart from the operation of the present system for cleansing a urinal, tap water is also supplied to the urinal A91 by the operation of the automatic flushing system B91, or by manual operation, every time of use, whereby the surface of the urinal A91 is flushed and the standing water in the trap A92 is renewed. In the present system, the ozone-water that is used for cleansing a urinal is produced by an electrical process such as a silent discharge or an electrolysis of water, therefore it requires less maintenance work and is safer to users than the conventional flushing system using chemicals mixed with flush water.

The present system for cleansing a urinal may also take a constitution as follows: the controller 97 opens the on/off valve 95 at predetermined time intervals as instructed by the timer, and instructs the ozone-water generator 91 to start producing ozone-water on opening the on/off valve 95, or with a delay after that. By this method, living bacteria are killed and removed at intervals, therefore the increase and adhesion of living bacteria coming from the ambient air or from other sources into the standing water in the trap A92 can be effectively prevented. Consequently, the increase and adhesion of urease due to the action of living bacteria can be effectively suppressed and the increase in pH due to the solution of ammonia is suppressed, so that the deposition of uric stone is prevented and one of the causes of the stench is also prevented.

The present system for cleansing a urinal may also take a constitution as follows: the controller 97 opens the on/off valve 95 only at night as instructed by the timer and instructs the ozone-water generator 91 to start producing ozone-water on opening the on/off valve 95, or with a delay after that. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A91 at a predetermined time intervals, or every time of use, by the operation of the automatic flushing system B91, or by manual operation, apart from the operation of the present system for cleansing a urinal, whereby the surface of the urinal A91 is flushed and the standing water in the trap A92 is renewed.

In this case, the controller 97 may open the on/off valve 95 only at night and at predetermined time intervals as instructed by the timer and instruct the ozone-water generator 91 to start producing ozone-water on opening the on/off valve 95, or with a delay after that. This method is preferable in respect of saving resource and energy, since water and electricity can be saved thereby.

The above system for cleansing a urinal may also take a constitution as follows: the controller 97 is connected with the automatic flushing system B91 so that an operation signal of the system B91 is inputted to the controller 97; the timer of the controller 97 starts clocking on receiving the operation signal of the automatic flushing system B91; in case that the urinal is not used for a predetermined period of time after the last use thereof, i.e., the urinal is not used for a predetermined period of time after the automatic flushing system B91 outputs the operation signal on the last use of the urinal A91, the controller 97 opens the on/off valve 95 as instructed by the timer; on opening the on/off valve 95, or with a delay after that, the controller 97 instructs the ozone-water generator 91 to start producing ozone-water. By this method, similar to the above case, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A91 every time the urinal is used by the operation of the automatic flushing system B91, or by manual operation, apart from the operation of the present system for cleansing a urinal, whereby the surface of the urinal A91 is flushed and the standing water in the trap A92 is renewed.

The present system for cleansing a urinal may also take a constitution as follows: the controller 97 is further connected with the automatic flushing system B91 so that an operation signal of the system B91 is inputted to the controller 97; in response to the operation signal from the automatic flushing system B91, the controller 97 opens the on/off valve 95 at every flush after use, i.e., every time the urinal A91 is used and the operation signal of the automatic flushing system B91 is outputted; on opening the on/off valve 95, or with a delay after that, the controller 97 instructs the ozone-water generator 91 to start producing ozone-water. By this method, the urinal is sterilized by the ozone-water just after the user urinates, whereby the generation of ammonia can be effectively suppressed, so that the deposition of uric stone is prevented and one of the causes of the stench is also prevented.

Figure 11:
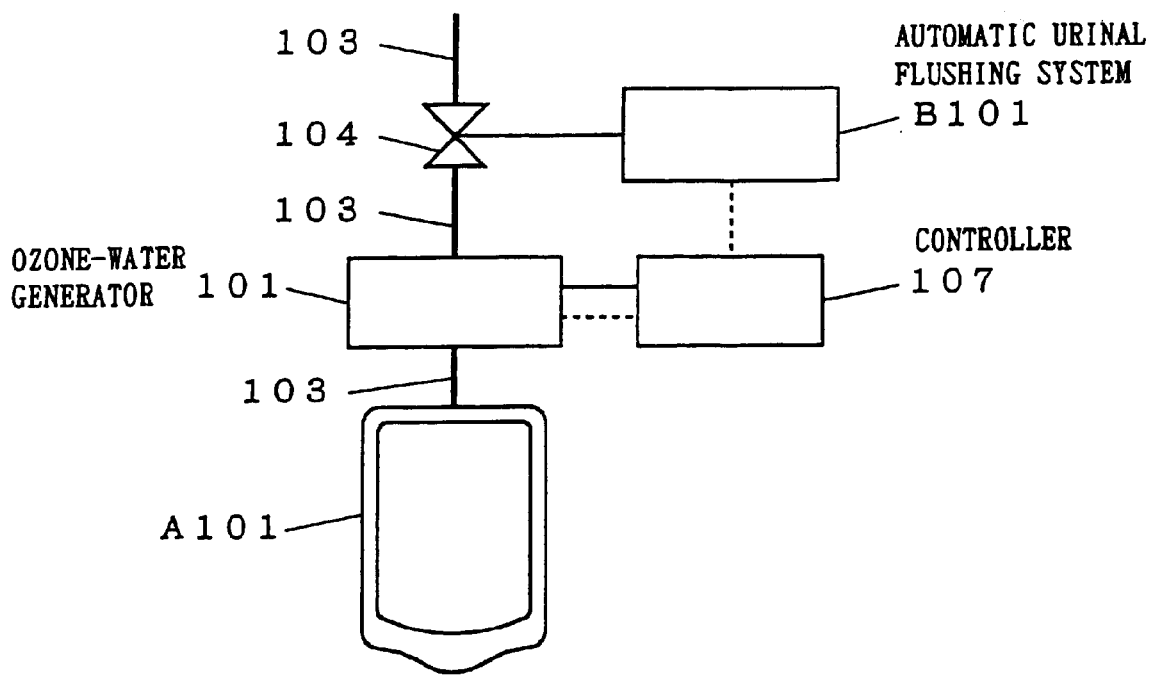
FIG. 11 shows a machinery structure of a system for cleansing a urinal comprising an ozone-water generator provided in an existing flush water supply line.

FIG. 11 shows another embodiment of the system for cleansing a urinal according to the present invention. The present system comprises an ozone-water generator 101 provided in a flush water supply line 103 at a downstream of a water supply valve 104 consisting of a flush valve or the like. The ozone-water generator 101 is connected with a controller 107. The water supply valve 104 is connected with a known automatic flushing system B101. The flush water supply line 103 is connected to a urinal A101.

In the present system for cleansing a urinal, the water supply valve 104 is opened by the operation of the automatic flushing system B101, whereby tap water flows via the flush water supply line 103 into the ozone-water generator 101. The control signal to the water supply valve 104 is sent also from the automatic flushing system B101 to the controller 107. The controller 107, on receiving the signal, outputs an operation signal to the ozone-water generator 101, and the ozone-water generator 101 starts producing ozone-water from the water flowing therein. The ozone-water produced is supplied via the flush water supply line 103 to the urinal A101.

By this method, the ozone-water is supplied every time the urinal A101 is used, whereby the sterilization and the inhibition of the enzymatic activity of urease can be accomplished and the generation of ammonia can be effectively suppressed immediately after a user urinates, so that the deposition of uric stone is prevented and one of the causes of the stench is also prevented.

The present system for cleansing a urinal also requires less maintenance work and is safer to users than the conventional flushing system using chemicals mixed with flush water.

The present system for cleansing a urinal may be constituted as follows: a timer is provided to the controller 107; after receiving a control signal to the water supply valve 104 from the automatic flushing system B101, the controller 107 instructs the ozone-water generator 101 to start producing ozone-water just before the end of the period when the water supply valve 104 is open; and the ozone-water produced is supplied to the urinal A101. By this method, the ozone-water is supplied to the urinal A101 just before or just after the end of a flush after use, so that the ozone-water can spread widely over the surface of the urinal that is wet due to the flush operation by the automatic flushing system B101. Accordingly, the surface of the urinal can be sterilized effectively and the increase of urease can be prevented, so that the deposition of uric stone is prevented and one of the causes of the stench is also prevented.

Figure 12:
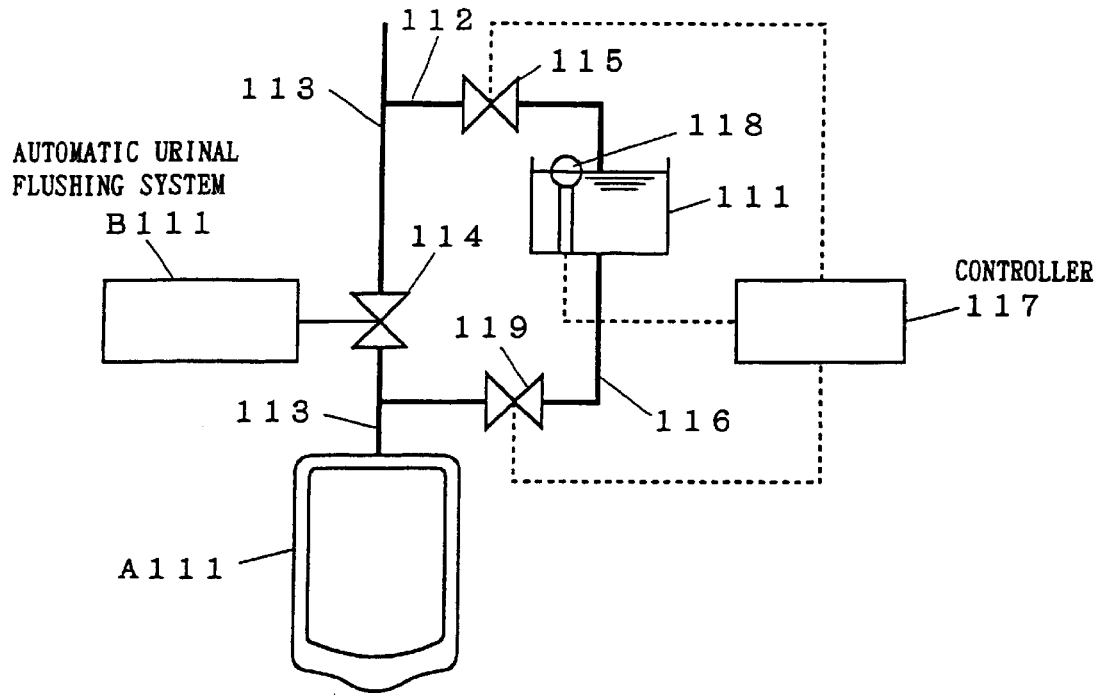
FIG. 12 shows a machinery structure of a system for cleansing a urinal comprising an ozone-water generator provided parallel to an existing flush water supply line, and having a constitution that a flow control valve for controlling tap water flowing into the ozone-water generator and an on/off valve for passing and stopping the ozone-water flowing from the ozone-water generator are controlled, or opened and closed, as instructed by a controller.

FIG. 12 shows another embodiment of the system for cleansing a urinal according to the present invention. The present system comprises an ozone-water generator 111 connected by a first branch 112 with a flush water supply line 113 at an upstream of a water supply valve 114 consisting of a flush valve or the like. A flow control valve 115 is provided in the first branch 112. The ozone-water generator 111 is connected by a second branch 116 with the flush water supply line 113 at a downstream of the water supply valve 114. An on/off valve 119 is provided in the second branch 116. The flush water supply line 113 to which the second branch 116 is connected leads to the urinal A111. A float sensor 118 in the ozone-water generator 111, the flow control valve 115 and the on/off valve 119 are connected with a controller 117.

In the present system for cleansing a urinal, tap water constantly flows at a small flow rate from the flush water supply line 113 at the upstream of the water supply valve 114, via the first branch 112 and the flow control valve 11 5, into the ozone-water generator 111. The water level in the ozone-water generator 111 is detected by the float sensor 118. When the water in the ozone-water generator 111 reaches a predetermined level, the controller 117, on receiving a detection signal from the float sensor 118, closes the flow control valve 115, and an ozone-water is produced from the water stored in the ozone-water generator 111. After producing the ozone-water, the controller 117 opens the on/off valve 119, whereafter the ozone-water produced flows through the on/off valve 119 and the second branch 116 into the flush water supply line 113 at the downstream of the water supply valve 114 and is supplied to the urinal A111.

The time when the water in the ozone-water generator reaches the predetermined level may be detected either by measuring the water level directly by the float sensor 118, as shown above, or by measuring the elapsing time from a time the on/off valve is opened.

Apart from the operation of the present system for cleansing a urinal, tap water is supplied to the urinal A111 by the automatic flushing system B111, or by manual operation, every time of use, whereby the surface of the urinal A111 is flushed and the standing water in the trap of the urinal is renewed.

Also in the present system for cleansing a urinal, the ozone-water that is used for cleansing a urinal is produced by an electrical process such as silent discharge or electrolysis of water, therefore it requires less maintenance work and is safer to users than the conventional flushing system using chemicals mixed with flush water.

By the above system, the ozone-water can be supplied to the urinal A111 at predetermined time intervals by setting the flow rate of the flow control valve 115 properly. Consequently, the increase and adhesion of urease due to the action of living bacteria can be effectively suppressed and the increase in pH due to the solution of ammonia is suppressed, so that the deposition of uric stone is prevented and one of the causes of the stench is also prevented. Furthermore, the present system consumes less water and electricity than a system whereby water is supplied at all times and therefore saves resource and energy, since the ozone-water is produced at intervals.

The system for cleansing a urinal shown in FIG. 12 may also take a constitution as follows: the flow control valve 115 is connected with the controller 117; a timer is provided in the controller 117; the flow control valve 115 is opened properly and regulated at a predetermined flow rate, whereafter tap water constantly flows at a small flow rate from the flush water supply line 113 at the upstream of the water supply valve 114, via the first branch 112 and the flow control valve 115, into the ozone-water generator 111; after that, when the on/off valve 119 is opened, the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level, the on/off valve 119 is closed and at the same time, or with a delay, the flow control valve 115 is closed.

In this case, tap water constantly flows at a small flow rate from the flush water supply line 113 at the upstream of the water supply valve 114, via the first branch 112 and the flow control valve 115, into the ozone-water generator 111, whereafter the on/off valve 119 is opened, and the ozone-water produced flows through the on/off valve 119 and the second branch 116 into the flush water supply line 113 at the downstream of the water supply valve 114 and is supplied to the urinal A111. In this process, the operation is the same as described above, that is: the water level in the ozone-water generator 111 is detected by the float sensor 118, and when the water in the ozone-water generator 111 reaches a predetermined level, the controller 117, on receiving a detection signal from the float sensor 118, closes the flow control valve 115. Then, the ozone-water is produced from the water stored in the ozone-water generator 111. After producing the ozone-water, the controller 117 opens the on/off valve 119.

By this method, the flow control valve 115 is opened to supply the ozone-water to the urinal A111 only at a required time as instructed by the timer, so that resource and energy can be saved since it consumes less water and electricity than a system whereby water is supplied at all times.

The system for cleansing a urinal shown in FIG. 12 may also take a constitution as follows: the flow control valve 115 is connected with the controller 117; a timer is provided in the controller 117, the controller 117 opens the flow control valve 115 only at night and regulates it at a predetermined flow rate; tap water constantly flows at a small flow rate from the flush water supply line 113 at the upstream of the water supply valve 114, via the first branch 112 and the flow control valve 115, into the ozone-water generator 111, then the on/off valve 119 is opened, whereby the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level, the on/off valve 119 is closed and at the same time, or with a delay, the flow control valve 115 is closed.

By this method, the ozone-water is supplied to the urinal A11 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A111 at predetermined time intervals, or every time of use, by the operation of the automatic flushing system B111, or by manual operation, apart from the operation of the present system for cleansing a urinal, whereby the surface of the urinal A111 is flushed and the standing water in the trap of the urinal is renewed.

The system for cleansing a urinal shown in FIG. 12 may also take a constitution as follows: the flow control valve 115 is connected with the controller 117; a timer is provided in the controller 117; the controller 117 is connected with the automatic flushing system B111 so that an operation signal of the system B111 is inputted to the controller 117; the timer of the controller 117 starts clocking on receiving the operation signal of the automatic flushing system B11; in case that the urinal A111 is not used for a predetermined period of time after the last use thereof, i.e., that no operation signal of the automatic flushing system B111 is outputted for the predetermined period of time after the system B111 outputs the operation signal on the last use of the urinal A111, the controller 117 opens the flow control valve 115 as instructed by the timer, and regulates it at a predetermined flow rate; whereby tap water constantly flows at a small flow rate from the flush water supply line 113 at the upstream of the water supply valve 114, via the first branch 112 and the flow control valve 115, into the ozone-water generator 111; then the on/off valve 119 is opened, whereby the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level, the on/off valve 119 is closed and at the same time, or with a delay, the flow control valve 115 is closed.

By this method, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A111 at predetermined time intervals, or every time of use, by the operation of the automatic flushing system B111, or by manual operation, apart from the operation of the present system for cleansing a urinal, whereby the surface of the urinal A111 is flushed and the standing water in the trap of the urinal is renewed.

The system for cleansing a urinal shown in FIG. 12 may also take a constitution as follows: the flow control valve 115 is connected with the controller 117; a timer is provided in the controller 117; the controller 117 is connected with the automatic flushing system B111 so that an operation signal of the system B111 is inputted to the controller 117; in response to the operation signal of the automatic flushing system B111, the controller 117 opens the flow control valve 115 as instructed by the timer and regulates it at a predetermined flow rate at every flush after use, i.e., every time the urinal A111 is used and the operation signal of the automatic flushing system B111 is outputted; whereby tap water constantly flows at a small flow rate from the flush water supply line 113 at the upstream of the water supply valve 114, via the first branch 112 and the flow control valve 115, into the ozone-water generator 111; then the on/off valve 119 is opened, whereby the ozone-water produced flows through the on/off valve 119 and the second branch 116 into the flush water supply line 113 at the downstream of the water supply valve 114, and is supplied to the urinal A11; when the water in the ozone-water generator 111 reaches a predetermined low level, the on/off valve 119 is closed and at the same time, or with a delay, the flow control valve 115 is closed.

By this method, the ozone-water is supplied to the urinal while the surface of the urinal is wet after the flush operation by the automatic flushing system B111 subsequent to a use of the urinal, so that the ozone-water can spread widely over the surface of the urinal that is wet due to the flush operation. As a result, the surface of the urinal can be sterilized effectively, the increase of urease can be prevented. Thus the generation of ammonia is effectively suppressed, so that the deposition of uric stone is prevented and one of the causes of the stench is also prevented.

The system for cleansing a urinal shown in FIG. 12 may also take a constitution as follows: an on/off valve G is provided in the first branch 112 at an upstream of the flow control valve 115; the on/off valve G is connected with the controller 117; a timer is provided in the controller 117; the flow control valve 115 is preset at a predetermined flow rate and the on/off valve G is properly opened to let tap water constantly flow at a small flow rate from the flush water supply line 113 at the upstream of the water supply valve 114, via the first branch 112 and the flow control valve 115, into the ozone-water generator 111; when the on/off valve 119 is opened, the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level, the on/off valve 119 is closed and at the same time, or with a delay, the on/off valve G is closed.

In this case, tap water constantly flows at a small flow rate from the flush water supply line 113 at the upstream of the water supply valve 114, via the first branch 112, the on/off valve G and the flow control valve 115, into the ozone-water generator 111, whereafter the on/off valve 119 is opened and the ozone-water produced flows through the on/off valve 119 and the second branch 116 into the flush water supply line 113 at the downstream of the water supply valve 114 and is supplied to the urinal A111. In this process, the operation is the same as described above, that is: the water level in the ozone-water generator 111 is detected by the float sensor 118, and when the water in the ozone-water generator 111 reaches a predetermined level, the controller 117, on receiving a detection signal from the float sensor 118, closes the on/off valve G. Then the ozone-water is produced from the water stored in the ozone-water generator 111. After producing the ozone-water, the controller 117 opens the on/off valve 119.

By this method, the on/off valve G is opened to supply the ozone-water to the urinal A111 only at a required time as instructed by the timer, so that resource and energy can be saved since it consumes less water and electricity than a system whereby water is supplied at all times.

Furthermore, since the on/off valve G is provided, there is no need to control the flow rate every time of opening and closing, and accordingly no need to provide the controller with a flow control mechanism.

The system for cleansing a urinal shown in FIG. 12 may also take a constitution as follows: an on/off valve G is provided in the first branch 112 at an upstream of the flow control valve 11 5; the on/off valve G is connected with the controller 117; a timer is provided in the controller 117; the flow control valve 115 is preset at a predetermined flow rate and the on/off valve G is opened only at night to let tap water constantly flow at a small flow rate from the flush water supply line 113 at the upstream of the water supply valve 114, via the first branch 112, the on/off valve G and the flow control valve 115, into the ozone-water generator 111; when the on/off valve 119 is opened, the ozone-water produced flows through the on/off valve 119 and the second branch 116 into the flush water supply line 113 at the downstream of the water supply valve 114, and is supplied to the urinal A11; when the water in the ozone-water generator 111 reaches a predetermined low level, the on/off valve 119 is closed and at the same time, or with a delay, the on/off valve G is closed.

When the above method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A111 at predetermined time intervals, or every time of use, by the operation of the automatic flushing system B111, or by manual operation, apart from the operation of the present system for cleansing a urinal, whereby the surface of the urinal A111 is flushed and the standing water in the trap of the urinal is renewed. Furthermore, since the on/off valve G is provided, there is no need to control the flow rate every time of opening and closing, and accordingly no need to provide the controller with a flow control mechanism.

The system for cleansing a urinal shown in FIG. 12 may also take a constitution as follows: an on/off valve G is provided in the first branch 112 at an upstream of the flow control valve 115; the on/off valve G is connected with the controller 117; the flow control valve 115 is preset at a predetermined flow rate; a timer is provided in the controller 117; the controller 117 is connected with the automatic flushing system B111 so that an operation signal of the system B111 is inputted to the controller 117; the timer of the controller 117 starts clocking on receiving the operation signal of the automatic flushing system B11; in case that the urinal A11 is not used for a predetermined period of time after the last use thereof, i.e., that no operation signal of the automatic flushing system B111 is outputted for the predetermined period of time after the system B111 outputs the operation signal on the last use of the urinal A111, the controller 117 opens the on/off valve G as instructed by the timer; whereby tap water constantly flows at a small flow rate from the flush water supply line 113 at the upstream of the water supply valve 114, via the first branch 112, the on/off valve G and the flow control valve 115, into the ozone-water generator 111; when the on/off valve 119 is opened, the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level, the on/off valve 119 is closed and at the same time, or with a delay, the on/off valve G is closed.

By this method, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A111 every time of use by the operation of the automatic flushing system B111, or by manual operation, apart from the operation of the present system for cleansing a urinal, whereby the surface of the urinal A111 is flushed and the standing water in the trap of the urinal is renewed. Furthermore, since the on/off valve G is provided, there is no need to control the flow rate every time of opening and closing, and accordingly no need to provide the controller with a flow control mechanism.

The system for cleansing a urinal shown in FIG. 12 may also take a constitution as follows: an on/off valve G is provided in the first branch 112 at an upstream of the flow control valve 115; the on/off valve G is connected with the controller 117; the flow control valve 115 is preset at a predetermined flow rate; a timer is provided in the controller 117; the controller 117 is connected with the automatic flushing system B111 so that an operation signal of the system B111 is inputted to the controller 117; in response to the operation signal of the automatic flushing system B111, the controller 117 opens the on/off valve G at every flush after use, i.e., every time the urinal A111 is used and the operation signal of the automatic flushing system B111 is outputted, so that tap water constantly flows at a small flow rate from the flush water supply line 113 at the upstream of the water supply valve 114, via the first branch 112, the on/off valve G and the flow control valve 115, into the ozone-water generator 111; when the on/off valve 119 is opened, the ozone-water produced flows through the on/off valve 119 and the second branch 116 into the flush water supply line 113 at the downstream of the water supply valve 114, and is supplied to the urinal A111; when the water in the ozone-water generator 111 reaches a predetermined low level lower, the on/off valve 119 is closed and at the same time, or with a delay, the on/off valve G is closed.

By this method, the ozone-water is supplied to the urinal while the surface of the urinal is wet after the flush operation by the automatic flushing system B111 subsequent to a use of the urinal, so that the ozone-water can spread widely over the surface of the urinal that is wet due to the flush operation. As a result, the surface of the urinal can be sterilized effectively, the increase of urease can be prevented. Thus the generation of ammonia is effectively suppressed, so that the deposition of uric stone is prevented and one of the causes of the stench is also prevented. Furthermore, since the on/off valve G is provided, there is no need to control the flow rate every time of opening and closing, and accordingly no need to provide the controller with a flow control mechanism.

Figure 13:
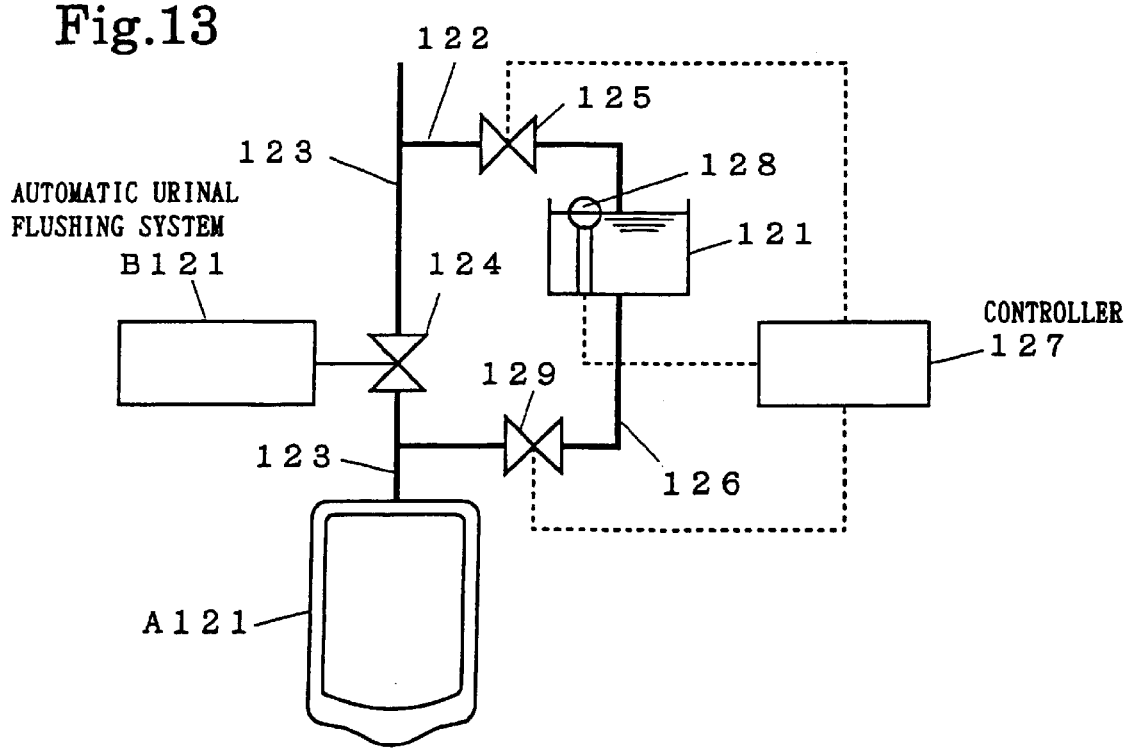
FIG. 13 shows a machinery structure of a system for cleansing a urinal comprising an ozone-water generator provided parallel to an existing flush water supply line, and having a constitution that an on/off valve for passing and stopping tap water flowing into the ozone-water generator and an on/off valve for passing and stopping the ozone-water flowing from the ozone-water generator are opened and closed as instructed by a controller.

FIG. 13 shows another embodiment of the system for cleansing a urinal according to the present invention. The present system comprises an ozone-water generator 121 having a float sensor 128. The ozone-water generator 121 is connected by a first branch 122 with a flush water supply line 123 at an upstream of a water supply valve 124 consisting of a flush valve or the like. An on/off valve 125 is provided in the first branch 122. The ozone-water generator 121 is connected by a second branch 126 with the flush water supply line 123 at a downstream of the water supply valve 124. An on/off valve 129 is provided in the second branch 126. The flush water supply line 123 to which the second branch 126 is connected leads to a urinal A121. The ozone-water generator 121 is connected with a controller 127.

In the present system for cleansing a urinal, tap water constantly flows from the flush water supply line 123 at the upstream of the water supply valve 124, via the first branch 122 and the on/off valve 125, into the ozone-water generator 121. The water level in the ozone-water generator is detected by the float sensor 128. When the water in the ozone-water generator 121 reaches a predetermined level, the controller 127, on receiving a detection signal from the float sensor 128, closes the on/off valve 125. The controller 127 having a timer instructs the ozone-water generator 121 to start producing ozone-water only in case that the water level in the ozone-water generator 121 is higher than predetermined during a predetermined period of time. After producing the ozone-water, the controller 127 opens the on/off valve 129 immediately, whereby the ozone-water produced flows through the on/off valve 129 and the second branch 126 into the flush water supply line 123 at the downstream of the water supply valve 124 and is supplied to the urinal A121.

The time when the water in the ozone-water generator reaches the predetermined level may be detected either by measuring the water level directly by the float sensor 128, as shown above, or by measuring the elapsing time from a time the on/off valve 125 in the first branch 125 or the on/off valve 129 in the second branch 126 is opened.

Apart from the operation of the present system for cleansing a urinal, tap water is supplied to the urinal A121 by the automatic flushing system B121, or by manual operation, every time of use, whereby the surface of the urinal A121 is flushed and the standing water in the trap of the urinal is renewed.

Also in the present system for cleansing a urinal, the ozone-water that is used for cleansing a urinal is produced by an electrical process such as a silent discharge or an electrolysis of water, therefore it requires less maintenance work and is safer to users than the conventional flushing system using chemicals mixed with flush water.

In the above system, the ozone-water is produced and supplied to the urinal A121 as instructed by the timer. Consequently, the increase and adhesion of urease due to the action of living bacteria can be effectively suppressed and the increase in pH due to the solution of ammonia is suppressed, so that the deposition of uric stone is prevented and one of the causes of the stench is also prevented.

In the above system for cleansing a urinal, it is possible to determine the period for producing ozone-water at predetermined time intervals as instructed by the timer. By this method, the ozone-water is supplied to the urinal A121 at predetermined time intervals, so that resource and energy can be saved since it consumes less water and electricity than a system whereby water is supplied at all times.

In the above system for cleansing a urinal, it is possible to determine the period for producing ozone-water only at night as instructed by the timer, whereby the ozone-water is supplied to the urinal A121 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A121 at predetermined time intervals, or every time of use, by the operation of the automatic flushing system B121, or by manual operation, apart from the operation of the present system for cleansing a urinal, whereby the surface of the urinal A121 is flushed and the standing water in the trap of the urinal is renewed.

The above system for cleansing a urinal may also take a constitution as follows: the controller 127 is further connected with the automatic flushing system B121 so that an operation signal of the automatic flushing system B121 is inputted to the controller 127; the timer of the controller 127 starts clocking on receiving the operation signal of the automatic flushing system B121; in case that the urinal A121 is not used for a predetermined period of time after the last use thereof, i.e., that no operation signal of the automatic flushing system B121 is outputted for the predetermined period of time after the system B121 outputs the operation signal on the last use of the urinal A121, the controller 127 determines the period for producing ozone-water as instructed by the timer. By this method, the ozone-water is supplied to the urinal A121 only in case that the urinal A121 is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A121 at predetermined time intervals, or every time of use, by the operation of the automatic flushing system B121, or by manual operation, apart from the operation of the present system for cleansing a urinal, whereby the surface of the urinal A121 is flushed and the standing water in the trap of the urinal is renewed.

The above system for cleansing a urinal may also take a constitution as follows: the controller 127 is further connected with the automatic flushing system B121 so that an operation signal of the automatic flushing system B121 is inputted to the controller 127; in response to the operation signal of the automatic flushing system B121, the controller 127 determines the period for producing ozone-water at every flush after use, i.e., every time the urinal A121 is used and the operation signal of the automatic flushing system B121 is outputted. By this method, the ozone-water is supplied to the urinal at every flush after use, therefore the ozone-water can be supplied while the surface of the urinal is wet after the flush operation by the automatic flushing system B121 subsequent to a use of the urinal, so that the ozone-water can spread widely over the surface of the urinal that is wet due to the flush operation. As a result, the surface of the urinal can be sterilized effectively, the increase of urease can be prevented. Thus the generation of ammonia is effectively suppressed, so that the deposition of uric stone is prevented and one of the causes of the stench is also prevented.

Figure 14:
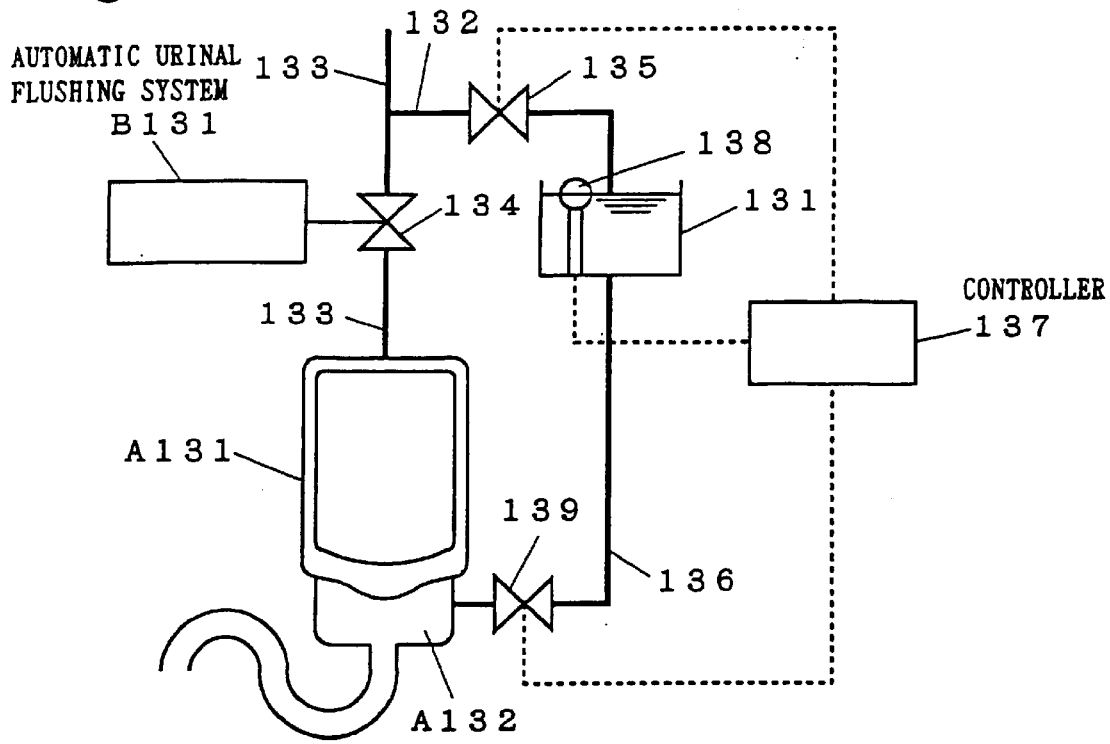
FIG. 14 shows a machinery structure of a system for cleansing a urinal comprising an ozone-water generator provided parallel to an existing flush water supply line, and having a constitution that a flow control valve for controlling tap water flowing into the ozone-water generator and an on/off valve for passing and stopping the ozone-water flowing from the ozone-water generator are controlled, or opened and closed, as instructed by a controller, and that the ozone-water is supplied to the trap of the urinal.

FIG. 14 shows another embodiment of the system for cleansing a urinal according to the present invention. The present system comprises an ozone-water generator 131 that is connected by a first branch 132 with a flush water supply line 133 at an upstream of a water supply valve 134 consisting of a flush valve or the like. A flow control valve 135 is provided in the first branch 132. The ozone-water generator 131 is connected by a second branch 136 with the trap A132 of the urinal. An on/off valve 139 is provided in the second branch 136. A float sensor 138 in the ozone-water generator 131, the flow control valve 135 and the on/off valve 139 are connected with a controller 137.

In the present system for cleansing a urinal, tap water constantly flows at a small flow rate from the flush water supply line 133 at the upstream of the water supply valve 134, via the first branch 132 and the flow control valve 135, into the ozone-water generator 131. The water level in the ozone-water generator 131 is detected by the float sensor 138. When the water in the ozone-water generator 131 reaches a predetermined level, the controller 137, on receiving a detection signal from the float sensor 138, closes the flow control valve 135, and the ozone-water is produced from the water stored in the ozone-water generator 131. After the ozone-water is produced, the controller 137 opens the on/off valve 139, whereby the ozone-water produced flows through the on/off valve 139 and the second branch 136 into the trap A132. Thus the standing water of the urinal A131 is properly sterilized and urease carried by bacteria is removed from the urinal A131 together with the bacteria. Therefore the precipitation of uric stone and the formation of yellowish stain are prevented at the trap A1 32 where yellowish stain sticks most outstandingly.

The time when the water in the ozone-water generator reaches the predetermined level may be detected either by measuring the water level directly by the float sensor 138, as shown above, or by measuring the elapsing time from a time the on/off valve 139 in the second branch is opened.

Apart from the operation of the present system for cleansing a urinal, tap water is supplied to the urinal A131 by the automatic flushing system B131, or by manual operation, every time of use, whereby the surface of the urinal A131 is flushed and the standing water in the trap A132 is renewed.

Also in the present system for cleansing a urinal, the ozone-water that is used for cleansing a urinal is produced by an electrical process such as a silent discharge or an electrolysis of water, therefore it requires less maintenance work and is safer to users than the conventional flushing system using chemicals mixed with flush water.

By the above system, the ozone-water can be supplied to the trap A 32 at predetermined time intervals by setting the flow rate of the flow control valve 135 properly. Consequently, the increase and adhesion of urease due to the action of living bacteria can be effectively suppressed and the increase in pH due to the solution of ammonia is suppressed, so that the deposition of uric stone is prevented and one of the causes of the stench is also prevented. Furthermore, the present system consumes less water and electricity than a system whereby water is supplied at all times and therefore saves resource and energy, since the ozone-water is produced at intervals.

The system for cleansing a urinal shown in FIG. 14 may also take a constitution as follows: the flow control valve 135 is connected with the controller 137; a timer is provided in the controller 137; the flow control valve 135 is opened properly and regulated at a predetermined flow rate, whereafter tap water constantly flows at a small flow rate from the flush water supply line 133 at the upstream of the water supply valve 134, via the first branch 132 and the flow control valve 135, into the ozone-water generator 131; when the on/off valve 139 is opened, the ozone-water produced flows through the on/off valve 139 and the second branch 136 into the trap A132; when the water in the ozone-water generator 131 reaches a predetermined low level, the on/off valve 139 is closed and at the same time, or with a delay, the flow control valve 135 is closed.

In this case, tap water constantly flows at a small flow rate from the flush water supply line 133 at the upstream of the water supply valve 134, via the first branch 132 and the flow control valve 135, into the ozone-water generator 131, whereafter the on/off valve 139 is opened and the ozone-water produced flows through the on/off valve 139 and the second branch 136 into the trap A132. In this process, the operation is the same as described above, that is: the water level in the ozone-water generator 131 is detected by the float sensor 138, and when the water in the ozone-water generator 131 reaches a predetermined level, the controller 137, on receiving a detection signal from the float sensor 138, closes the flow control valve 135, and then the ozone-water is produced from the water stored in the ozone-water generator 131, and after producing the ozone-water, the controller 137 opens the on/off valve 139.

By this method, the flow control valve 135 can be opened to supply the ozone-water to the trap A132 only at a required time as instructed by the timer, so that resource and energy can be saved since it consumes less water and electricity than a system whereby water is supplied at all times.

The system for cleansing a urinal shown in FIG. 14 may also take a constitution as follows: the flow control valve 135 is connected with the controller 137; a timer is provided in the controller 137; the controller 137 opens the flow control valve 135 only at night and adjusts it at a predetermined flow rate, whereby tap water constantly flows at a small flow rate from the flush water supply line 133 at the upstream of the water supply valve 134, via the first branch 132 and the flow control valve 135, into the ozone-water generator 131; when the on/off valve 139 is opened, the ozone-water produced flows through the on/off valve 139 and the second branch 136 into the trap A132; when the water in the ozone-water generator 131 reaches a predetermined low level, the on/off valve 139 is closed and at the same time, or with a delay, the flow control valve 135 is closed.

By this method, the ozone-water is supplied to the trap A132 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A131 at predetermined time intervals, or every time of use, by the operation of the automatic flushing system B131, or by manual operation, apart from the operation of the present system for cleansing a urinal, whereby the surface of the urinal A131 is flushed and the standing water in the trap A 32 is renewed.

The system for cleansing a urinal shown in FIG. 14 may also take a constitution as follows: the flow control valve 135 is connected with the controller 137; a timer is provided in the controller 137; the controller 137 is connected with the automatic flushing system B131 so that an operation signal of the system B131 is inputted to the controller 137; the timer of the controller 137 starts clocking on receiving the operation signal of the automatic flushing system B131; in case that the urinal is not used for a predetermined period of time after the last use thereof, i.e., that no operation signal of the automatic flushing system B131 is outputted for the predetermined period of time after the system B131 outputs the operation signal on the last use of the urinal A131, the controller 137 opens the flow control valve 135 as instructed by the timer and adjusts it at a predetermined flow rate; whereby tap water constantly flows at a small flow rate from the flush water supply line 133 at the upstream of the water supply valve 134, via the first branch 132 and the flow control valve 135, into the ozone-water generator 131; then the on/off valve 139 is opened, whereby the ozone-water produced flows through the on/off valve 139 and the second branch 136 into the trap A132; when the water in the ozone-water generator 131 reaches a predetermined low level, the on/off valve 139 is closed and at the same time, or with a delay, the flow control valve 135 is closed.

By this method, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A131 at predetermined time intervals, or every time of use, by the operation of the automatic flushing system B131, or by manual operation, apart from the operation of the present system for cleansing a urinal, whereby the surface of the urinal A131 is flushed and the standing water in the trap A132 is renewed.

The system for cleansing a urinal shown in FIG. 14 may also take a constitution as follows: an on/off valve H is provided in the first branch 132 at an upstream of the flow control valve 135; the on/off valve H is connected with the controller 137; a timer is provided in the controller 137; the flow control valve 135 is preset at a predetermined flow rate and the on/off valve H is properly opened; whereafter tap water constantly flows at a small flow rate from the flush water supply line 133 at the upstream of the water supply valve 134, via the first branch 132, on/off valve H and the flow control valve 135, into the ozone-water generator 131; when the on/off valve 139 is opened, the ozone-water produced flows through the on/off valve 139 and the second branch 136 into the trap A132; when the water in the ozone-water generator 131 reaches a predetermined low level, the on/off valve 139 is closed and at the same time, or with a delay, the on/off valve H is closed.

In this case, tap water constantly flows at a small flow rate from the flush water supply line 133 at the upstream of the water supply valve 134, via the first branch 132, the on/off valve H and the flow control valve 135, into the ozone-water generator 131, whereafter the on/off valve 139 is opened and the ozone-water produced flows through the on/off valve 139 and the second branch 136 into the trap A132. In this process, the operation is the same as described above, that is: the water level in the ozone-water generator 131 is detected by the float sensor 138, and when the water in the ozone-water generator 131 reaches a predetermined level, the controller 137, on receiving a detection signal from the float sensor 138, closes the on/off valve H. Then the ozone-water is produced from the water stored in the ozone-water generator 131, and after producing the ozone-water, the controller 137 opens the on/off valve 139.

By this method, the on/off valve H is opened to supply the ozone-water to the trap A132 only at a required time as instructed by the timer, so that resource and energy can be saved since it consumes less water and electricity than a system whereby water is supplied at all times.

Furthermore, since the on/off valve H is provided, there is no need to control the flow rate every time of opening and closing, and accordingly no need to provide the controller with a flow control mechanism.

The system for cleansing a urinal shown in FIG. 14 may also take a constitution as follows: an on/off valve H is provided in the first branch 132 at an upstream of the flow control valve 135; the on/off valve H is connected with the controller 137; a timer is provided in the controller 137; the flow control valve 135 is preset at a predetermined flow rate and the on/off valve H is opened only at night, whereby tap water constantly flows at a small flow rate from the flush water supply line 133 at the upstream of the water supply valve 134, via the first branch 132, the on/off valve H and the flow control valve 135, into the ozone-water generator 131; when the on/off valve 139 is opened, the ozone-water produced flows through the on/off valve 139 and the second branch 136 into the trap A132; when the water in the ozone-water generator 131 reaches a predetermined low level, the on/off valve 139 is closed and at the same time, or with a delay, the on/off valve H is closed.

When the above method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A131 at predetermined time intervals, or every time of use, by the operation of the automatic flushing system B131, or by manual operation, apart from the operation of the present system for cleansing a urinal, whereby the surface of the urinal A131 is flushed and the standing water in the trap A132 is renewed. Furthermore, since the on/off valve H is provided, there is no need to control the flow rate every time of opening and closing, and accordingly no need to provide the controller with a flow control mechanism.

The system for cleansing a urinal shown in FIG. 14 may also take a constitution as follows: an on/off valve H is provided in the first branch 132 at an upstream of the flow control valve 135; the on/off valve H is connected with the controller 137; the flow control valve 135 is preset at a predetermined flow rate; a timer is provided in the controller 137; the controller 137 is connected with the automatic flushing system B131 so that an operation signal of the system B131 is inputted to the controller 137; the timer of the controller 137 starts clocking on receiving the operation signal of the automatic flushing system B131; in case that the urinal is not used for a predetermined period of time after the last use thereof, i.e., that no operation signal of the automatic flushing system B131 is outputted for the predetermined period of time after the system B131 outputs the operation signal on the last use of the urinal A1 31, the controller 137 opens the on/off valve H as instructed by the timer; whereby tap water constantly flows at a small flow rate from the flush water supply line 133 at the upstream of the water supply valve 134, via the first branch 132, the on/off valve H and the flow control valve 135, into the ozone-water generator 131; when the on/off valve 139 is opened, the ozone-water produced flows through the on/off valve 139 and the second branch 136 into the trap A132; when the water in the ozone-water generator 131 reaches a predetermined low level, the on/off valve 139 is closed and at the same time, or with a delay, the on/off valve H is closed.

By this method, such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increase in the standing water, since tap water is supplied to the urinal A131 every time of use, by the operation of the automatic flushing system B131, or by manual operation, apart from the operation of the present system for cleansing a urinal, whereby the surface of the urinal A131 is flushed and the standing water in the trap A132 is renewed. Furthermore, since the on/off valve H is provided, there is no need to control the flow rate every time of opening and closing, and accordingly no need to provide the controller with a flow control mechanism.

Figure 15:
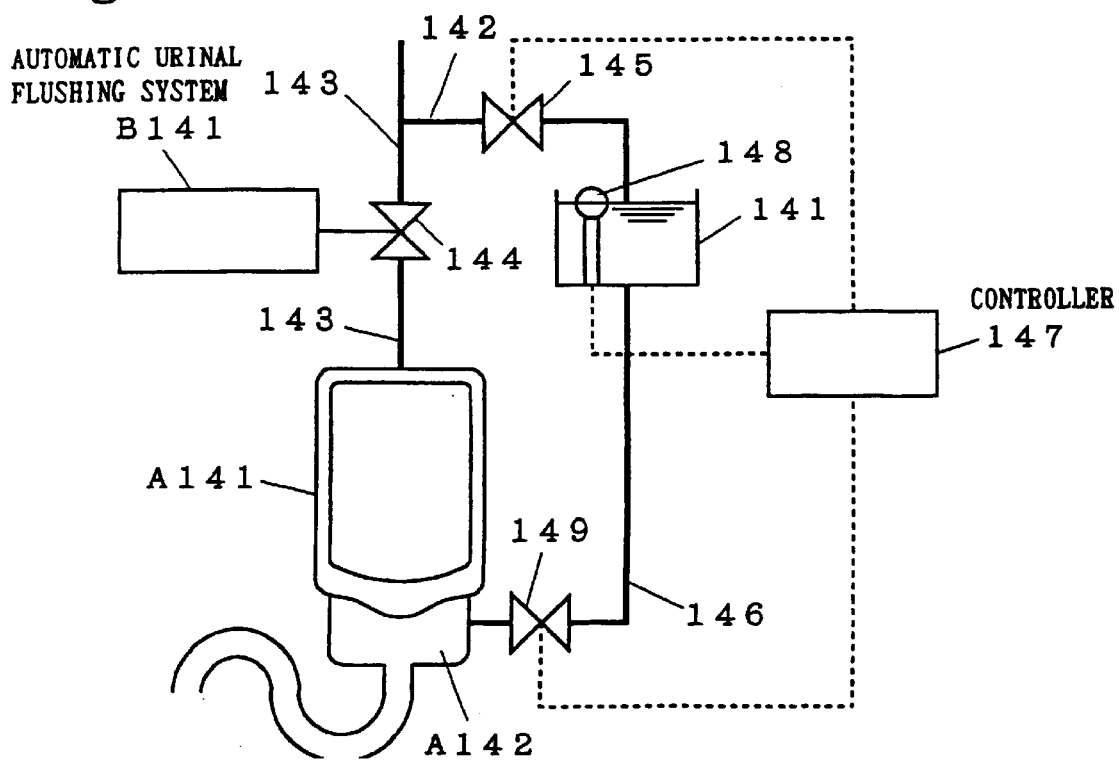
FIG. 15 shows a machinery structure of a system for cleansing a urinal comprising an ozone-water generator provided parallel to an existing flush water supply line, and having a constitution that an on/off valve for passing and stopping tap water flowing into the ozone-water generator and an on/off valve for passing and stopping the ozone-water flowing from the ozone-water generator are opened and closed as instructed by the controller, and that the ozone-water is supplied to the trap of the urinal.

FIG. 15 shows another embodiment of the system for cleansing a urinal according to the present invention. The present system comprises an ozone-water generator 141 having a float sensor 148; the unit 141 being connected by a first branch 142 with a flush water supply line 143 at an upstream of a water supply valve 144 consisting of a flush valve or the like. An on/off valve 145 is provided in the first branch 142. The ozone-water generator 141 is connected by a second branch 146 with the trap A142 of the urinal. The on/off valve 149 is provided in the second branch 146. The ozone-water generator 141, the on/off valves 145 and 149 are connected with a controller 147.

In the present system for cleansing a urinal, tap water flows from the flush water supply line 143 at the upstream of the water supply valve 144, via the first branch 142 and the on/off valve 145, into the ozone-water generator 141. The water level in the ozone-water generator 141 is detected by the float sensor 148. When the water in the ozone-water generator 141 reaches a predetermined level, the controller 147, on receiving a detection signal from the float sensor 148, closes the on/off valve 145. The controller 147 provided with a timer instructs the ozone-water generator 141 to start producing ozone-water only in case that the water level in the ozone-water generator 141 is higher than predetermined during a predetermined period of time. After producing the ozone-water, the controller 147 immediately opens the on/off valve 149, whereby the ozone-water produced flows through the on/off valve 149 and the second branch 146 into the trap A142.

The time when the water in the ozone-water generator reaches the predetermined level may be detected, as described above, either by measuring the water level directly by the float sensor 148 or by measuring the elapsing time from a time the on/off valve 145 in the first branch 142 or the on/off valve 149 in the second branch 146 is opened.

Apart from the operation of the present system for cleansing a urinal, tap water is supplied to the urinal A141 by the automatic flushing system B141, or by manual operation, every time of use, whereby the surface of the urinal A141 is flushed and the standing water in the trap A142 is renewed.

Also in the present system for cleansing a urinal, the ozone-water that is used for cleansing a urinal is produced by an electrical process such as silent discharge or electrolysis of water, therefore it requires less maintenance work and is safer to users than the conventional flushing system using chemicals mixed with flush water.

In the above system, the ozone-water is produced properly and supplied to the trap A142 as instructed by the timer.

Consequently, the increase and adhesion of urease due to the action of living bacteria can be effectively suppressed and the increase in pH due to the solution of ammonia is suppressed, so that the deposition of uric stone is prevented and one of the causes of the stench is also prevented.

In the above system for cleansing a urinal, it is possible to determine the period for producing ozone-water at predetermined time intervals as instructed by the timer. By this method, the ozone-water is supplied to the trap A142 at predetermined time intervals, so that resource and energy can be saved since it consumes less water and electricity than a system whereby water is supplied at all times.

In the above system for cleansing a urinal, it is possible to determine the period for producing ozone-water only at night as instructed by the timer, whereby the ozone-water is supplied to the trap A142 only at night. When this method is applied to a urinal that is used only in the day-time and rarely used at night, such as in the office building, in the department store, at the station, at the exhibition site, in the tourist facilities, or in the vehicle running only in the day-time, such a situation can be prevented that bacteria increase in the standing water of the urinal and urease increases and sticks to the surface of the urinal at night when the urinal is not used, so that the deposition of uric stone can be prevented and one of the causes of the stench can be prevented. In the day-time, neither bacteria nor urease increases in the standing water, since tap water is supplied to the urinal A141 at predetermined time intervals, or every time of use, by the operation of the automatic flushing system B141, or by manual operation, apart from the operation of the present system for cleansing a urinal, whereby the surface of the urinal A141 is flushed and the standing water in the trap A142 is renewed.

The above system for cleansing a urinal may also take a constitution as follows: the controller 147 is further connected with the automatic flushing system B141 so that an operation signal of the automatic flushing system B141 is inputted to the controller 147; the timer of the controller 147 starts clocking on receiving the operation signal of the automatic flushing system B141; in case that the urinal is not used for a predetermined period of time after the last use thereof, i.e., that no operation signal of the automatic flushing system B141 is outputted for the predetermined period of time after the system B141 outputs the operation signal on the last use of the urinal A141, the controller 147 determines the period for producing ozone-water as instructed by the timer. By this method, the ozone-water is supplied to the trap A142 only in case that the urinal is not used for a predetermined period of time after the last use thereof, whereby such a situation can be prevented that bacteria increase in the standing water of the urinal and urease increases and adheres to the surface of the urinal when the urinal is not used, so that the deposition of uric stone can be prevented and one of the causes of the stench can be prevented. When the urinal is in use, neither bacteria nor urease increases in the standing water, since tap water is supplied to the urinal A141 every time of use by the operation of the automatic flushing system B141, or by manual operation, apart from the operation of the present system for cleansing a urinal, whereby the surface of the urinal A141 is flushed and the standing water in the trap A142 is renewed.

(Embodiment 1)

Figure 16:
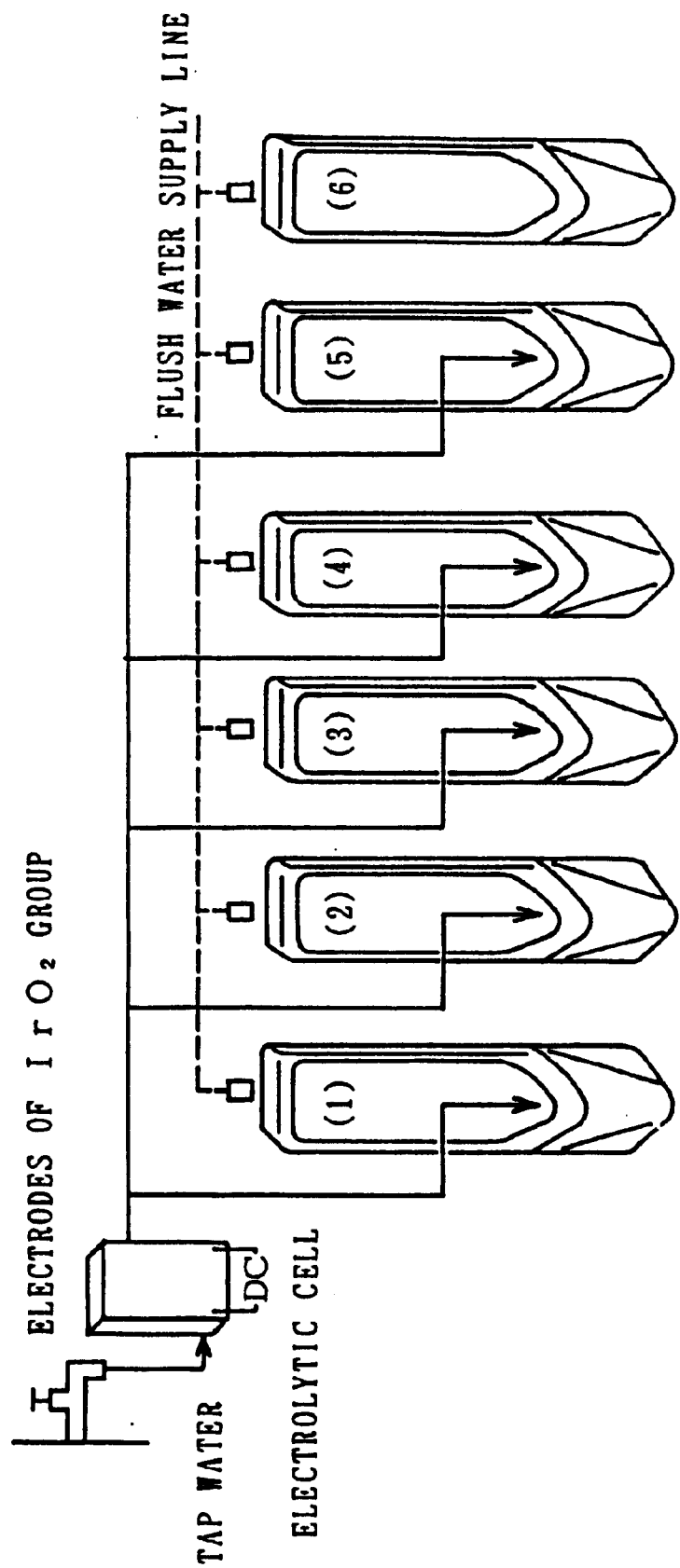
FIG. 16 shows a constitution of an equipment including urinals with which the test was carried out to prove the effect of the present invention using a system for cleansing a urinal comprising a continuous electrolytic cell.

A test was carried out to verify the effect of the present invention, using an equipment as shown in FIG. 16, wherein tap water was led to a diaphragm-less continuous electrolytic cell having plate electrodes, the tap water was electrolyzed with the chlorine-forming electrodes consisting of titanium plates coated with a catalyst of iridium oxide-platinum group, the water containing free chlorine produced by the electrolysis was supplied to urinals via pipes disposed apart from the flush water supply line, and then the number of bacteria in the standing water in the trap of the urinal, the pH of the standing water in the trap of the urinal, the stain on the surface of the trap of the urinal, etc., were investigated.

In this test, waters containing free chlorine with different concentrations were supplied to urinals (1) to (5) of FIG. 16 at different time intervals, but no water containing free chlorine was supplied to a urinal (6). All the urinals (1) to (6) were flushed also by a normal flush operation every time of use. The testing condition is shown in Table 1. The urinals are rarely used at night, since they are set in the office building.

After continuing the test of Table 1 for one month, the traps of the urinals (1) to (6) were taken out and their surfaces were investigated. There, the stain and the deposition of uric stone were found in the urinal (6), whereas neither the stain nor the deposition of uric stone was found in the urinals (1) to (5).

Figure 28A:
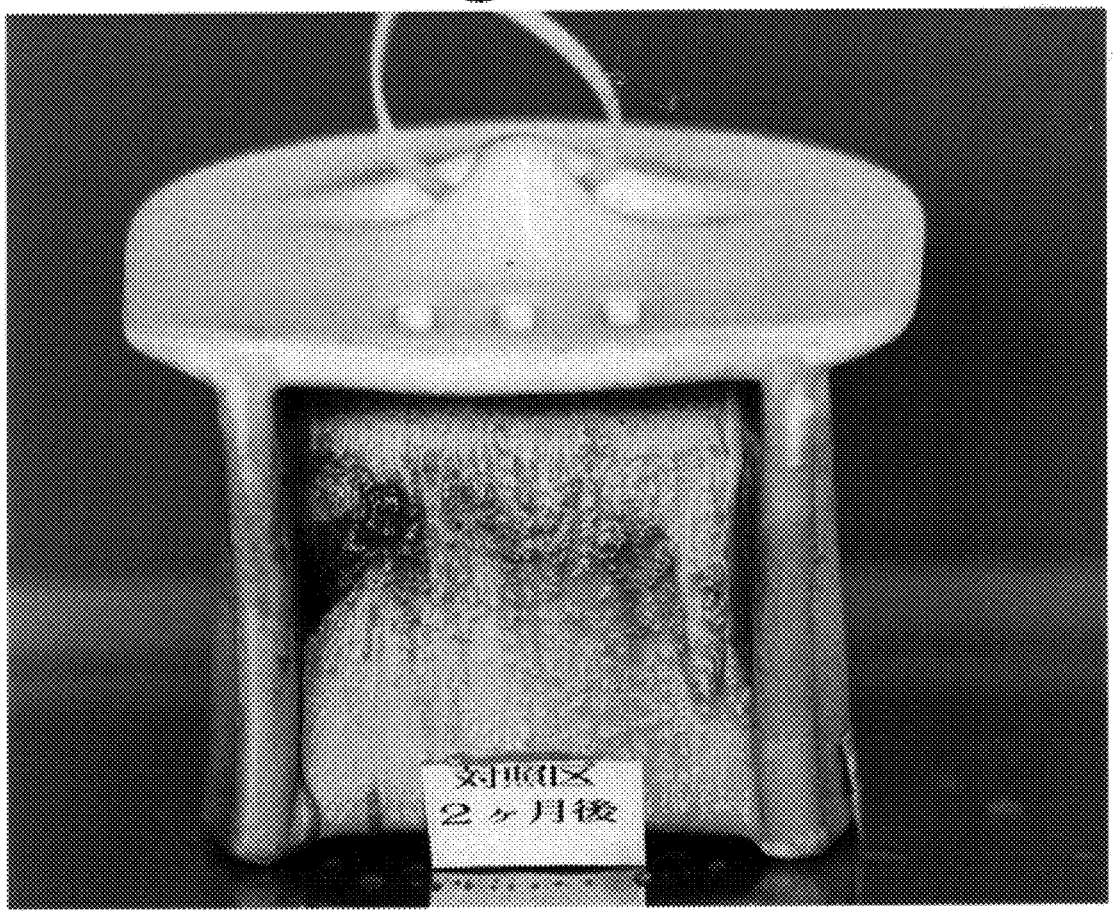
FIG. 28 shows appearances of the stain on the traps observed in the test of Table 1 after 2 months; wherein (a) is a front view of the trap flushed only by a normal method, (b) is a side view of the trap flushed only by a normal method, (c) is a front view of the trap cleansed by a water containing free chlorine, and (d) is a side view of the trap cleansed by a water containing free chlorine.
Figure 28B:
Figure 28C:
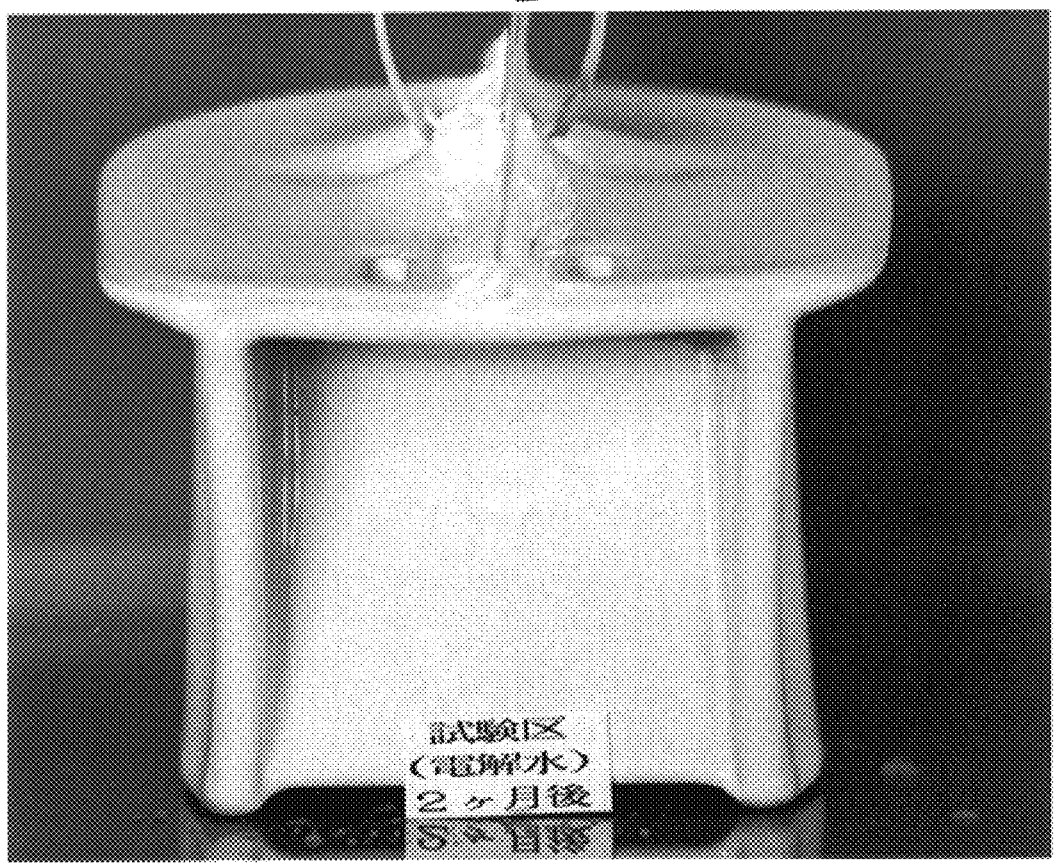
Figure 28D:
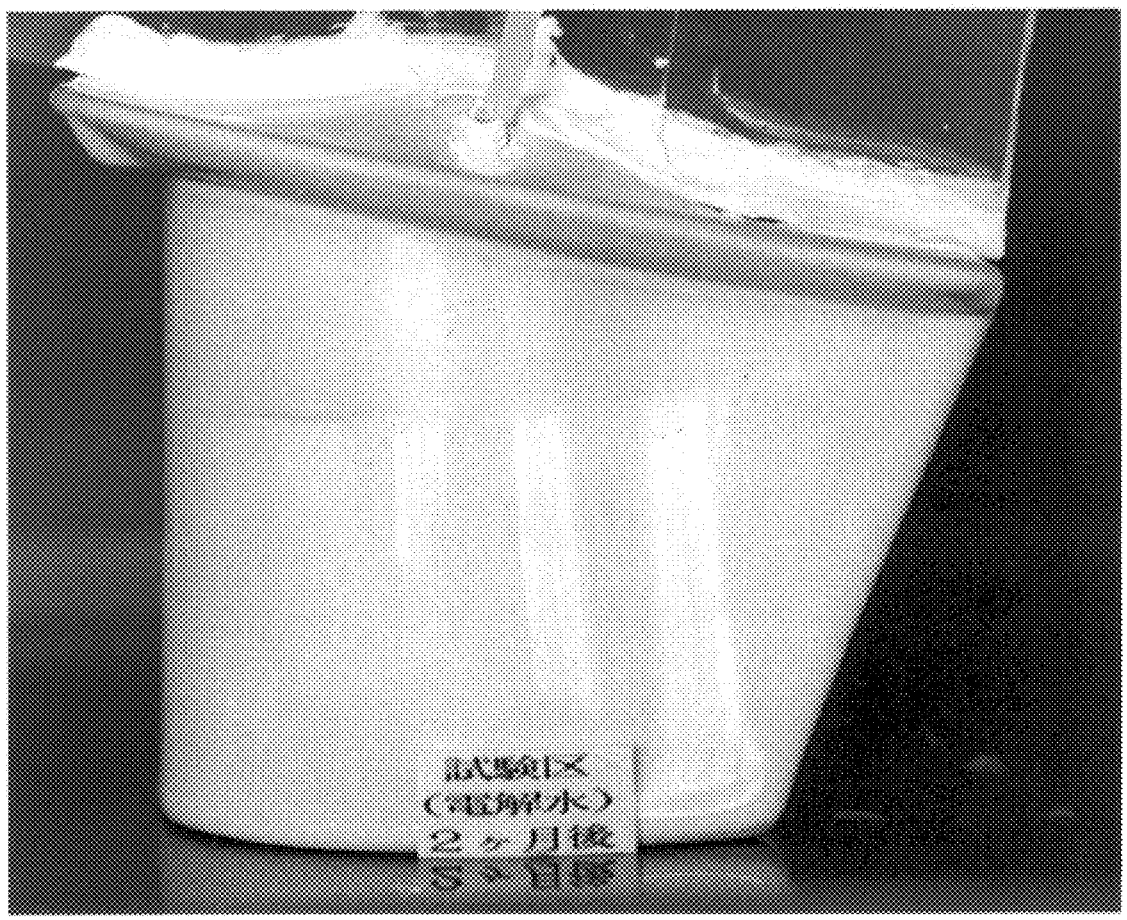
Figure 29A:
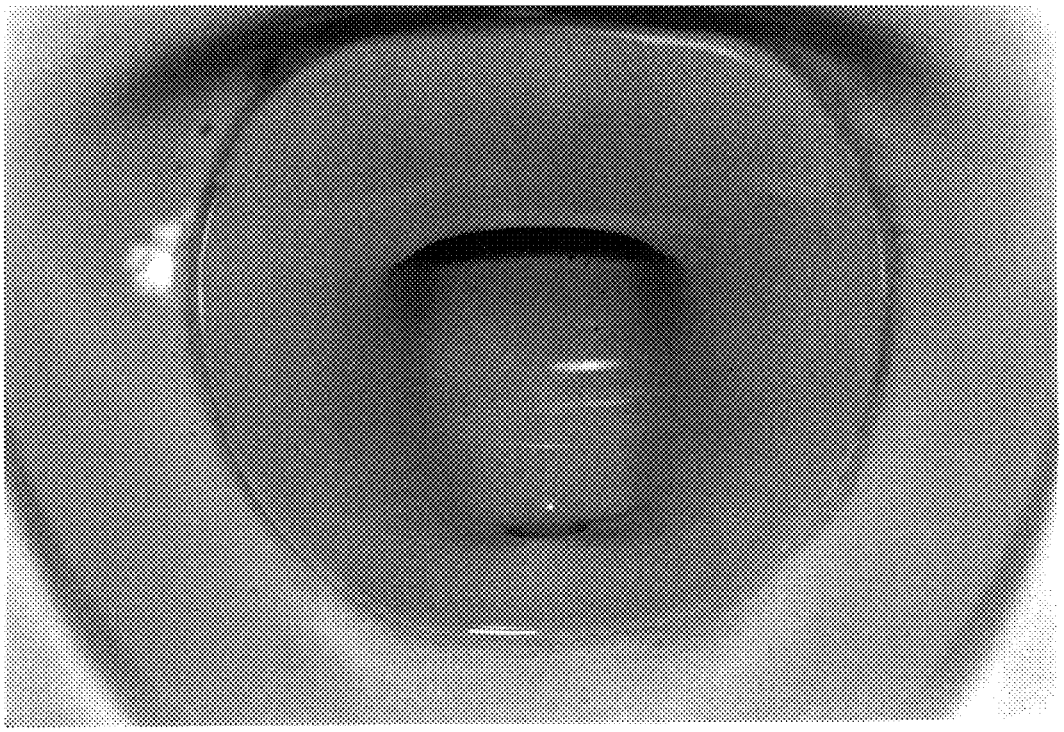
FIG. 29 shows the appearances of the stain on the toilet bowl caused by normal use; wherein (a) is the appearance after two weeks, and (b) is the appearance after four weeks.
Figure 29B:
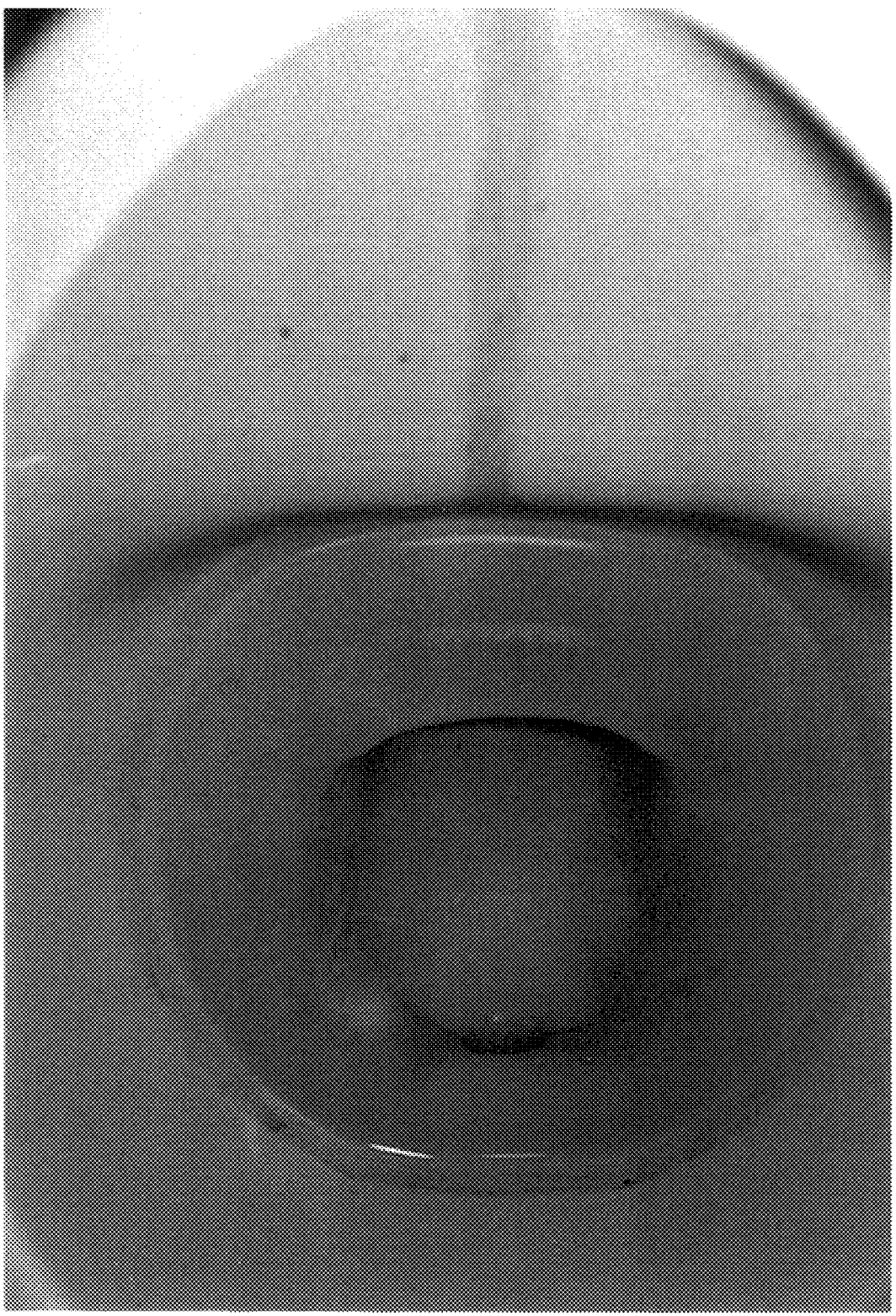

The test was continued further. FIG. 28 shows the stain on the traps after two months from the beginning. FIGS. 28(a) and (b) show the outlook of the trap of the urinal (6), and FIGS. 28(c) and (d) show the outlook of the trap of the urinal (1). The difference in the state of the stain and the deposition of uric stone can be obviously observed between these Figures.

Further, in the urinals (2), (4) and (5), the standing water in the trap of the urinal was sterilized, the pH of the standing water in the trap of the urinal was lowered and no yellowish stain was detected. Therefore, it seems that the increase of

TABLE 1

| URINAL No. | (1) | (2) | (3) | (4) | (5) | (6) |
|---|---|---|---|---|---|---|
| Free Chlorine Concentration (mg/l) | 3 | 3 | 1 | 0.5 | 0.1 | |
| Frequency of Free Chlorine Water Supply | every 4 hours | only 10:00 pm and 3:00 am | every 4 hours | only 10:00 pm and 3:00 am | only 10:00 pm and 3:00 am | |
| Amount of Free Chlorine Water per One Supply (1) | 5 | 5 | 5 | 5 | 5 | |
| Electric Power Consumed | 7 W (4.5 V, 1.5 A) | 7 W (4.5 V, 1.5 A) | 5 W (4.5 V, 1 A) | 3 W (4 V, 0.7 A) | 2 W (3.5 V, 0.6 A) | |
| Conventional Flush | on every use | on every use | on every use | on every use | on every use | on every use |

Figure 17:
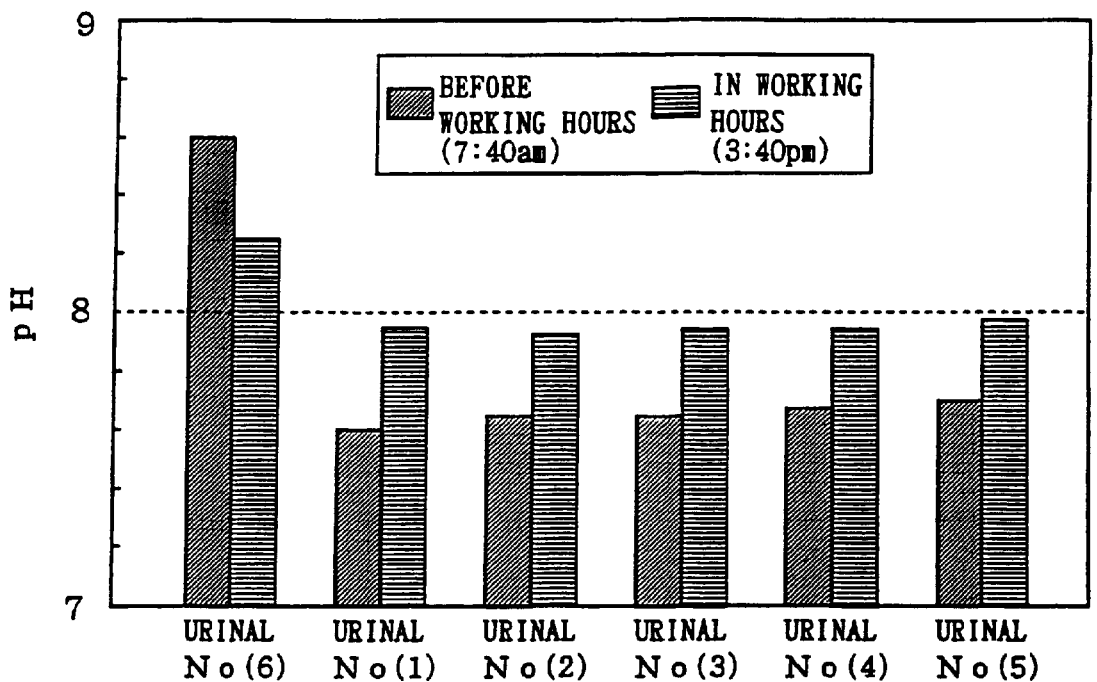
FIG. 17 is a diagram showing the pH of the standing water of the urinal measured after 0.5 month from the beginning of a test to prove the effect with respect to various free chlorine concentrations and supplying frequencies.

The numbers of bacteria in the standing water in the traps of the urinals after 0.5 month from the beginning are shown in Table 2, and the pHs of the standing water in the traps of the urinals are shown in FIG. 17.

TABLE 2

| URINAL No. | 7:40 am Before Used | 3:40 pm Before Free Chlorine Water Supply | 4:00 pm After Free Chlorine Water Supply |
|---|---|---|---|
| (1) | 0 | $3.4 \times 10^3$ | 0 |
| (2) | 0 | $8 \times 10^2$ | 0 |
| (3) | 0 | $5 \times 10^2$ | 0 |
| (4) | 0 | $4 \times 10^3$ | 0 |
| (5) | $2 \times 10^2$ | $3.5 \times 10^3$ | 0 |
| (6) | $9 \times 10^4$ | $1 \times 10^4$ | — |

The data of the urinal (6) in Table 2 and FIG. 17 show that the number of bacteria in the standing water in the trap of the urinal increases, the urease increases and the pH of the standing water in the trap of the urinal increases more at night when the urinal is not used, no normal flush operation is carried out and the standing water in the trap of the urinal remains unrenewed, than in the day-time when the urinal is in use, the normal flush operation is carried out and the standing water in the trap is renewed. Therefore, it seems that the deposition of uric stone to the urinal progresses at night.

The data of the urinals from (1) to (5) in Table 2 and FIG. 17 show that the standing water in the trap of the urinal is sterilized and the pH of the standing water in the trap of the urinal is lowered by supplying to the urinals a water containing free chlorine with the concentration of 0.1 to 3 mg/l (i.e. weight of chlorine atoms contained per one liter) that is obtained by electrolyzing tap water.

bacteria in the standing water in the trap of the urinal, i.e. the increase of urease, can be prevented, and the increase in pH of the standing water in the trap of the urinal can be suppressed and, consequently, the deposition of uric stone to the urinal can be suppressed by supplying a water containing free chlorine to the urinal at night when the urinal is not used, no normal flush operation is not carried out and the standing water in the trap of the urinal remains unrenewed.

The data of urinals (1) and (2) in Table 2 and FIG. 17 show that, in the day-time, since the standing water in the trap of the urinal is renewed by the normal flush operation after use and the increase of bacteria in the standing water in the trap of the urinal is suppressed thereby, the number of bacteria in the standing water in the trap of the urinal and the pH of the standing water in the trap of the urinal differ little whether the water containing free chlorine was supplied to the urinal or not. Accordingly, it seems less necessary to supply a water containing free chlorine to a urinal in the day-time when the urinal is used.

The data of the urinals (2), (4) and (5) in Table 2 and FIG. 17 show that, in respect of the effect of killing bacteria in the standing water in the trap of the toilet or of the effect of suppressing the increase in pH of the standing water of the urinal, there is little difference between the water containing free chlorine with the concentration of 3 mg/l and the water containing free chlorine with the concentration of 0.5 mg/l. Further, in respect of the effect of sterilizing the standing water in the trap of the toilet or the effect of suppressing the increase in the pH of the standing water, there is not a large difference between the water containing free chlorine with the concentration of 3 mg/l and the water containing free chlorine with the concentration of 0.1 mg/l.

Accordingly, it seems that the deposition of uric stone to the urinal can be suppressed by supplying to the urinal the water containing free chlorine with the concentration of 0.1 mg/l.

(Embodiment 2)

A test was carried out to verify the effect of the present invention, using the equipment as shown in FIG. 16, wherein tap water was led to a diaphragm-less continuous electrolytic cell having plate electrodes, the tap water was electrolyzed with the chlorine-forming electrodes consisting of titanium plates coated with a catalyst of iridium oxide-platinum group, the water containing free chlorine produced by the electrolysis was supplied to urinals via pipes disposed apart from the flush water supply line, and then the number of bacteria in the standing water in the trap of the urinal, the pH of the standing water in the trap of the urinal, the stain on the surface of the trap of the urinal, etc., were investigated.

In the above-described embodiment 1, the water containing free chlorine produced by the electrolysis was supplied to the urinals immediately. In the present embodiment, on the other hand, the standing water was compulsorily renewed by the automatic flushing system first, whereafter the water containing free chlorine produced by the electrolysis was supplied to the urinals.

The test was carried out with the urinals (1) to (4) in FIG. 16. Waters containing free chlorine with different concentrations were supplied to the urinals (1) to (3) at different time intervals, but no water containing free chlorine was supplied to the urinal (4). All the urinals (1) to (4) were flushed also by a normal flush operation every time of use. The testing condition is shown in Table 3. The urinals are rarely used at night since they are set in the office building.

water, with the concentration of 0.02 to 0.5 mg/l (weight of chlorine atoms contained per liter).

After continuing the test of Table 3 for one month, the traps of the urinals (1) to (4) were taken out and their surfaces were investigated. There, the stain and the deposition of uric stone were found in the urinal (4), whereas neither the stain nor the deposition of uric stone was found in the urinals (1) to (3).

In the present test, the effect was obtained by supplying to the urinal the water containing free chlorine with the concentration of 0.02 mg/l. This is probably because the number of bacteria in the standing water was decreased beforehand by renewing the standing water.

(Embodiment 3)

Two tests were carried out as follows to verify the effect of the present invention on the toilet. In the present embodiment, the term "toilet" does not include "urinal".

Test 1: The toilet was used ordinarily and the state of the stain was investigated. No stain was found on the toilet bowl surface at the beginning. After two weeks, however, a pink, ring-shaped stain was formed at draught level, as shown in FIGS. 19(*a*) and 29(*a*), and further, spoke-like stripes of stain were formed in water flow directions on the rim portion of the bowl surface after four weeks, as shown in FIGS. 19(*b*) and 29(*b*).

Test 2: The toilet was used ordinarily and the water containing free chlorine produced by the electrolysis was supplied thereto twice a day, at 8 a.m. and 11 p.m. The water containing free chlorine was produced by the electrolysis and supplied to the toilet as follows: tap water was led to a diaphragm-less continuous electrolytic cell having plate electrodes, the tap water was electrolyzed with the chlorine-forming electrodes consisting of titanium plates coated with

TABLE 3

| URINAL No. | (1) | (2) | (3) | (4) |
|---|---|---|---|---|
| Free Chlorine Concentration (mg/l) | 0.5 | 0.1 | 0.02 | |
| Frequency of Free Chlorine Water Supply | Every 1 hour Between 10:00 pm–3:00 am | Every 1 hour Between 10:00 pm–3:00 am | Every 1 hour Between 10:00 pm–3:00 am | |
| Amount of Free Chlorine Water per One Supply (1) | 5 | 5 | 5 | |
| Electric Power Consumed | 3 W (4 V, 0.7 A) | 2 W (3.5 V, 0.6 A) | 1 W (2.5 V, 0.4 A) | |
| Conventional Flush | on every use | on every use | on every use | on every use |

Figure 18:
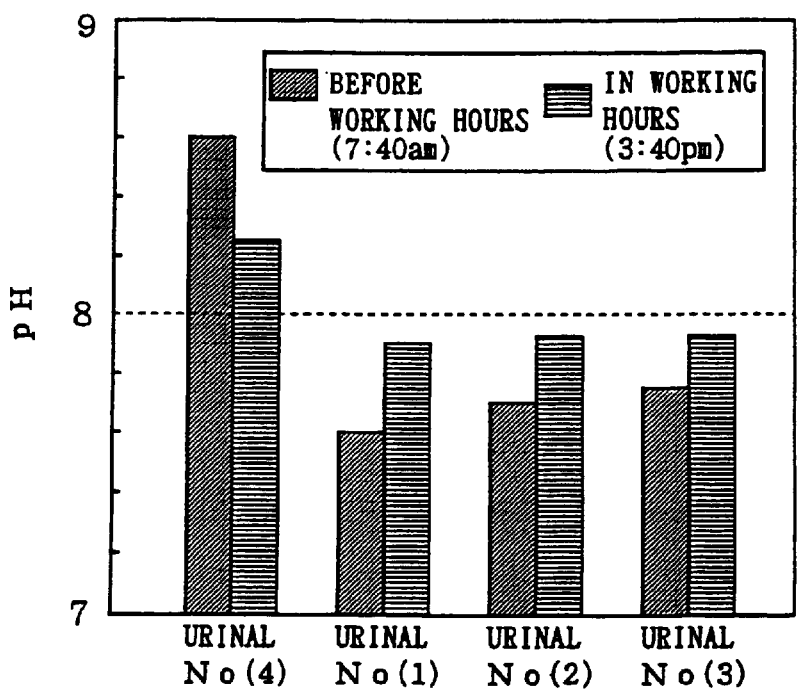
FIG. 18 is a diagram showing the pH of the standing water of the urinal measured after 0.5 month from the beginning of a test wherein the water containing free chlorine is supplied only at night.

The number of bacteria in the standing water in the traps of the urinals after 0.5 month from the beginning is shown in Table 4, and the pH of the standing water in the traps of the urinals is shown in FIG. 18. Here, the number of bacteria in the standing water in the traps of the urinals was measured at 7:40 a.m.

TABLE 4

| URINAL No. | (1) | (2) | (3) | (4) |
|---|---|---|---|---|
| Number of Bacteria | 0 | 0 | 0 | $1 \times 10^5$ |

Figure 30A:
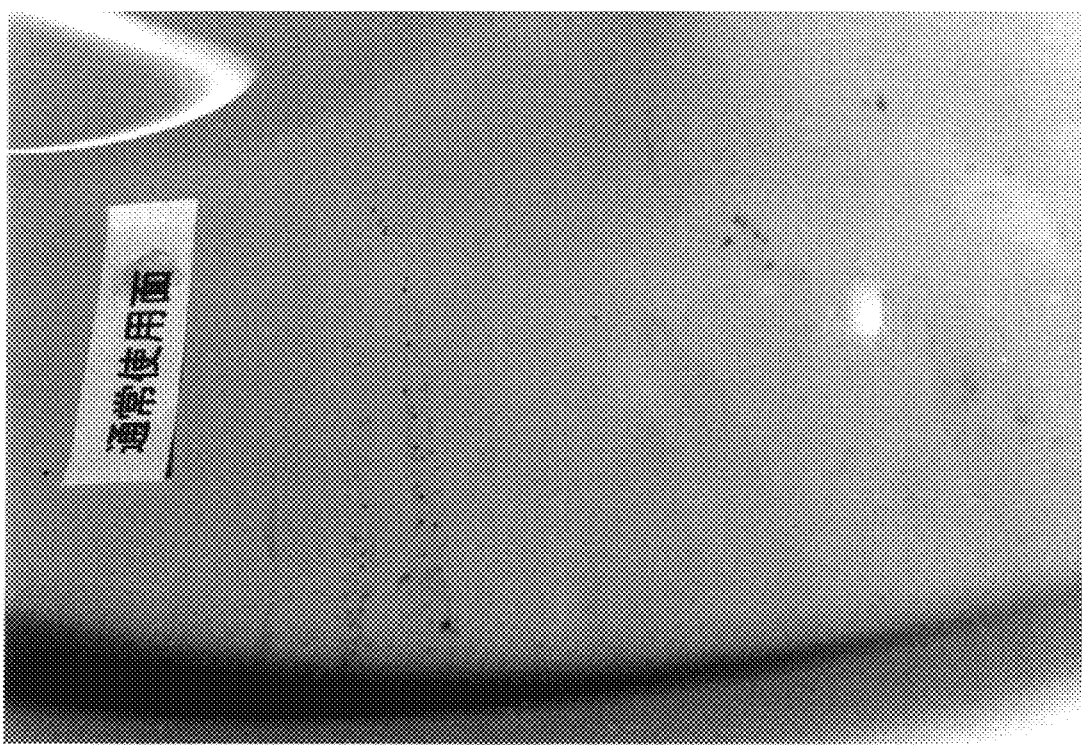
FIG. 30 shows the appearances of the stain on the toilet bowl observed in the test of FIG. 20 after four weeks; wherein (a) is the appearance of one side of the bowl surface flushed only by the normal method, and (b) is the appearance of the other side of the bowl surface cleansed by the water containing free chlorine.
Figure 30B:
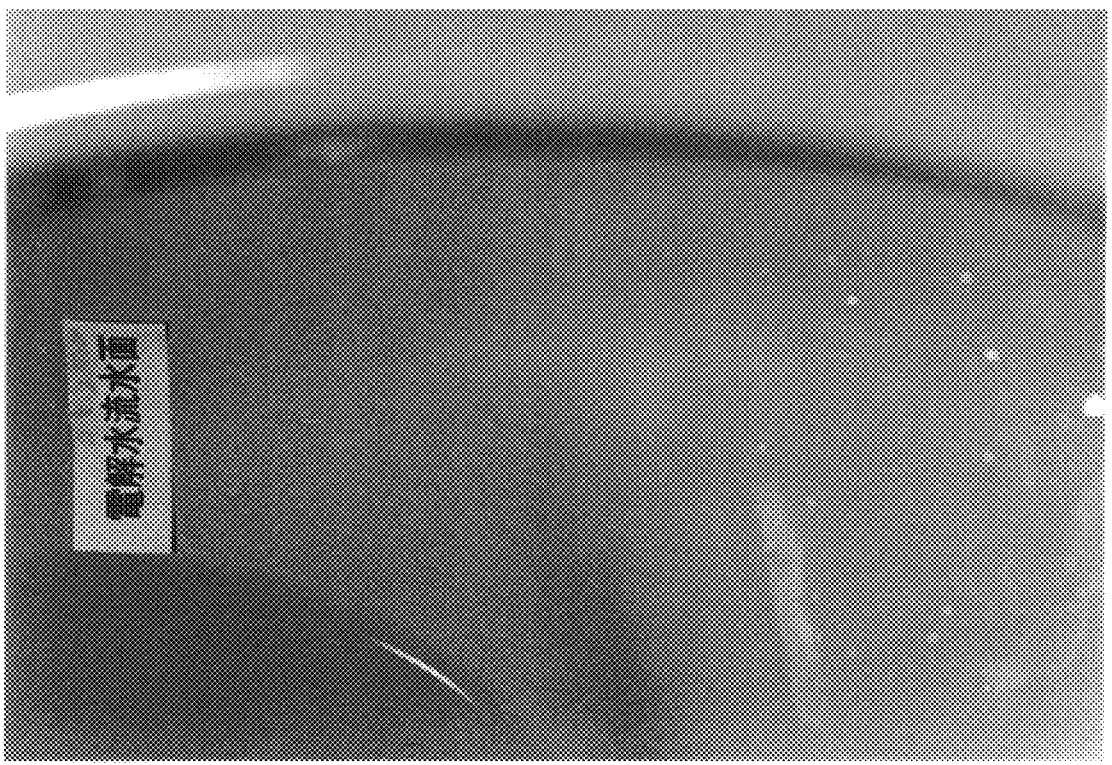

The data of the urinals (1) to (3) in Table 4 and FIG. 18 show that the standing water in the trap of the urinal is sterilized and the pH of the standing water in the trap of the urinal is lowered by supplying to the urinal the water containing free chlorine, produced by electrolyzing tap a catalyst of iridium oxide-platinum group, the water containing free chlorine produced was supplied near flush water supply ports provided beneath a rim of the toilet over a half of the bowl surface and (FIG. 20). No stain was found on the bowl at the beginning. After four weeks, however, spoke-like stripes of stain were formed in water flow directions on the other half surface of the rim of the bowl that was not supplied with the water containing free chlorine, as shown in FIG. 21. FIG. 30(*a*) is a magnified view of the stained portion. On the other hand, no stain was detected on the half surface that was supplied with the water containing free chlorine, as shown in FIG. 30(*b*). Here, the pink, ring-shaped stain found at draught level in the test 1 was not detected, either.

The tests 1 and 2 have clarified that also the stain of the toilet can be prevented by supplying the water containing free chlorine produced by the electrolysis.

The positions of spoke-like stripes of stain formed in the water flow directions on the rim portion of the bowl surface almost exactly correspond to the flush water supply ports separately provided beneath the rim, which suggests that the continuous supply of water helps bacteria to increase at the positions. Therefore, in supplying the water containing free chlorine produced by the electrolysis to the toilet, it is preferable to supply it from the same positions as the flush water supply ports are provided. For this reason, it is preferable to supply it via the flush water supply line.

(Embodiment 4)

Figure 22:
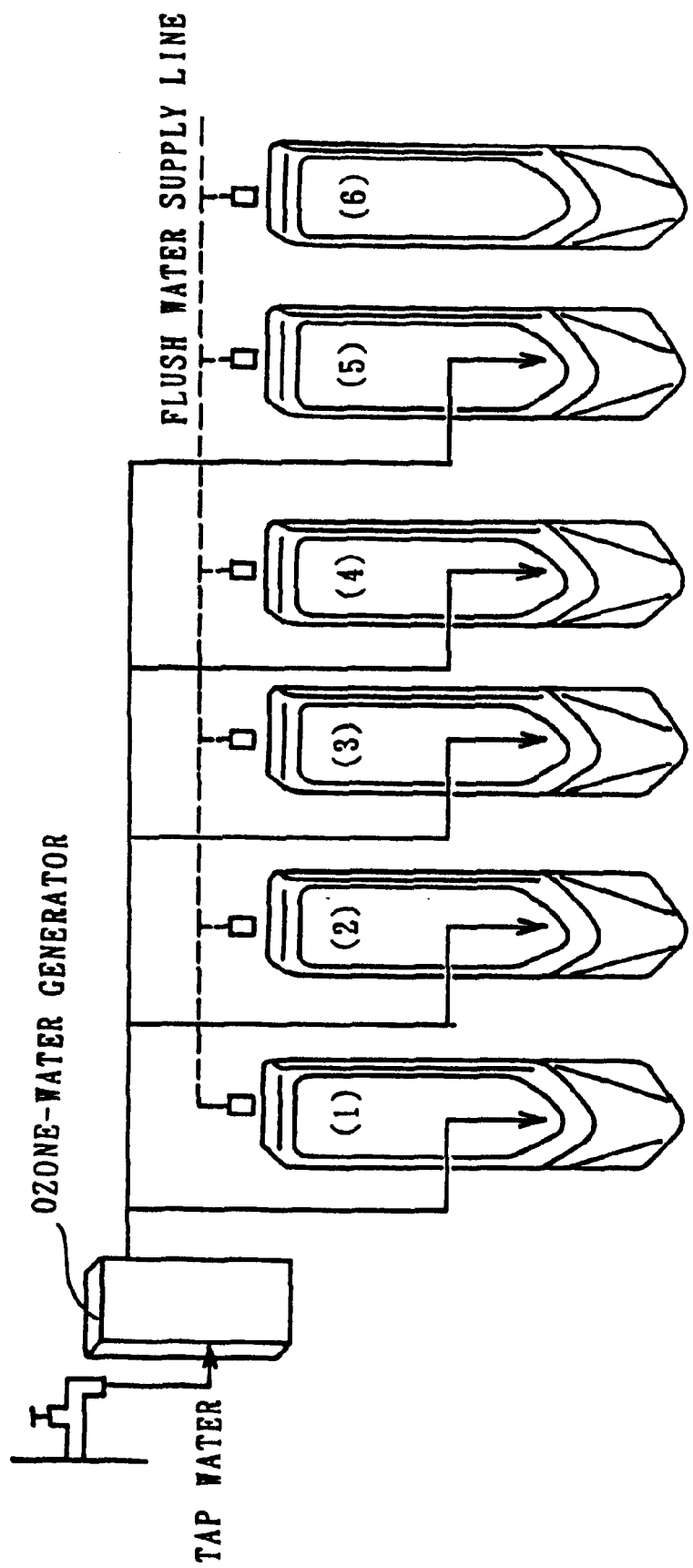
FIG. 22 shows a constitution of an equipment including urinals with which a test was carried out to prove the effect of the present invention using a system for cleansing a urinal comprising a device for preparing ozone-water.

A test for verifying the effect of the present invention was carried out, using the equipment shown in FIG. 22, wherein tap water was led to an ozone-water generator, an ozone-water was produced thereby, and the ozone-water produced was supplied to the urinal via a pipe apart from the flush water supply line, and then the number of bacteria in the standing water in the trap of the urinal and the stain on the surface of the trap of the urinal were investigated.

In this test, the ozone-waters with different concentrations were supplied to the urinals (1) to (5) of FIG. 22 at different time intervals, but no ozone-water was supplied to the urinal (6). All the urinals (1) to (6) were flushed also by a normal flush operation every time of use. The testing condition is shown in Table 5.

The data of the urinals from (1) to (5) in Table 6 and FIG. 22 show that the standing water in the trap of the urinal is sterilized by supplying to the urinal the ozone-water with the concentration of 0.01 to 0.1 mg/l (i.e. weight of chlorine atoms contained per liter).

After continuing the test of Table 5 for one month, the traps of the urinals (1) to (6) were taken out and their surfaces were investigated. There, the stain and the deposition of uric stone were found in the urinal (6), whereas neither the stain nor the deposition of uric stone was found on the urinals (1) to (5).

Besides, in the urinals (2), (4) and (5), the standing water in the trap of the urinal was sterilized and no yellowish stain was found. Therefore, it seems that the increase of bacteria in the standing water in the trap of the urinal, and the increase of urease, can be impeded and, consequently, the deposition of uric stone to the urinal can be suppressed by supplying the ozone-water to the urinal at night when the urinal is not used, no normal flush operation is carried out and the standing water remains unrenewed.

The data of urinals (1) and (2) in Table 6 and FIG. 22 show that, in the day-time, since the standing water is renewed by the normal flush operation subsequent to a use

TABLE 5

| URINAL No. | (1) | (2) | (3) | (4) | (5) | (6) |
|---|---|---|---|---|---|---|
| Ozone Concentration (mg/l) | 0.1 | 0.1 | 0.05 | 0.05 | 0.01 | |
| Frequency of Ozone-Water Supply | every 4 hours | only 10:00 pm and 3:00 am | every 4 hours | only 10:00 pm and 3:00 am | only 10:00 pm and 3:00 am | |
| Amount of Ozone-Water per One Supply (l) | 5 | 5 | 5 | 5 | 5 | |
| Conventional Flush | on every use | on every use | on every use | on every use | on every use | on every use |

The numbers of bacteria in the standing water in the traps of the urinals after 0.5 month from the beginning are shown in Table 6.

TABLE 6

| URINAL No. | 7:40 am Before Used | 3:40 pm Before Ozone-Water Supply | 4:00 pm After Ozone-Water Supply |
|---|---|---|---|
| (1) | A | B | A |
| (2) | A | B | A |
| (3) | A | B | A |
| (4) | A | B | A |
| (5) | B | B | A |
| (6) | D | C | — |

A—zero
B—less than $1 \times 10^3$
C—equal to or greater than $1 \times 10^3$, but less than $1 \times 10^5$
D—equal to or greater than $1 \times 10^5$ The data of the urinal (6) in Table 6 show that the number of bacteria in the standing water in the trap of the urinal increases and the urease increases more at night when the urinal is not used, no normal flush operation is carried out and the standing water in the trap of the urinal remains unrenewed, than in the day-time when the urinal is used, the normal flush operation is carried out and the standing water in the trap of the urinal is renewed. Therefore, it seems that the deposition of uric stone to the urinal progresses at night.

and the increase of bacteria in the standing water are suppressed thereby, the number of bacteria in the standing water in the trap of the urinal differs little whether the water containing free chlorine was supplied to the urinal or not. Accordingly, it seems less necessary to supply ozone-water to a urinal in the day-time when the urinal is used.

The data of the urinals (2), (4) and (5) in Table 6 and FIG. 22 show that there is little difference in respect of the effect of sterilizing the standing water in the trap of the toilet between the ozone-water with the concentration of 0.1 mg/l and the ozone-water with the concentration of 0.05 mg/l. Further, there is not a large difference in respect of the effect of sterilizing the standing water in the trap of the toilet between the ozone-water with the concentration of 0.1 mg/l and the ozone-water with the concentration of 0.01 mg/l. Accordingly, it seems that the deposition of uric stone to the urinal can be suppressed by supplying to the urinal the ozone-water with the concentration of 0.01 mg/l.

(Embodiment 5)

Ten pieces of solid samples, each composed of a porous alumina ball having 5 mm diameter with a titania fixed thereon and impregnated by a silver nitrate solution, were placed on the trap of a urinal. The stain on the trap of the urinal was investigated after leaving the samples for one month. As a result, the color of the urinal without the solid sample placed thereon turned into bright yellow, whereas little stain was formed on the urinal with the solid samples placed thereon. Thus, it has been confirmed that the above solid sample has a significant effect to prevent the stain on the trap of the urinal.

This effect is probably because silver ions dissolve from the solid sample into the standing water, the silver ions act on and kill bacteria in the standing water or on the trap of the urinal, and thus the increase of urease is suppressed.

(Embodiment 6)

To investigate the sterilizing action of silver ions in the standing water, test liquids were prepared by dissolving silver nitrate in the ion exchange water to obtain a solution with silver concentration of 1 mg/l, then diluting the solution with a sterilized ultra pure water to obtain a test liquid having a predetermined silver ion concentration. The test liquids having silver ion concentrations of 1 mg/l and 10 mg/l, however, were prepared by dissolving silver nitrate in the sterilized ultra pure water directly. *Escherichia coli* was put in each of the test liquids by $2\times10^5$ CFU/ml. After leaving the liquids untouched for a predetermined period of time, potassium iodide was added to precipitate silver ions in the form of silver iodide, which was removed from the test liquid, and then the survival rate of bacteria was investigated.

Figure 23:
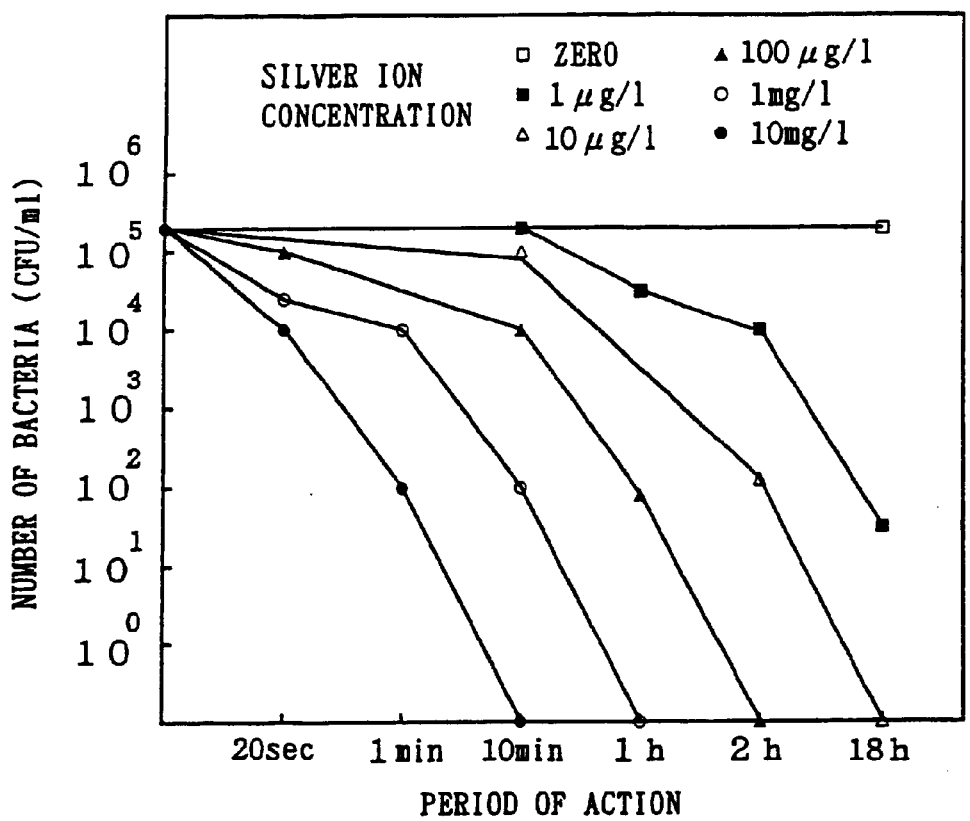
FIG. 23 shows the number of *Escherichia coli* remaining after the water containing silver ions is applied thereon.

The result is shown in FIG. 23. When the silver ion concentration is 1 mg/l or above, only less than 10% of bacteria can survive even by the short-period action of about 20 seconds, whereas, when the silver ion concentration is 1 $\mu$g/l or so, the survival rate does not become lower than about 10% without the long-period action of about one hour.

It seems, however, that silver ions do not tend to lose their effect even when the action time is set longer. Therefore, when silver ions are used to sterilize a toilet, it is preferable to put the silver ions in the standing water or the like and let them act slowly.

(Embodiment 7)

Test liquid for confirming the sterilizing action of silver ions in the standing water was prepared by dissolving silver nitrate in the ion exchange water to obtain a solution containing 100 mg/l of silver, then diluting the solution with water of the flush tank to obtain the test liquid containing silver ions with a predetermined concentration. *Escherichia coli* was put in the test liquid by $2\times10^5$ CFU/ml. After leaving the liquid untouched for a predetermined period of time, potassium iodide was added to let silver ions precipitated and removed from the liquid in the form of silver iodide, then the survival rate of bacteria was investigated.

Figure 24:
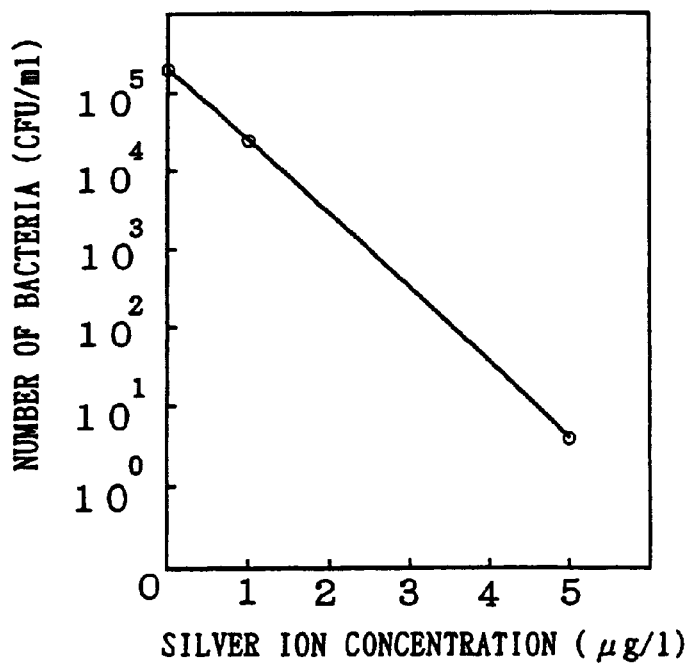
FIG. 24 shows the number of *Escherichia coli* remaining after the water containing silver ions is applied thereon for two hours.

The result is shown in FIG. 24. The action time was set at 2 hours. It turned out that only less than 10% of bacteria can survive when the silver ion concentration is 1 $\mu$g/l or above. Therefore, it can be said that, if the action time is set long, the bacteria can be killed and the stain can be prevented sufficiently even by using the water that is used actually.

(Embodiment 8)

(1) Tap water or water of a flush tank was supplied at 10 p.m. and at 3 a.m. during the night to a urinal placed in the office building that was ordinarily used in the day time and rarely used at night.

The result is as follows: in case of supplying the tap water, a portion of the trap of the urinal impregnated by the standing water was found to be colored bright yellow due to the uric stone at 8 a.m. on the day after one month; while, in case of supplying the water of the flush tank, a thin, slime-like matter was found sticking to the trap of the urinal impregnated by the standing water and the trap was colored bright yellow.

Besides, the number of bacteria in the standing water is investigated every week. The result is shown in Table 7, wherein the highest value is $1\times10^4$ CFU/ml in case of supplying the tap water, while it is $3\times10^4$ CFU/ml in case of supplying the water of the flush tank.

(2) Nextly, another test was carried out, using the equipment shown in FIG. 16, wherein tap water or water of the flush tank was led to a diaphragm-less continuous electrolytic cell having plate electrodes, the tap water or the water of the flush tank was electrolyzed by the chlorine-forming electrodes consisting of titanium plates coated with a catalyst of iridium oxide-platinum group, and the water containing free chlorine produced by the electrolysis was supplied at 10 p.m. and at 3 a.m. during the night via pipes apart from the flush water supply line to the urinal placed in the office building that was ordinarily used in the day time and rarely used at night.

As a result, in any case of supplying the water containing free chlorine with the concentration of 1 mg/l produced by electrolysis of the tap water or of supplying the water containing free chlorine produced by electrolysis of the water of the flush tank, neither the deposition of uric stone nor the stain was found on the trap at the portion impregnated by the standing water after one month.

Besides, the number of bacteria in the standing water was investigated every week. The result is shown in Table 7, wherein the value is continuously zero CFU/ml in case of supplying the water containing free chlorine with the concentration of 1 mg/l produced by electrolysis of the tap water, while it is $2\times10$ CFU/ml at the highest in case of supplying the water containing free chlorine with the concentration of 0.5 mg/l produced by electrolysis of the water of the flush tank, and $2\times10^3$ CFU/ml at the highest in case of supplying the water containing free chlorine with the concentration of 0.1 mg/l produced by electrolysis of the tap water.

TABLE 7

|  | 1 Week | 2 Weeks | 3 Weeks | 4 Weeks |
| --- | --- | --- | --- | --- |
| Tap Water | $8\times10^2$ | $3\times10^3$ | $1\times10^4$ | $5\times10^3$ |
| Low Tank Water | $5\times10^3$ | $5\times10^3$ | $3\times10^4$ | $6\times10^3$ |
| Free Chlorine Water |  |  |  |  |
| 1 mg/l | 0 | 0 | 0 | 0 |
| 0.5 mg/l | 0 | $1\times10$ | $2\times10$ | $1\times10$ |
| 0.1 mg/l | $1\times10^2$ | $8\times10^2$ | $2\times10^3$ | $6\times10^2$ |

(3) According to the results of (1) and (2), the deposition of uric stone and the stain occur more probably when the number of bacteria in the standing water is over $1\times10^4$ CFU/ml. Therefore, it is probable that the deposition of uric stone and the stain can be prevented by keeping the number of bacteria in the standing water lower than $1\times10^4$ CFU/ml.

(Embodiment 9)

A test for investigating the sterilizing effect of free chlorine in the standing water was carried out, wherein the predetermined quantity of *Escherichia coli* were put in the water containing free chlorine. After 20 seconds, sodium thiosulfate was added to remove free chlorine, then the survival rate of bacteria was investigated.

Figure 25:
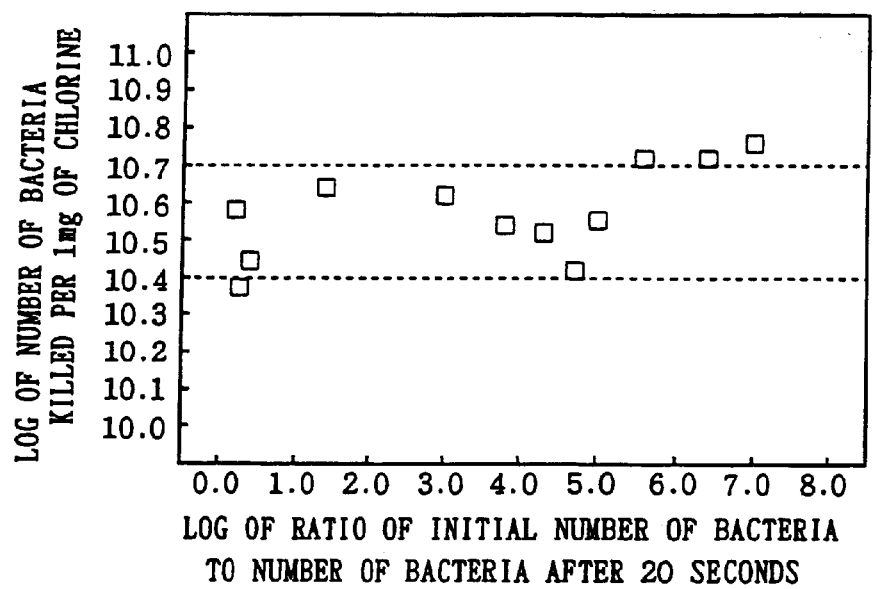
FIG. 25 shows a relationship between the number of bacteria that 1 mg of free chlorine can kill and the sterilizing power of the water containing free chlorine.

The result is shown in FIG. 25, wherein the horizontal axis denotes sterilizing power, i.e. a reciprocal of the survival rate, and the vertical axis denotes the number of bacteria that can be killed by 1 mg of free chlorine. FIG. 25 shows that the number of bacteria that can be killed by 1 mg of free chlorine uniformly falls within 2.5 to $5\times10^{10}$ irrespective of the sterilizing power. Consequently, the quantity of free chlorine required for killing $1\times10^4$ CFU/mg of bacteria is 0.2 to 0.4 $\mu$g/l. It is probable that the number of bacteria in the standing water can be kept less than $10\times10^4$ CFU/ml by adding more free chlorine than that.
(Embodiment 10)

A test was carried out for investigating the chronological change of the number of bacteria in a urinal placed in the office building that was ordinarily used in the day time and rarely used at night. The investigation was conducted as follows.

First, the average number of bacteria was found to be about $8\times10^2$ CFU/ml when investigated at 7 p.m., i.e. after the working hour.

In case of leaving the urinal untouched overnight, the average increased up to about $1\times10^6$ CFU/ml.

On the other hand, in case the tap water was supplied at 10 p.m. and at 3 a.m. during the night, the number of bacteria was kept at about $1\times10^3$ CFU/ml at 8 a.m. next morning. This is probably because that the standing water was renewed and the bacteria was flushed out by supplying the tap water at 10 p.m. and at 3 a.m. during the night. The renewal rate of the standing water of the toilet is practically about 99%, which means that the same percentage (99%) of bacteria in the standing water can be washed out of the urinal. Here, however, even though the number of bacteria is small, the remaining bacteria can increase since the sterilizing substance is not used, and further new bacteria may come from the air into the standing water. These are the probable reason why the number of bacteria rises up to $1\times10^3$ CFU/ml at 8 a.m. next morning.

Besides, the number of bacteria in the standing water is continuously zero CFU/ml in case of supplying the water containing free chlorine with the concentration of 1 mg/l produced by electrolyzing the tap water, while it is $1\times10$ CFU/ml at the highest in case of supplying the water containing free chlorine with the concentration of 0.5 mg/l produced by electrolyzing the water of the flush tank, and $2\times10^2$ CFU/ml at the highest in case of supplying the water containing free chlorine with the concentration of 0.1 mg/l produced by electrolyzing the tap water.

The probable reason why the number of bacteria cannot be zero in case of supplying the water containing free chlorine with the concentration of 0.5 mg/l or 0.1 mg/l is that, even if the number of bacteria once decreases to zero by supplying the water containing free chlorine at 3 a.m., the concentration of the water containing free chlorine becomes zero before 8 a.m., whereafter new bacteria come from the air into the standing water and increase.

Therefore, in case of supplying the water containing free chlorine at predetermined time intervals, it is preferable to supply another water containing free chlorine after one supply thereof before the concentration of the water containing free chlorine becomes zero, preferably before it becomes 0.2 $\mu$g/l according to the previous embodiment.
(Embodiment 11)

Figure 27:
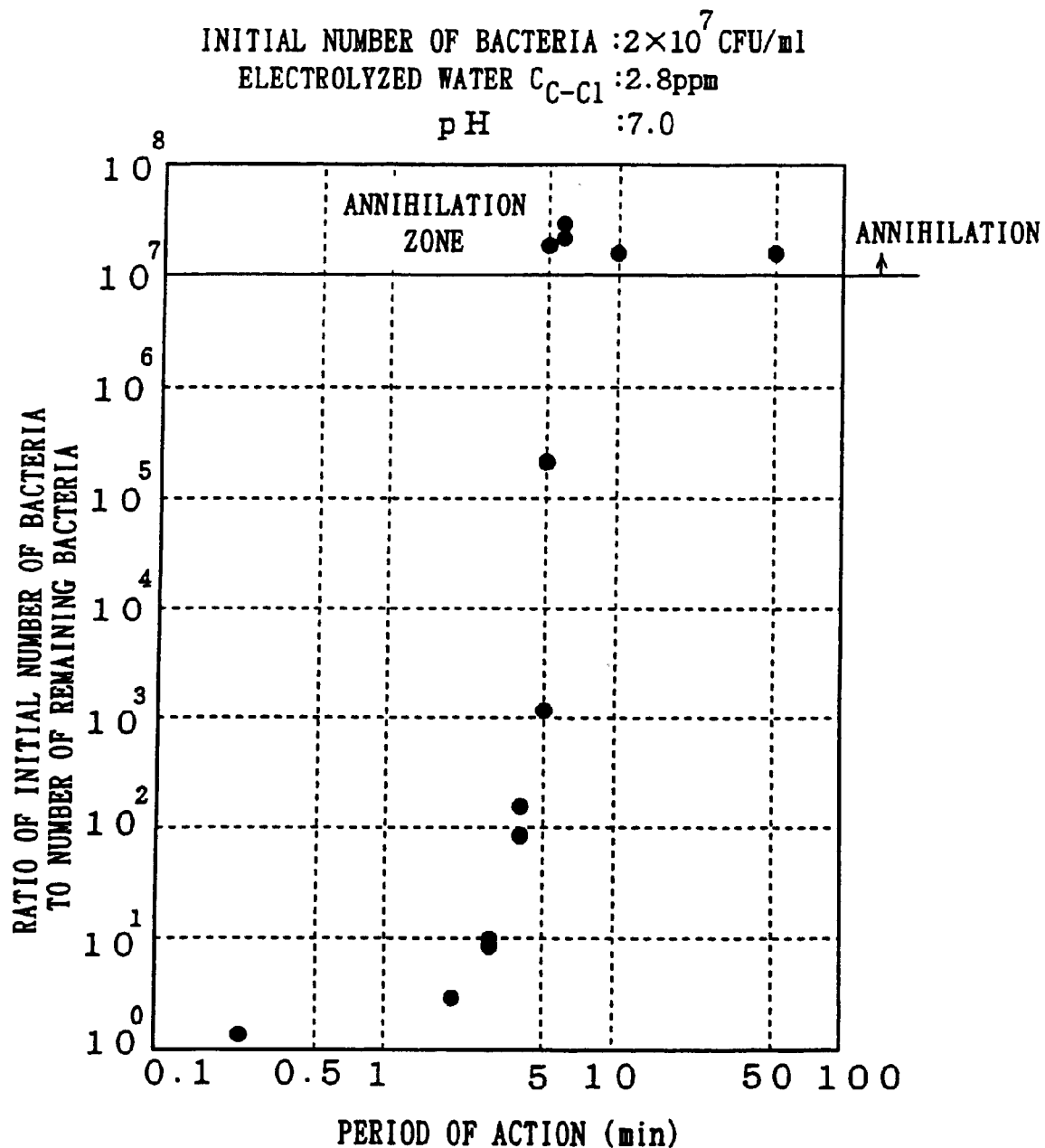
FIG. 27 shows a sterilizing effect (initial number of bacteria/number of bacteria remaining alive) of the water containing bound chlorine applied to the Pseudomonas aeruginosa.

The solution composed of tap water and 20 ppm of ammoniacal nitrogen added thereto is electrolyzed and bound chlorine is produced by 2.8 ppm. Pseudomonas aeruginosa is put in 25 ml of the solution to make the concentration of bacteria $2\times10^7$ CFU/ml. After leaving the solution untouched for a predetermined period of time, the chlorine is collected by sodium thiosulfate, then the number of living bacteria is investigated. Under such conditions, the bacteria are almost annihilated by putting bound chlorine for 5 minutes, as shown in FIG. 27.

What is claimed is:

1. An apparatus comprising:
   a toilet or urinal, said toilet or urinal having a flush water supply line;
   a flush water supply valve in said flush water supply line;
   an electrically operative device selected from the group consisting of continuous electrolytic cells and ozone generators, said device having at least a pair of electrodes, a passage formed between said electrodes, and an inlet leading to and an outlet leading away from said passage;
   a first line communicating said inlet with a point in said flush water supply line upstream of said water supply valve; and
   a second line communicating said outlet with said toilet or urinal while bypassing said flush water supply valve.

2. An apparatus as in claim 1, wherein said second line connects to said flush water supply line at a point downstream of said water supply valve.

3. An apparatus as in claim 1, wherein said toilet or urinal comprises a trap and wherein said second line connects to said toilet or urinal at said trap.

4. An apparatus as in claim 1, further comprising:
   a controller that is operational to control the application of voltage to said electrodes.

5. An apparatus as in claim 4, wherein said first line is provided with a valve and said controller is operational to control said valve.

6. An apparatus as in claim 4, wherein said second line is provided with a valve and said controller is operational to control said valve.

7. An apparatus as in claim 4, wherein:
   said first and second lines are provided with valves;
   said controller is operational to control said first and second line valves; and
   said device is a tank-type electrolytic cell.

8. Apparatus for maintaining the cleanliness of a toilet or urinal, comprising:
   a flush water supply line;
   a flush water supply valve in said flush water supply line;
   an electrically operative device selected from the group consisting of continuous electrolytic cells and ozone generators, said device having at least a pair of electrodes, a passage formed between said electrodes, and an inlet leading to and an outlet leading away from said passage;
   a first line communicating said inlet with a point in said flush water supply line upstream of said water supply valve; and
   a second line configured to communicate said outlet with a toilet or urinal while bypassing said flush water supply valve.

9. Apparatus for maintaining the cleanliness of a toilet or urinal, comprising:
   an electrically operative device selected from the group consisting of continuous electrolytic cells and ozone generators, said device having at least a pair of electrodes, a passage formed between said electrodes, and an inlet leading to and an outlet leading away from said passage;
   a first line configured to communicate said inlet with a point in a flush water supply line upstream of a water supply valve in the flush water supply line; and
   a second line configured to communicate said outlet with a toilet or urinal while bypassing said flush water supply valve.

10. Apparatus for maintaining the cleanliness of a toilet or urinal as in claim 9, wherein said second line is configured to connect to the flush water supply line at a point downstream of the water supply valve.

11. Apparatus for maintaining the cleanliness of a toilet or urinal as in claim 9, wherein said device is a diaphragm-less type electrolytic cell.

12. Apparatus for maintaining the cleanliness of a toilet or urinal as in claim 9, further comprising a controller that is operational to control the application of voltage to said electrodes.

13. Apparatus for maintaining the cleanliness of a toilet or urinal as in claim 12, wherein said first line is provided with a valve and said controller is operational to control said valve.

14. Apparatus for maintaining the cleanliness of a toilet or urinal as in claim 12, wherein said second line is provided with a valve and said controller is operational to control said valve.

15. Apparatus for maintaining the cleanliness of a toilet or urinal as in claim 12, wherein said first and second lines are provided with valves and said controller is operational to control said first and second line valves.

16. Apparatus for maintaining the cleanliness of a toilet or urinal as in claim 15, wherein said device is a tank-type electrolytic cell.

17. Apparatus for maintaining the cleanliness of a toilet or urinal as in claim 16, wherein said controller opens said valve in said second line when the water level in said tank-type electrolytic cell reaches a predetermined level.

18. A method of maintaining the cleanliness of a toilet or urinal having a trap, comprising:
   the step of placing a source of sterilizing metal ions in the trap.

19. A device for maintaining the cleanliness of a toilet or urinal, comprising:
   a container; and
   a source of metal ions within said container;
   said container being configured for placement in the trap of a toilet or urinal.

20. A method of maintaining the cleanliness of a toilet connected to a flush valve in a flush water supply line, said method comprising:
   diverting cleaning water from the flush water supply line at a location upstream of the flush valve;
   treating the cleaning water by passing the cleaning water through a water treatment device; and
   supplying the treated cleaning water to the toilet by directing the treated cleaning water from the water treatment device to the toilet along a flow path bypassing the flush valve.

21. A method as defined in claim 20 further comprising the step of actuating a timer in response to a flush of the toilet, and responding to the timer by initiating said supplying step if the timer indicates that a predetermined period of time has passed before the occurrence of a next subsequent flush of the toilet.

22. A method as defined in claim 21 therein the timer is actuated in response to a flushing operation of the flush valve.

23. A method as defined in claim 20 wherein the treated cleaning water is supplied to the toilet intermittently during a period of time extending between a flush of the toilet and a next subsequent flush of the toilet.

24. A method as defined in claim 23 wherein the treated cleaning water is supplied to the toilet at predetermined intervals within the period of time extending between the flush of the toilet and the next subsequent flush of the toilet.

25. A method as defined in claim 20 wherein said treating step comprises passing the cleaning water between a pair of energizing electrodes.

26. A method of maintaining the cleanliness of a toilet having a flush valve in a flush water supply line, said method comprising:
   drawing cleaning water from the flush water supply line;
   treating the cleaning water;
   responding to a flush of the toilet by actuating a timer; and
   supplying the treated cleaning water to the toilet before the occurrence of a next subsequent flush of the toilet if the timer indicates that a predetermined period of time has passed before the occurrence of a next subsequent flush of the toilet.

27. A method as defined in claim 26 wherein the timer is actuated in response to a flushing operation of the flush valve, and the cleaning water is suppled to the toilet if the timer indicates that the predetermined period of time has passed before the occurrence of a next subsequent flushing operation of the flush valve.

28. A method as defined in claim 26 wherein the treated cleaning water is supplied to the toilet intermittently.

29. A method as defined in claim 28 wherein the treated cleaning water is supplied to the toilet at predetermined intervals.

30. A method as defined in claim 26 wherein said treating step comprises passing the cleaning water between a pair of energized electrodes.

31. A method of maintaining the cleanliness of a toilet having a flush valve in a flush water supply line, said method comprising:
   drawing cleaning water from the flush water supply line;
   treating the cleaning water; and
   supplying the treated cleaning water to the toilet intermittently during a period of time extending between a flush of the toilet and a next subsequent flush of the toilet.

32. A method as defined in claim 31 wherein the treated cleaning water is supplied to the toilet as predetermined intervals within the period of time extending between the flush of the toilet and the next subsequent flush of the toilet.

33. A method as defined in claim 31 further comprising the step of actuating a timer in response to a flush of the toilet, and responding to the timer by initiating said supplying step if the timer indicates that a predetermined period of time has passed before a next subsequent flush of the toilet.

34. A method as defined in claim 31 wherein said treating step comprises passing the cleaning water between a pair of energized electrodes.

35. An apparatus for maintaining the cleanliness of a toilet connected to a flush valve in a flush water supply line, said apparatus comprising:
   means for diverting cleaning water from the flush water supply line at a location upstream of the flush valve;
   means for treating the cleaning water; and
   means for supplying the treated cleaning water to the toilet by directing the treated cleaning water from said treating means to the toilet along a flow path bypassing the flush valve.

36. An apparatus as defined in claim 35 wherein said diverting means and said supplying means together include at least one valve between said upstream location and the toilet, said apparatus further comprising a timer responsive to a flush of the toilet, and control means for responding to the timer by opening said valve if the timer indicates that a predetermined period of time has passed before the occurrence of a next subsequent flush of the toilet.

37. An apparatus as defined in claim 36 therein the timer is responsive to a flushing operation of the flush valve.

38. An apparatus as defined in claim 35 wherein said control means opens said valve intermittently during a period of time extending between a flush of the toilet and a next subsequent flush of the toilet.

39. An apparatus as defined in claim 38 wherein said control means opens said valve at predetermined intervals within the period of time extending between the flush of the toilet and the next subsequent flush of the toilet.

40. An apparatus as defined in claim 35 wherein said treating means passes the cleaning water between a pair of energized electrodes.

41. An apparatus for maintaining the cleanliness of a toilet having a flush valve in a flush water supply line, said apparatus comprising:

means for drawing cleaning water from the flush water supply line;
 means for treating the cleaning water;
 a timer;
 control means for responding to a flush of the toilet by actuating said timer; and
 means for supplying the treated cleaning water to the toilet before the occurrence of a next subsequent flush of the toilet if said timer indicates that a predetermined period of time has passed before the occurrence of a next subsequent flush of the toilet.

42. An apparatus as defined in claim 41 wherein said control means actuates said timer in response to a flushing operation of the flush valve, and said supplying means supplies the cleaning water to the toilet if said timer indicates that the predetermined period of time has passed before the occurrence of a next subsequent flushing operation of the flush valve.

43. An apparatus as defined in claim 41 wherein said supplying means supplies the treated cleaning water to the toilet intermittently.

44. An apparatus as defined in claim 43 wherein said supplying means supplies the treated cleaning water to the toilet at predetermined intervals.

45. An apparatus as defined in claim 41 wherein said treating means passes the cleaning water between a pair of energized electrodes.

46. An apparatus for maintaining the cleanliness of a toilet having a flush valve in a flush water supply line, said apparatus comprising:

means for drawing cleaning water from the flush water supply line;
 means for treating the cleaning water; and
 means for supplying the treated cleaning water to the toilet intermittently during a period of time extending between a flush of the toilet and a next subsequent flush of the toilet.

47. An apparatus as defined in claim 46 wherein said supplying means supplies the treated cleaning water to the toilet at predetermined intervals within the period of time extending between the flush of the toilet and the next subsequent flush of the toilet.

48. An apparatus as defined in claim 46 wherein said diverting means and said supplying means together include at least one valve between said upstream location and the toilet, said apparatus further comprising a timer responsive to a flush of the toilet, and control means for responding to the timer by opening said valve if the timer indicates that a predetermined period of time has passed before the occurrence of a next subsequent flush of the toilet.

49. An apparatus as defined in claim 46 wherein said treating means comprises passing the cleaning water between a pair of energized electrodes.

50. An apparatus comprising:

a toilet or urinal, said toilet or urinal having a flush water supply line;
 a flush water supply valve in said flush water supply line;
 an electrically operative device having at least a pair of electrodes, a passage formed between said electrodes, and an inlet leading to and an outlet leading away from said passage;
 a first line communicating said inlet with a point in said flush water supply line upstream of said water supply valve; and
 a second line communicating said outlet with said toilet or urinal while bypassing said flush water supply valve.

51. An apparatus as defined in claim 50 wherein said second line connects to said flush water supply line at a point downstream of said water supply valve.

52. An apparatus as defined in claim 50 wherein said toilet or urinal comprises a trap and wherein said second line connects to said toilet or urinal at said trap.

53. An apparatus as defined in claim 50 further comprising:

a controller that is operational to control the application of voltage to said electrodes.

54. An apparatus as defined in claim 53 wherein said first line is provided with a valve and said controller is operational to control said valve.

55. An apparatus as defined in claim 53 wherein said second line is provided with a valve and said controller is operational to control said valve.

56. An apparatus as defined in claim 53 wherein:

said first and second lines are provided with valves;
 said controller is operational to control said first and second line valves; and
 said device is a tank-type electrolytic cell.

57. An apparatus for maintaining the cleanliness of a toilet or urinal, comprising:

a flush water supply line;
 a flush water supply valve in said flush water supply line;
 an electrically operative device having at least a pair or electrodes; a passage formed between said electrodes, and an inlet leading to and an outlet leading away from said passage;
 a first line communicating said inlet with a point in said flush water supply line upstream of said water supply valve; and
 a second line configured to communicate said outlet with a toilet or urinal while bypassing said flush water supply valve.

58. An apparatus for maintaining the cleanliness of a toilet or urinal, comprising:

an electrically operative device having at least a pair or electrodes, a passage formed between said electrodes, and an inlet leading to and an outlet leading away from said passage;

a first line configured to communicate said inlet with a point in a flush water supply line upstream of a water supply valve in the flush water supply line; and a second line configured to communicate said outlet with a toilet or urinal while bypassing said flush water supply valve.

59. An apparatus as defined in claim 58 wherein said second line is configured to connect to flush water supply line at a point downstream of the water supply valve.

60. An apparatus as defined in claim 58 wherein said device is a diaphragmless type electrolytic cell.

61. An apparatus as defined in claim 58 further comprising a controller that is operational to control the application of voltage to said electrodes.

62. An apparatus as defined in claim 61 wherein said first line is provided with a valve and said controller is operational to control said valve.

63. An apparatus as defined in claim 61 wherein said second line is provided with a valve and said controller is operational to control said valve.

64. An apparatus as defined in claim 61, wherein said first and second lines are provided with valves and said controller is operational to control said first and second line valves.

65. An apparatus as defined in claim 64 wherein said device is a tank-type electrolytic cell.

66. An apparatus as defined in claim 65 wherein said controller opens said valve in said second line when the water level in said tank-type electrolytic cell reaches a predetermined level.

* * * * *